(12) United States Patent
Genosar

(10) Patent No.: US 11,759,572 B2
(45) Date of Patent: Sep. 19, 2023

(54) ASEPTIC CARTRIDGE AND DISPENSER ARRANGEMENT

(75) Inventor: Amir Genosar, Boulder, CO (US)

(73) Assignee: Aktivax, Inc., Broomfield, CO (US)

( * ) Notice: Subject to any disclaimer, the term of this patent is extended or adjusted under 35 U.S.C. 154(b) by 0 days.

(21) Appl. No.: 13/980,200

(22) PCT Filed: Jan. 17, 2012

(86) PCT No.: PCT/US2012/021592
§ 371 (c)(1),
(2), (4) Date: Sep. 24, 2013

(87) PCT Pub. No.: WO2012/099898
PCT Pub. Date: Jul. 26, 2012

(65) Prior Publication Data
US 2014/0008366 A1    Jan. 9, 2014

Related U.S. Application Data

(60) Provisional application No. 61/584,313, filed on Jan. 9, 2012, provisional application No. 61/581,721, filed
(Continued)

(51) Int. Cl.
*B65D 41/02* (2006.01)
*A61M 5/28* (2006.01)
(Continued)

(52) U.S. Cl.
CPC .............. *A61M 5/28* (2013.01); *A61J 1/2093* (2013.01); *A61J 1/2096* (2013.01);
(Continued)

(58) Field of Classification Search
CPC .............. A61M 5/1782; A61M 5/2046; A61M 5/2066; A61M 5/2448; A61M 5/2455;
(Continued)

(56) References Cited

U.S. PATENT DOCUMENTS 4,484,920 A * 11/1984 Kaufman .............. A61J 1/2093
604/416
4,548,606 A * 10/1985 Larkin .................. A61J 1/2093
604/87
(Continued)

FOREIGN PATENT DOCUMENTS

EP      1308149 A2     5/2003
JP      2001009006 A   1/2001
(Continued)

OTHER PUBLICATIONS

Korean Intellectual Property Office; International Search Report; PCT/US2012/021592; dated Aug. 29, 2012; 3 pp.
(Continued)

*Primary Examiner* — Steven A. Reynolds
*Assistant Examiner* — Prince Pal
(74) *Attorney, Agent, or Firm* — Holzer Patel Drennan

(57) ABSTRACT

A cartridge for use with a beneficial agent delivery device having a fillable reservoir. The cartridge includes a reconstitution, unit dose package having first and second compartments and a fitment. The first compartment contains at least a first constituent of the beneficial agent. The second compartment contains at least a second constituent of the beneficial agent. The fitment is disposed on the package for interfacing the package to the fillable reservoir.

18 Claims, 29 Drawing Sheets

Related U.S. Application Data on Dec. 30, 2011, provisional application No. 61/578,907, filed on Dec. 22, 2011, provisional application No. 61/533,194, filed on Sep. 10, 2011, provisional application No. 61/523,422, filed on Aug. 15, 2011, provisional application No. 61/487,121, filed on May 17, 2011, provisional application No. 61/467,359, filed on Mar. 24, 2011, provisional application No. 61/433,493, filed on Jan. 17, 2011.

(51) Int. Cl.
| | | |
|---|---|---|
| *A61M 5/178* | (2006.01) | |
| *A61M 5/20* | (2006.01) | |
| *A61M 5/24* | (2006.01) | |
| *A61J 1/20* | (2006.01) | |
| *A61M 5/30* | (2006.01) | |
| *A61M 5/315* | (2006.01) | |
| *A61M 5/32* | (2006.01) | |
| *A61M 5/00* | (2006.01) | |
| *A61M 5/31* | (2006.01) | |

(52) U.S. Cl.
CPC ........ *A61M 5/1782* (2013.01); *A61M 5/2046* (2013.01); *A61M 5/2066* (2013.01); *A61M 5/2448* (2013.01); *A61M 5/2455* (2013.01); *A61M 5/30* (2013.01); *A61M 5/31511* (2013.01); *A61M 5/31596* (2013.01); *A61M 5/3202* (2013.01); *A61M 5/3213* (2013.01); *A61M 5/3232* (2013.01); *A61J 1/2024* (2015.05); *A61M 5/002* (2013.01); *A61M 2005/3104* (2013.01); *A61M 2005/3118* (2013.01); *A61M 2005/3121* (2013.01); *A61M 2205/19* (2013.01)

(58) Field of Classification Search
CPC .. A61M 5/30; A61M 5/31511; A61M 5/3202; A61M 5/3213; A61M 5/3232; A61M 5/31596; A61M 5/28; A61M 2205/19; A61M 5/2033; A61M 5/2425; A61M 5/282; A61M 5/2459; A61M 5/2466; A61M 5/284; A61M 5/322; A61M 5/3234; A61M 5/3287; A61M 5/427; A61M 31/002; A61M 37/0015; A61M 2005/3123; A61M 2005/3128; A61M 2005/314; A61M 2005/3022; A61M 2037/0023; A61J 1/2093; A61J 1/2096; A61J 2001/2027; A61J 1/10; A61J 1/067; A61J 1/1406; A61J 1/2024
USPC ....... 220/265; 604/411, 415; 222/1, 105, 94, 222/103
See application file for complete search history.

(56) References Cited

U.S. PATENT DOCUMENTS

| | | | | |
|---|---|---|---|---|
| 4,581,021 A | * | 4/1986 | Landau | A61M 5/2425 604/187 |
| 4,722,733 A | * | 2/1988 | Howson | A61J 1/2096 141/330 |
| 4,961,495 A | | 10/1990 | Yoshida | |
| 4,997,083 A | * | 3/1991 | Loretti | A61J 1/2093 53/433 |
| 5,006,118 A | * | 4/1991 | Yule | A61J 1/2096 383/44 |
| 5,112,303 A | | 5/1992 | Pudenz et al. | |
| 5,171,214 A | * | 12/1992 | Kolber | A61J 1/2096 604/82 |
| 5,176,634 A | | 1/1993 | Smith et al. | |
| 5,334,163 A | | 8/1994 | Sinnett | |
| 5,391,150 A | * | 2/1995 | Richmond | A61J 1/10 604/91 |
| 5,409,125 A | | 4/1995 | Kimber | |
| 6,146,361 A | * | 11/2000 | DiBiasi | A61M 5/42 604/232 |
| 6,918,418 B1 | * | 7/2005 | Farris | A61J 1/2096 141/330 |
| 7,213,702 B2 | * | 5/2007 | Takimoto | A61J 1/067 604/416 |
| 7,425,207 B2 | * | 9/2008 | Miller | A61J 1/065 604/82 |
| 7,625,114 B2 | | 12/2009 | Suchan et al. | |
| 9,820,913 B2 | * | 11/2017 | Genosar | A61M 5/285 |
| 10,028,886 B2 | * | 7/2018 | Genosar | A61J 1/00 |
| 2001/0002433 A1 | * | 5/2001 | Weston | A61M 5/30 604/72 |
| 2002/0138039 A1 | | 9/2002 | Hasegawa | |
| 2006/0169664 A1 | * | 8/2006 | Miller | B65D 1/095 215/48 |
| 2006/0235364 A1 | * | 10/2006 | O'Hare | A61J 1/2096 604/411 |
| 2007/0260188 A1 | * | 11/2007 | Kelly | A61M 5/282 604/187 |
| 2008/0073372 A1 | | 3/2008 | Keller | |
| 2009/0054865 A1 | | 2/2009 | Brandenburger et al. | |
| 2009/0171311 A1 | * | 7/2009 | Genosar | A61M 5/282 604/411 |
| 2010/0042071 A1 | * | 2/2010 | Reynolds | A61J 1/2096 604/520 |
| 2010/0094219 A1 | * | 4/2010 | Kriesel | A61M 5/16881 604/134 |
| 2010/0179473 A1 | * | 7/2010 | Genosar | A61M 5/14248 604/82 |
| 2012/0226239 A1 | * | 9/2012 | Green | A61M 5/1782 604/218 |
| 2012/0241465 A1 | * | 9/2012 | Genosar | B05B 11/0078 222/105 |
| 2012/0241466 A1 | * | 9/2012 | Genosar | A61M 5/282 222/103 |
| 2014/0008366 A1 | | 1/2014 | Genosar | |
| 2014/0346071 A1 | * | 11/2014 | Genosar | A61J 1/067 206/438 |
| 2021/0154098 A1 | * | 5/2021 | Genosar | A61J 1/2048 |

FOREIGN PATENT DOCUMENTS

| | | |
|---|---|---|
| JP | 2003135563 A | 5/2003 |
| JP | 2006-504594 A | 2/2006 |
| JP | 2006175212 A | 7/2006 |
| JP | 2006-230467 A | 9/2006 |
| JP | 2006230467 A | 9/2006 |
| JP | 2008526623 A | 7/2008 |
| JP | 2009171311 A | 7/2009 |
| JP | 6290625 B2 | 3/2018 |
| WO | 2009086463 A1 | 7/2009 |
| WO | 2010/081174 A2 | 7/2010 |

OTHER PUBLICATIONS

International Search Report issued for PCT/US2011/063624 dated Jun. 26, 2012, 4 pages.
International Search Report issued for PCT/US2012/038444 dated Nov. 28, 2012, 3 pages.
Office Action for Chinese Patent Application No. 2016111045382, dated Jul. 25, 2019, 7 pages.
Notification of Reasons for Refusal issued in Japanese Patent Application No. P2020-127979, dated Feb. 9, 2022, 5 pages.

* cited by examiner

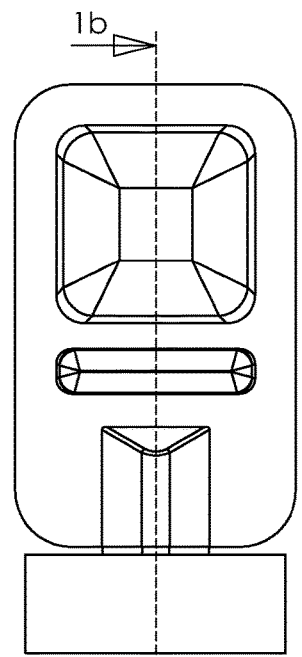
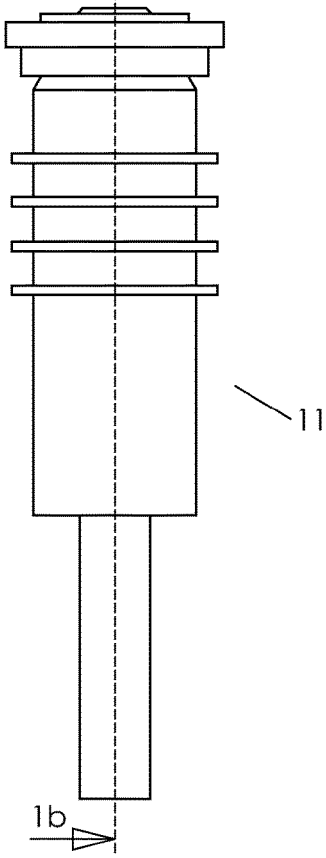
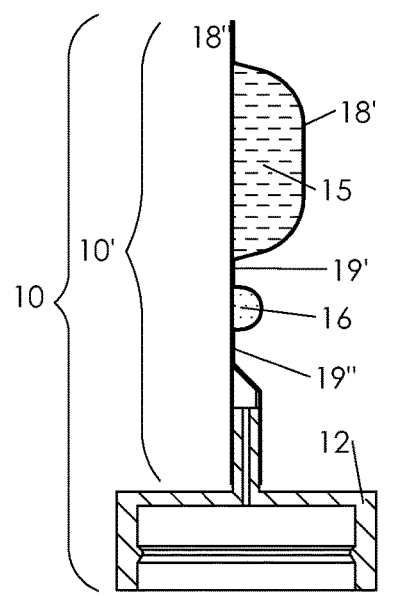
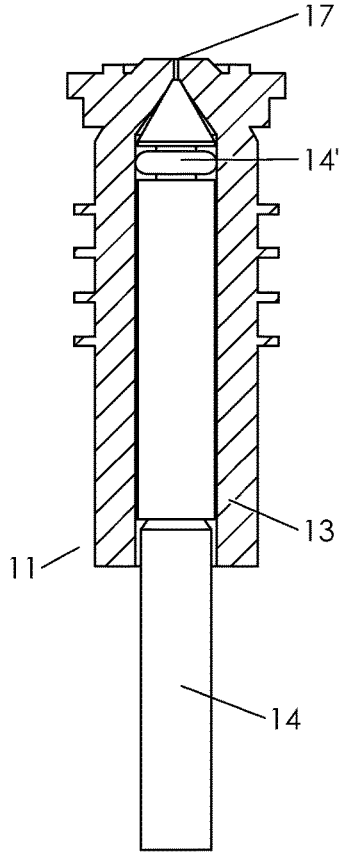
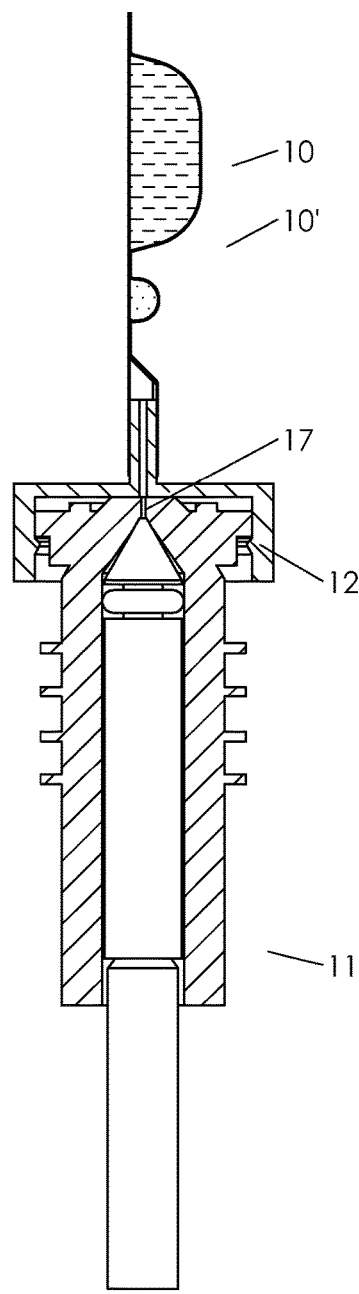
Figure 1a    Figure 1b    Figure 1c

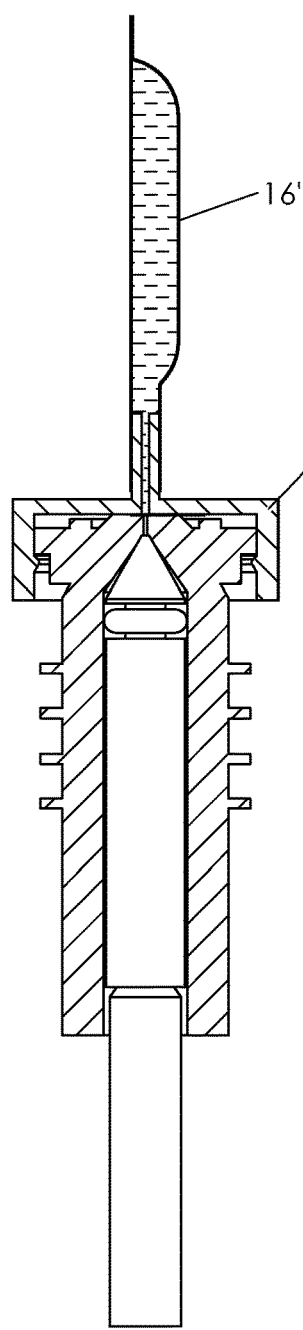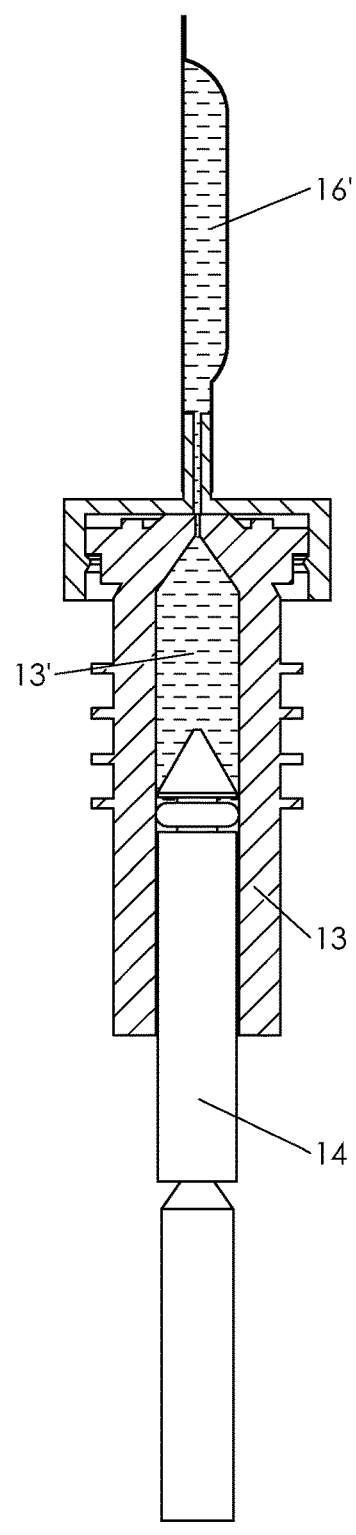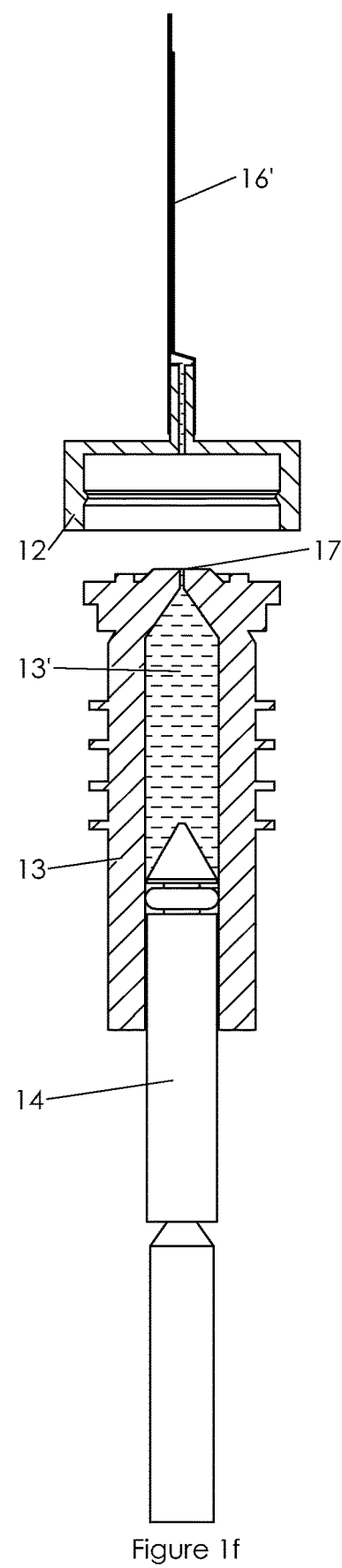
Figure 1d
Figure 1e
Figure 1f

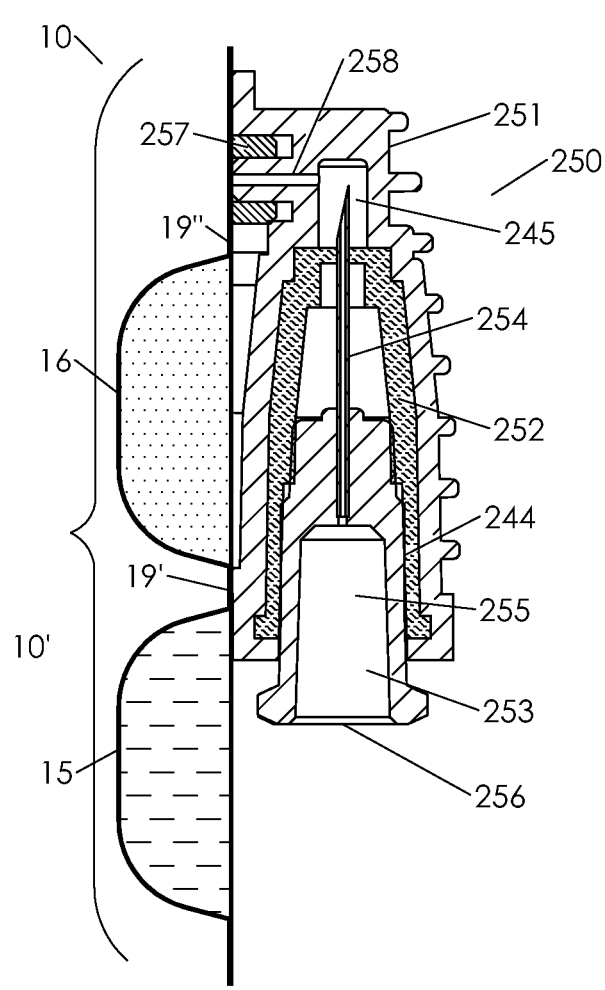
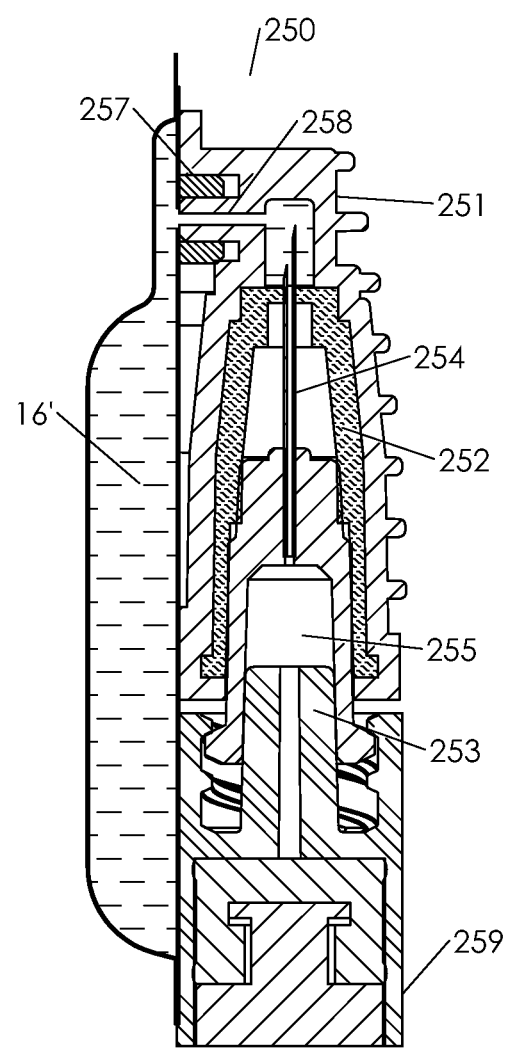
Figure 25a
Figure 25b
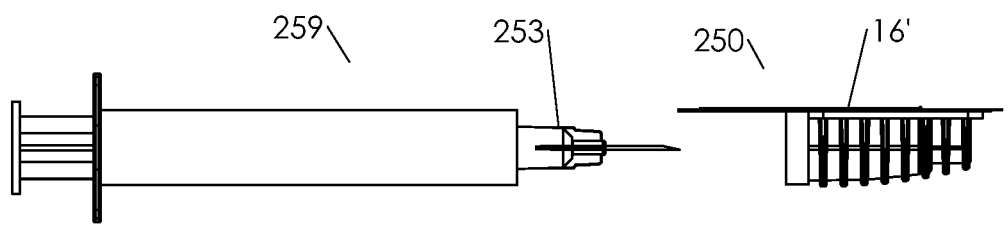
Figure 25c

ASEPTIC CARTRIDGE AND DISPENSER ARRANGEMENT

TECHNICAL FIELD

The present disclosure preferably, but without limitation, generally pertains to disposable cartridges for use with drug delivery devices, and more specifically pertains to aseptic mixing cartridges for drug delivery devices.

BACKGROUND

Medications, and in particular injectable medications, need to be stored sterile in aseptic commercial packages until the time of use. Some medications are stored in pre-filled single dose dispensing devices such as pre-filled syringes, for example the pre-filled syringes from Vetter (Ravensburg, Germany). Yet most of injectable medication are stored in aseptic packages and are transferred to a dispensing device (i.e. drug delivery device) shortly before use. The term dispensing device include without limitation hypodermic syringes, micro-needle syringes, micro-pumps, auto-injectors, jet injectors, topical dispensers, intradermal delivery devices, patch pumps, auricular dispensers, oral dispensers, eye droppers, auto-injectors, infusers, or any other type of drug delivery device.

Several aseptic packages for storing injectable medications are commercially available. Perhaps the most common aseptic package for injectable products is glass vials. Some medications are stored in separate components that are mixed just prior to use. Often this is done to improve the medication's stability or to extend the medication's shelf life. In one example the medication is a vaccine that is kept dry in one vial to extend the vaccine thermo stability; and a companion vial stores a dilutant that is dispensed to the vaccine vial via a syringe and needle prior to injection. In another example the medication is a vaccine where one vial stores the formulated antigen and the second vial stores an adjuvant.

However, there are several drawbacks with this prior art: (a) these packages are often costly and economically impractical to many injectable drugs such as vaccines; (b) where mixing of the medication components is required the process is complex and error prone; and (c) the transfer of the medication or its components from one container to another or to the dispensing device is done in a non-sterile field and is prone to contamination risks.

U.S. Pat. No. 7,879,018 discloses one of several commercial and patented kits for mixing an injectable dose. Here again the limitation of the disclosure is the dependency on vials and the cost and complexities associated with this type of glass primary containers.

Several commercial products and patents disclose a flexible package made from film or foils in which a product can be stored in an aseptic manner until the time of use. Some of these products and patents further disclose a dispensing port communicating with the product in the dispensing package. In some cases a rupturable barrier is presented between the port and the product to enhance the integrity of the package until the time of use. In some cases these flexible packages comprise at least two product compartments that are mergeable prior to use to allow the substances from the different compartments to mix and form the dispensable product. In some cases these packages are made from a film or a foil (together webs) where a first web wall is sealed to a second web wall to define the boundaries of a product compartment. These packages are sometimes referred to as pouches or sachet. One disadvantage of pouch packages is that it is relatively challenging to efficiently express the entire content of the package. This is due to the dimensional ratio of these packages where the length and width of the seal (the compartment's footprint) are typically significantly larger than the perpendicular inflation to the footprint plane. This ratio is an inherent limitation of the way pouch/sachet packages are formed. Pouches and sachets are formed from one or more flat film or foil (together "web") that is sealed along its edges to form one or more receptacle. The pouch is filled during or post formation of the receptacle and then sealed to keep the product aseptically packaged.

When operated directly with the palm, one limitation of these relatively shallow packages is that, when dispensing, the thumb of the operator very quickly bring two opposite walls of the package in contact at which point the dispensing is halted. Sophisticated peristaltic action or folding of the package would typically be necessary to express additional product from the package, not practical for certain applications such as injection. In some arrangements, the flexible package is depressed with a compression panel to cause the content to expel. In these arrangements it is beneficial to operate the compression panel to depress a smaller contact surface of the product compartment, and hence allow developing more pressure. It is therefore advantageous to create a flexible dispensing package where the footprint of the content compartment is relatively small and the ratio between the sealed area and the dimension of the package perpendicular to that surface is smaller.

In some applications, the deliverable medication requires a thorough mix of at least two substances prior to injection. In one example, a simple method is required to prepare a highly viscous water in oil (W/O) at point of use. At present, an emulsion is prepared by hand by mixing separate oil and water components back and forth via three-way stopcock or a narrow tube connecting two syringes. The method is somewhat time consuming and often inconsistent. Connectors that have a porous membrane inside the syringes have been developed to provide more effective emulsion but at the expense of needing stronger pushing force particularly when pore diameter is decreased in order to shorten preparation time. In addition the increased number of assembly and dismantle steps enhance the risks of operation errors and contamination of the deliverable dose.

SUMMARY

At least some aspects of the present disclosure overcome the disadvantages and limitations of the prior art by providing, for example, a low cost, simple and easy to use cartridge. The cartridge, in certain configurations, allows for aseptic mixing and filling of dispensers or other delivery device, and in particular, drug delivery injectors. The terms dispenser, dispensing device, delivery device and delivering device are used interchangeably herein.

In some arrangements of the present disclosure, the package is made from at least one web material wherein a first wall and a second wall of the web material are joined together along a boundary line of a compartment. In some arrangements, the web material is pre-formed such that a relatively large volume of the compartment is achieved with a relatively smaller sealing footprint. This pre-formed package may reduce the overall dimensions of the package and improve storage and transportation efficiencies.

According to one arrangement of the present disclosure, a cartridge having a thin and flexible wall package comprises at least a first constituent compartment and a fitment for connecting the cartridge to a filling port of a dispenser or delivery device. The fitment is attached to the package in a fluid-tight fashion. The fitment may be attached to the filling port of the dispenser by one of the means, but is not limited to a Luer connector, a Luer lock connector, a press-fit connector, a snap-on connector, a snap, a thermal weld, a spike and stopper arrangement, or a screw on cap.

In some arrangements, at least one cavity is pre-formed in at least one of the web walls of the package, which provides a portion of at least one product compartment of the package. This configuration allows a smaller ratio of the sealed area (footprint) of the compartment and the dimension of the compartment perpendicular to the sealed area (the swelling of the compartment), for storing the same volume of product. This configuration also permits a smaller footprint of the compartment than what would be required with a sachet/pouch package with a similar product volume. The term pre-forming, as will be used in this text, refers to giving a material, and particularly a wall of a package, a three dimensional shape. Pre-forming may include creating of a cavity, a dome, a vertical or a substantially vertical wall relative to a generally horizontal and flat original state. Pre-forming of the web may be performed by one of the means known in the art, appropriate to the properties of the particular web material including, for example, thermoforming, cold forming, forming with preheat, plug-assist, pressure forming, vacuum forming, and a combination of the above.

In some arrangements, the package is constructed from a thin wall in one of the forms known in the art including, for example, a blister pack, a pouch, a sachet, a blow-molded container, injection molded container, an extruded container, and a combination thereof. In some arrangements, the package may have more than one compartment for storing a number of substances that need to be mixed prior to delivery to a subject to form the dispensable product. In some arrangements, the package may have more than one compartment for storing a number of substances that need not to be mixed prior to dispensing from the package. The compartments may be separated by a weak seal that can be broken by compressing at least one of the compartments to cause the content to exceed a threshold pressure that will cause the weak seal to separate (e.g., rupture or peel) and allow the substances to mix. The package further comprises an interface to the dispenser or delivery device.

In some arrangements, the product is transferred from the cartridge to the dispensing device. In some arrangements, the cartridge is replaced in the dispensing device. In some embodiments, the cartridge is connected to the dispenser in an aseptic fashion at the manufacturing stage; thus, no integration steps of the cartridge and dispenser are required by the user. This arrangement reduces the possibility for user error or contamination of the device or the deliverable product as it avoids exposure to a non-sterile field prior or during the dispenser filling/loading process. In another arrangement, the cartridge is stored separately from the dispensing device (i.e. syringe, injector, etc.) until the time of use. This arrangement may be advantageous where the drug needs to be stored and transported in a controlled environment, such as in controlled temperature refrigeration, and where packaging density is important for efficient utilization of the refrigeration space. This arrangement may also be advantageous to increase logistic and user flexibility by allowing integration of the cartridge with a dispenser from different sources.

In some arrangements, the dispensing device may be an injector. The term injector may refer to various dispensing products including syringes, micro-infusion pumps and reservoirs of such, pen injectors, reservoir assemblies, syringes, needle-free injectors, drug delivery devices in general, patch devices, etc. More generally, the cartridge of the present disclosure is applicable for dispensing devices including, for example, ocular oral or auricular droppers, spray or foam dispensers, topical applicators, and inhaler devices.

In another arrangement, a static mixer is disposed at the interface between the cartridge and the drug delivery device to enhance the mixing and homogeneity of the deliverable product. An example of a static mixer is taught in U.S. Pat. No. 4,538,920, which is incorporated herein in its entirety by this reference. In some arrangements, the static mixer is constructed as a pattern of passageways formed between the flexible walls of the package by pre-forming and weld sealing in designated areas of the package walls. The static mixer may be merely a narrow nozzle, or a porous component accommodated in the flow passageway between the cartridge and the delivery device. In one arrangement, the static mixer is disposed in the cartridge port. In one arrangement, the cartridge comprises more than one compartment holding different substances, which are merged prior to transferring the content to the delivery device, and the static mixer enhances the mixing of the substances as they are transferred to the delivery device.

In some arrangements, the mixture may be transferred back and forth between the cartridge and delivery device to further mix the substances. In some arrangements, at least one substance is stored in the cartridge and at least one substance is stored in the delivery device and the substances are transferred back and forth between the two to mix the substances. In one arrangement, the cartridge comprises at least a first and a second compartment and at least one static mixer is disposed between the first compartment and the second compartment. Mixing may be enhanced by transferring the substances/mixture from one compartment to the other compartment. At least one compression panel or an arrangement of compression panels may be operated with the cartridge to facilitate the transfer of substances across the static mixer.

The present disclosure also relates to arrangements and methods for facilitating efficient cartridge manufacturing and filling. In one arrangement, a compartment of the package is filled with fluid. The compartment is pre-formed and sealed leaving a designated passageway open that leads to a port through which the fluid is introduced and the air is evacuated. A separate passageway for gas evacuation may be incorporated. The passageway may be constructed such that the fluid entering the port glides along the wall of the package, hence avoiding jetting, and minimizing foaming or air bubble formation, thus allowing increased filling rate.

In another arrangement, a liquid substance is frozen prior to filling and is introduced into the package in a solid form. The temperature around the package and the heat transfer to the package during the filling process is controlled such that the frozen liquid remains substantially solid until the compartment is sealed. The frozen liquid substance dose may be inspected in that form prior or during filling. This filling arrangement and method enhances the filling speed and the substance inspection capability. In one arrangement, a dry powder substance has to be filled into the cartridge compartment. To facilitate proper filling of the powder, the powder is slightly compressed to form a loosely aggregated tablet and is filled in that form into the compartment of the package. The tablet may be inspected prior or during filling to the cartridge. In one arrangement, after the tablet has been sealed in the compartment, the compartment is externally manipulated to de-agglomerate the tablet, thus improving the substance solubility at the time of mixing with a dilutant. The external manipulation may be at least one of, but not limited to, compression of the compartment, vibration including, for example, ultrasonic vibration, radio frequency vibration, acoustic vibration, applying mechanical impact to the compartment, and exposure to high or low temperatures.

The present disclosure further relates to arrangements that enhance the barrier properties of the package by including a high barrier peelable opaque wall layer. The peelable high barrier layer may include an aluminum laminate or foil that provides the benefits of light blocking, and substantially complete moisture and oxygen barrier. In order to have a visual inspection of the content of the cartridge prior to use, the high barrier layer is peeled from at least a portion of the package, exposing a substantially see-through wall. In one arrangement, the peelable layer is an integral layer or layers of the multi-layer web material from which the package is made. In another arrangement the peelable layer is applied to the see-through wall during the cartridge manufacturing process. In one arrangement the peelable layer is flat. In another arrangement the peelable layer is pre-formed to accommodate the form of the substance or compartment that it is protecting. In one arrangement, the peelable layer comprises a registered adhesive coating selectively applied to the sealing circumference of the peelable layer. In one arrangement, the cartridge is in the fashion of a flexible clear-wall tube, and the peelable layer is arranged to wrap around the tube.

Another aspect of the present disclosure relates to a cartridge for use with a beneficial agent delivery device having a fillable reservoir. The cartridge includes a unit dose mixing package having first and second compartments, and a fitment. The first compartment contains at least a first constituent of the beneficial agent. The second compartment contains at least a second constituent of the beneficial agent. The fitment is disposed on the package for interfacing the package to the fillable reservoir.

The cartridge may be adapted to communicate with a delivery portion of the delivery device that comprises one of a needle, a catheter, a canula, a connector and a nozzle. The delivery portion may include a needle, and the fitment seals around the needle to minimize fluidic dead-space. The cartridge may include a rupturable barrier between the first compartment and the fitment. The first compartment may be segregated from the second compartment by a rupturable barrier. At least a portion of the package may include a flexible wall. At least a portion of the flexible wall may include a foil. At least a portion of the flexible wall may be pre-formed to define at least a portion of the first and second compartments. At least a portion of the flexible wall may include a peelable foil layer. At least a portion of the peelable foil layer may be pre-formed.

The cartridge may include a fluid passageway between the first and second compartments. The cartridge may include a static mixer disposed in the fluid passageway. The cartridge may include a fluid passageway between the package and the delivery device, and a static mixer disposed in the fluid passageway. The package may include a flexible wall that forms at least a portion of a removable aseptic closure to the fitment.

The cartridge may include a filling compartment, a fluid passageway, wherein the filling compartment is in fluid communication with the first compartment via the fluid passageway. The cartridge may include first and second package walls, and the filling compartment may be located between the first and second package walls of the package.

The fluid passageway may be sealable. The fluid passageway may be sealable to hermetically seal the first compartment after filling. The fluid passageway may be sealable to prevent backflow to the filling compartment during or after filling. A thermal seal may be included between the first and second package walls to seal the fluid passageway. The cartridge may include an insert disposed in at least one of the filling compartment and the fluid passageway. The insert may provide at least a portion of a flow control device such as a valve, a check-valve, a flow restrictor, a flow regulator, a flow deflector, and a combination of the above. The filling compartment may be at least partially defined by a well, compartment or cavity pre-formed in at least one of the first and second package walls of the package. A filling system may be configured to communicate with the filling compartment through a fluid-tight seal. The fluid passageway may be formed to direct fluid to the package along the first package wall of the first compartment to prevent jetting, bubbles and foaming. The cartridge may include a gas evacuation compartment in communication with the first compartment via a fluid evacuation passageway, wherein the fluid evacuation passageway is sealable to hermetically seal the package after filling. At least a portion of the package may include a tubular construction. The fitment may be configured to guide the package toward interfacing with the fillable reservoir. The guidance may be a linear guidance. The cartridge may include a closure segregating the first compartment from the fitment until opened. The cartridge may include a backing to support at least a portion of the package.

Another aspect of the present disclosure relates to an aseptic cartridge for use with a beneficial agent delivery device having a fillable reservoir. The cartridge includes a package having at least a first compartment and a fitment. The first compartment contains at least one constituent of the beneficial agent, and the package is at least partially defined by a pre-formed flexible wall. The fitment is disposed on the package for interfacing the package in fluid communication with the fillable reservoir.

The package may include the first compartment containing a first constituent of the beneficial agent, and a second compartment containing a second constituent of the beneficial agent, wherein the second compartment is segregated from the first compartment by a rupturable barrier also referred to as a closure, or a frangible seal. At least a portion of the flexible wall may include a foil or film, generally referred to as web or webbing. At least a portion of the flexible wall may include a peelable foil layer. At least a portion of the peelable foil layer may be pre-formed. The cartridge may include a fluid passageway extending between the first and second compartments. The cartridge may include a static mixer disposed in the fluid passageway. The cartridge may include a fluid passageway located between the package and the delivery device, and a static mixer is disposed in the fluid passageway. The package may include a flexible wall that extends to form at least a portion of an aseptic closure to the fitment.

The cartridge may include a filling compartment, a fluid filling passageway, wherein the filling compartment is in fluid communication with the first compartment via the fluid filling passageway. The cartridge may include first and second package walls, and the filling compartment may be located between the first and second package walls. The fluid filling passageway may be sealable. The fluid filling passageway may be sealable to hermetically seal the package after filling and to prevent backflow to the filling compartment during or after filling. The fluid filling passageway may be sealed by thermally sealing between the first and second package walls. The cartridge may include an insert disposed in at least one of the filling compartment and the fluid filling passageway. The insert may include at least one of a valve, a check valve, an isolation valve, a flow restrictor, a flow regulator, a pressure restrictor, a pressure regulator, a flow deflector, a nozzle, a stopper, and a seal. The insert may provide at least a portion of a flow control device such as a valve, a check-valve, a flow restrictor, a flow regulator, a flow deflector, and a combination of the above. The filling compartment may be at least partially defined by a well pre-formed in at least one of the first and second package walls. The filling compartment may be configured to communicate with a filling system through a fluid-tight seal. The fluid filling passageway may direct fluid to the package along a first package wall to prevent jetting, bubbles or foaming. The cartridge may include a gas evacuation chamber in communication with the first compartment via a sealable fluid evacuation passageway to hermetically seal the package after filling. The cartridge may include a closure segregating the first compartment from the fitment until opened. The cartridge may be configured to contain a unit-dose of an injectable product or at least one constituent thereof. The fitment may be configured to guide the package toward interfacing with the fillable reservoir. The guidance may be a linear guidance. The cartridge may include a backing to support at least a portion of the package.

A further aspect of the present disclosure relates to a cartridge for use with a beneficial agent delivery device having a fillable reservoir. The cartridge includes a backing and a package assembly. The package assembly includes at least a first compartment and a fitment. The first compartment contains at least one constituent of the beneficial agent and is at least partially defined by a flexible wall. The fitment is disposed on the package for interfacing the package in fluid communication with the fillable reservoir.

The cartridge and the delivery device may be joined via the backing. The backing may include a fluid passageway interconnecting the cartridge and the delivery device. The fluid passageway may be aseptically sealed. The fluid passageway may include a closure separating the first compartment from the reservoir until opened. The cartridge may include a rupturable barrier between the first compartment and the fitment. The package assembly may include at least a second compartment containing at least a second constituent of the beneficial agent, wherein the second compartment is separated from the first compartment by a rupturable barrier. At least a portion of the flexible wall may include a foil. The flexible wall may be pre-formed to define at least a portion of the first compartment. At least a portion of the flexible wall includes a peelable foil layer. At least a portion of the peelable foil layer may be pre-formed. The cartridge may include a fluid passageway positioned between the first and second compartments. The cartridge may include a static mixer disposed in the fluid passageway. The cartridge may include a static mixer disposed in a fluid passageway that is positioned between the package assembly and the delivery device. The flexible wall may extend to form at least a portion of an aseptic closure to the fitment.

The cartridge may include a filling compartment, a fluid filling passageway, wherein the filling compartment is arranged in fluid communication with the first compartment via the fluid filling passageway. The cartridge may include first and second package walls, and the filling compartment may be located between the first and second package walls. The fluid filling passageway may be sealable. The fluid filling passageway may be sealable to prevent backflow to the filling compartment after filling. The fluid filling passageway may be sealed by thermally sealing between the first and second package walls. The cartridge may include an insert disposed in at least one of the filling compartment and the fluid filling passageway. The insert may include at least one of a valve, a check valve, an isolation valve, a flow restrictor, a flow regulator, a pressure restrictor, a pressure regulator, a flow deflector, a nozzle, a stopper, and a seal. The filling compartment may be at least partially defined by a well formed in at least one of the first and second package walls. The cartridge may include a filling system configured to communicate with the filling compartment via a fluid-tight seal. The fluid filling passageway may direct fluid held by the package along a first package wall to prevent jetting. The cartridge may include a gas evacuation chamber in communication with the first compartment via a fluid evacuation passageway, wherein the fluid evacuation passageway is sealable to prevent flow from the first compartment after filling. The delivery device may be selected from the group consisting of a medical syringe, staked needle syringe, safety syringe, retractable needle syringe, auto-disabling syringe, auto-injector, jet-injector, intradermal syringe, subcutaneous syringe, intramuscular syringe, infusor, infusion pump, sustained release delivery system, and patch pump.

The cartridge may be configured to communicate with an administration portion of the delivery device. The administration device may be selected from a needle, a canula, a catheter, a connector, a Luer connector, a nozzle, a spray nozzle, a jet nozzle, a dispenser, an oral dispenser, an auricular dispenser, an ocular dispenser, a topical dispenser, or a coupler to the one of the above.

Another aspect of the present disclosure relates to a cartridge for use with a beneficial agent delivery device having a fillable reservoir and an administration device. The cartridge includes a coupler and a package having at least a first compartment and a fitment. The first compartment contains at least one constituent of the beneficial agent. The fitment is disposed on the package. The coupler is joined to the delivery device for interfacing the fitment in fluid communication with the fillable reservoir.

The coupler may include at least one closure interrupting the fluid communication until opened. The coupler may be movable relative to at least one of the fitment and the delivery device from a first position where said closure is interrupting said fluid communication to a second position where the closure is opened. The coupler may be aseptically sealed. The coupler may include an injection needle interfaceable with the delivery device. The coupler may include a membrane interrupting the fluid communication, wherein the membrane is pierceable by a tip of the injection needle. The injection needle may be movable from a first position wherein the membrane is not pierced to a second position wherein the membrane is pierced. The coupler may be configured to communicate with an administration device. The coupler may include a valve controlling the flow into and out of the package. The valve may be operative by a relative motion between the fitment and the coupler. At least a portion of the package may be detachable from the coupler. The package may be detachable from the coupler after the reservoir has been at least partially filled with the beneficial agent. The coupler may include a safety device from a group consisting of a needle stick prevention device and a reuse prevention device, wherein the safety device is joined with the delivery device when a portion of the cartridge is removed from the delivery device. The cartridge may include a backing for the package. The coupler may be configured as a cap of at least one of the delivery device and the administration device. The delivery device may be selected from a group consisting of a medical syringe, staked needle syringe, safety syringe, retractable needle syringe, auto-disabling syringe, auto-injector, jet-injector, intradermal syringe, subcutaneous syringe, intramuscular syringe, infusor, infusion pump, sustained release delivery system, and patch pump. The administration device may be selected from a group consisting of a needle, a catheter, a connector, a Luer connector, a nozzle, a jet injector nozzle, a dispenser, a micro-needle, an ID needle, an IM needle, a SQ needle, an oral dispenser, an ocular dispenser, an auricular dispenser, a topical dispenser, and a coupler to one of the former. The coupler may include at least a portion of a syringe piston. The coupler may include at least a portion of a syringe barrel. The coupler and fitment may be joined by at least one of a press fit, a thermal weld, and a bonding. The delivery device may include a syringe and the administration device may include a needle, and the coupler may be configured to join the needle with the fitment. The coupler may be configured to guide the needle and the fitment toward joining. The coupler may provide a needle protector. The coupler may provide an aseptic closure for the needle that is maintained until the cartridge and syringe are joined.

The coupler may be configured to communicate with a syringe of a delivery device that comprises a needle, and to be joined with the fitment when the package is joined with the syringe. The delivery device may include a needle protector that is removable when the package and syringe are joined. The delivery device may include an aseptic closure for the needle that is maintained until the package and syringe are joined. The coupler may be configured to fix a position of a tip of the needle. The cartridge may include a glider disposed in an inner bore of the coupler, wherein at least a portion of the glider is axially movable between a distal tip of the needle and a proximal end of the needle. The coupler may remain joined with the fitment when the cartridge is removed from the syringe. The coupler may remain joined with the delivery device when the cartridge is removed from the syringe.

The cartridge may include a fluid passageway for fluid communication between the package and the reservoir, wherein the fluid passageway is terminated by a membrane that is pierceable by an injection needle. The package may include at least one flexible wall that is pre-formed to define at least a portion of the first compartment. The package may include at least one flexible wall having a peelable foil layer portion. At least some of the peelable foil layer may be pre-formed. The cartridge may include a fluid passageway located between the first compartment and a second compartment of the package. The cartridge may include a static mixer disposed in the fluid passageway. The cartridge may include a fluid passageway positioned between the package and the delivery device, and a static mixer disposed in the fluid passageway. The package may further include a flexible wall that extends to form at least a portion of an aseptic closure to the fitment.

The cartridge may include a filling compartment, a fluid filling passageway, wherein the filling compartment is arranged in fluid communication with the first compartment via the fluid filling passageway. The cartridge may include first and second package walls, and the filling compartment may be positioned between the first and second package walls. The fluid filling passageway may be sealable. The fluid filling passageway may be sealable to prevent backflow to the filling compartment after filling. The fluid filling passageway may be sealed by thermally sealing between the first and second package walls. The cartridge may include at least one insert disposed in at least one of the filling compartment and the fluid filling passageway. The insert may include at least one of a valve, a check valve, an isolation valve, a flow restrictor, a flow regulator, a pressure restrictor, a pressure regulator, a flow deflector, a nozzle, a stopper, and a seal. The filling compartment is at least partially defined by a well formed in at least one of the first and second package walls. The cartridge may include a filling system configured to communicate with the filling compartment through a fluid-tight seal. The fluid filling passageway may direct fluid held by the package along a first package wall to prevent jetting. The cartridge may include a gas evacuation chamber in communication with the first compartment via a fluid evacuation passageway, wherein the fluid evacuation passageway is sealable.

A further aspect relates to a cartridge for use with a beneficial agent delivery device having a fillable reservoir. The cartridge includes a package containing all of a beneficial agent dose or all constituents thereof. The cartridge includes a package comprising at least a first compartment containing all of the beneficial agent or at least one constituent thereof, wherein the first compartment is at least partially defined by a flexible wall. The package also includes a fitment disposed on the package for interfacing the package in fluid communication with the fillable reservoir. The beneficial agent delivery device may provide a unit dose. The beneficial agent delivery device may include a unitary reservoir.

The dose may be an injectable dose. The injectable dose may be larger than 0.1 ml and smaller than 5 ml. The injectable dose may be larger than 0.3 ml and smaller than 3 ml. The fitment may be configured to guide the cartridge toward interfacing the unit dose package in fluid communication with the fillable reservoir.

A further aspect relates to a pre-filled cap for enclosing an administration portion of a unit dose beneficial agent delivery device comprising a unitary reservoir. The pre-filled cap includes at least a first compartment containing at least one constituent of the beneficial agent, and a fluid passageway for communicating the first compartment with the administration portion.

The first compartment may include a wall, and at least a portion of the wall comprises a flexible material. The flexible material may include a webbing. The first compartment may include a first constituent of the beneficial agent, and further includes a second compartment containing a second constituent of the beneficial agent, and an openable closure separating the first and second constituents. The administration portion may include one of a needle, a catheter, a connector, a Luer connector, a nozzle, a jet injector nozzle, a dispenser, a micro-needle, an ID needle, an IM needle, a SQ needle, an oral dispenser, an ocular dispenser, an auricular dispenser, a topical dispenser, and a coupler to one of the former. The administration portion may be configured to interface with a delivery device from the group of a medical syringe, staked needle syringe, safety syringe, retractable needle syringe, auto-disabling syringe, auto-injector, jet-injector, intradermal syringe, subcutaneous syringe, intramuscular syringe, infusor, infusion pump, sustained release delivery system, and patch pump.

The pre-filled cap may include a closure that separates the first compartment and the administration portion until the closure is opened. The cap is movable relative to at least one of the package and the administration portion from a first position to a second position thereby opening said closure. The pre-filled cap may include a fluid passageway. The pre-filled cap may include a membrane occluding the fluid passageway. The administration portion may include a needle that is movable to pierce the membrane to establish fluid communication with the fluid passageway. The administration portion may include a needle configured to pierce the membrane to establish fluid communication with the fluid passageway. The pre-filled cap may include a backing for at least a portion of said package. The first compartment may be formed in a package that includes a fitment. At least a portion of the package may include a webbing. The administration portion may be aseptically sealed in the cap. At least a portion of the administration portion is protected by the cap.

Another example beneficial agent unit dose dispenser, in accordance with the present disclosure, includes a delivery device and a cartridge. The delivery device has a fillable unit dose reservoir and at least one port in communication with the fillable reservoir. The cartridge is configured to aseptically join to the delivery device and includes a unit dose package. The unit dose package includes at least a first compartment, a fitment, and an openable seal. The first compartment contains at least one constituent of the beneficial agent, and the package is at least partially defined by a flexible wall. The fitment is joined with the unit dose package and interfaces the unit dose package to the delivery device. The openable seal is disposed between the first compartment and the reservoir.

The reservoir may be substantially empty prior to use. The reservoir may contain at least one constituent of the beneficial agent.

Another aspect of the present disclosure relates to a pre-filled syringe for dispensing a beneficial agent. The pre-filled syringe includes a piston assembly, a fillable barrel comprising an administration portion and a portion for receiving the piston assembly, and a pre-filled cartridge comprising at least a first compartment containing at least a first constituent of the beneficial agent, and a flow passageway for communicating contents from the first compartment to the barrel.

The administration portion may include one of a needle, an IM needle, a micro-needle, an ID needle, a SQ needle, an IM needle, a safety needle, a retractable needle, a needle with a protective sleeve, a nozzle, a jet injection nozzle, a dispenser, and an applicator. The pre-filled syringe may include a cap sealing the administration portion, wherein the cartridge is integrated with the cap. The pre-filled syringe may include a flow passageway that communicates with the barrel via the administration portion. The barrel may include at least a second constituent of the beneficial agent. The pre-filled syringe may include a closure separating the first compartment from the barrel until opened. The cartridge may be movable to open the closure. The pre-filled syringe may be configured for manual operation. The pre-filled syringe may be configured to be operated by at least one of an auto injector, a syringe pump, a controlled actuator, a mechanical ram or pressure. A proximal end of the barrel may be aseptically sealed.

A further aspect of the present disclosure relates to a cap for an administration portion of a delivery device. The cap comprises a fluid passageway, a proximal end configured to communicate with the administration portion, and a distal end.

The cap may include an adapter positioned at the distal end of the fluid passageway for communicating with a pre-filled package. The adapter may be configured to communicate with a fitment of the pre-filled package. A closure may be disposed in the fluid passageway and configured to separate the distal end and the proximal end of the fluid passageway until opened. The cap may be movable to open the closure. The proximal end may be configured to communicate with the administration portion via a coupler. The cap may be configured to seal to the administration portion. The cap may be configured to maintain the administration portion aseptically sealed. The cap may include a backing to support a pre-filled package.

An example method, in accordance with the present disclosure, relates to a method for forming a pre-filled package of a beneficial agent. The method includes providing a webbing having a first side and a second side joined together to form a boundary of at least a first constituent compartment therebetween, forming a frangible seal along at least a portion of the boundary, forming a permanent seal such that the permanent seal overlaps at least some of the frangible seal to create an overlapped portion having substantially the same sealing properties as the permanent seal, and filling the first constituent compartment.

The frangible seal may be formed along the entire boundary. The method may include filling the first constituent compartment with at least the first constituent of the beneficial agent prior to forming the frangible seal. The first constituent compartment may be filled with at least a first constituent of the beneficial agent after forming the frangible seal and prior to forming the permanent seal. The method may include forming a filling access for the first constituent compartment, and the permanent seal seals the filling access. The frangible seal may exhibit a first peeling strength characteristic and the permanent seal may exhibit a second peeling strength characteristic, wherein the first and second peeling strength characteristics are derived by a sealing setting of sealing equipment used to form the frangible and permanent seals. The frangible seal may exhibit a first peeling strength characteristic and the permanent seal may exhibit a second peeling strength characteristic, wherein the first peeling strength characteristic is attributed to a local sealing property of the webbing. The second seal may overlap a majority of the frangible seal. The boundary may define at least a second compartment, and wherein a frangible seal section remains between the first and second compartments after the permanent seal is formed. The method may include providing an outlet port and a passageway to the outlet port that is defined by the permanent seal, wherein a frangible seal section remains between the first constituent compartment and the outlet port.

Another example method in accordance with the present disclosure relates to a method of forming a pre-filled package of a beneficial agent. The method includes forming a gas-filled compartment for the beneficial agent, and forming a filling compartment having a filling port communicating with the gas-filled compartment via a first sealable channel. The method also includes coupling a source of at least a first constituent of the beneficial agent with the filling port in a fluid-tight fashion, filling the gas-filled compartment from the source via the filling channel while evacuating gas through the exhaust port, and sealing the first sealable channel and the filling channel.

The method may include forming an exhaust compartment having an exhaust port communicating with the gas-filled compartment via a second sealable channel. Filling the gas-filled compartment from the source via the filling channel may be done while evacuating gas through the evacuation port. At least a portion of one of the gas-filled compartment, the filling compartment, and the first sealable channel may be pre-formed. The method may include trimming the pre-filled package to remove at least one of the filling and exhaust ports. At least a portion of the pre-filled package may include a webbing. The webbing may be pre-formed to define a volume of the gas-filled compartment. The pre-filled package may be accommodated in a cavity during filling to further accurately define a volume for the gas-filled compartment. A vacuum may be applied to the cavity. During filling, the pre-filled package may be positioned such that the second sealable channel is elevated relative to the first sealable channel. The filling port may include a well. The method may include disposing at least a first insert in at least one of the first compartment, the first channel, and the second channel. The insert may interface with the source of the first constituent. The interface may include a valve. The filling compartment and the first sealable channel may be hermetically sealed from the environment prior to the filling step.

The method may include, prior to filling, piercing a wall of the filling port to receive the source of the first constituent. The source of the first constituent may include a capillary tube terminating with a piercing element. The capillary tube may pierce a web wall of the filling port, wherein the web forms a fluid-tight seal with the filling tube. The method may include stacking a plurality of the pre-filled packages and transporting the stacked pre-filled packages to a filling machine. The method may include sterilizing the package after the compartment forming step and prior to the filling step. At least one of the first sealable channels may include a sealable insert. The first fillable channel may be made such that during the filling step the first constituent flows along a wall of the filling compartment to prevent jetting, foaming, or bubbles.

The method may include providing a sensor for detecting presence of the constituent in the second sealable channel, and indicating with the sensor that the filling compartment is filled. The source of the first constituent may include a metering pump. The source of the first constituent may include a non-metering pumping system. The pre-filled package may include an evacuation line for receiving the gas evacuated through the evacuation port. The method may include applying a vacuum at the evacuation port. The first constituent may include solid matter from a group consisting of powder, pellets, granules, tablets, agglomerates, spheres and micro-spheres. During the filling step, the first constituent may be transported to the first compartment with a gas flow. A size of at least one opening of the second sealable channel may limit the first constituent from exiting the evacuation port. The pre-filled package may be manufactured on a form-fill-seal line. A plurality of the pre-filled packages may be manufactured from a single web member. The source of the first constituent may be attached to the filling port using vacuum. At least one of the filling compartment and the sealable channels are molded to shape. The gas-filled compartment may be pre-formed to define substantially the fill volume of the beneficial agent.

A further method incordance with the present disclosure relates to a method of producing a unit-dose delivery system for a beneficial agent that includes receiving an assembled delivery device, receiving a pre-filled, aseptically sealed cartridge which has been pre-filled with at least a first constitutent of the beneficial agent, and integrating the delivery device and the aseptically sealed cartridge.

The delivery device may be a syringe comprising a piston preassembled to a barrel. The delivery device and cartridge may be pre-sterile, and the method further includes aseptically integrating the delivery device and cartridge. The method may include terminally sterilizing the delivery device after integration.

Another example method relates to filling a package with a unit-dose of beneficial agent in a liquid state. The method includes freezing a metered unit-dose of the beneficial agent in a mold to create a frozen dose, placing the frozen dose in a semi-finished compartment, and sealing the compartment.

The package may include a blister pack and the frozen dose is placed in a pre-formed cavity in the blister pack. The method may include inspecting the frozen dose for at least one controlled property prior to placing the frozen dose in the compartment. The method may include manufacturing the package from at least a first web material and freezing the unit-dose onto the first web material. The method may include thawing the frozen dose after sealing the compartment. The method may include exposing the frozen dose to a temperature sufficiently low to prevent thawing prior to sealing the compartment.

Another example method relates to filling a package with a metered dose of at least a first constituent of a beneficial agent in a particulate solid material form. The method includes metering a dose of the first constituent, compressing the metered dose enough to form a unitary body, placing the unitary body in a semi-finished package, sealing the package, and directing energy at the unitary dose through a wall of the package to deagglomerate the unitary body.

The method may include inspecting the unitary body to at least one controlled property prior to placing the unitary body in the package. The package may be made at least partially from at least a first web, and the method includes compressing the unitary body onto the first web. The method may include forming the package on a form-fill-seal line. At least a portion of the package may include a web material and the energy is directed by depressing the unitary body through a flexible wall of the package. The energy may be directed to the unitary body by at least one of mechanical vibration, ultrasonic vibration, audio vibration and RF vibration.

Another aspect of the present disclosure relates to a coupler for facilitating the integration of a dispensing device and a cartridge. The dispensing device includes a reservoir and an administration device, the cartridge includes a package containing content of at least a first dispensable product, or at least a first constituent thereof, and a fitment for connecting the cartridge in communication with the administration device to allow for transfer of said content or at least first constituent thereof to said reservoir. The coupler includes a first end and a second end, wherein the first end being configured to receive the administration device, and the second end is configured to movably receive the fitment and guide the fitment into engagement with the administration device so that the cartridge and the dispensing device are in fluid communication.

The coupler may include a glider movable within the coupler, wherein the glider holds the distal end of the administration device in a predetermined first position in the coupler, and moves toward a second position wherein the glider provides clearance for the fitment to engage with the administration device. The glider may provide a fluid-tight seal with at least one of the administration device, the coupler, and the fitment. The glider may aseptically seal the administration device in the coupler. The glider may aseptically seal the reservoir. The glider may be biased to the first position. The coupler may provide a physical shield to the administration device.

The coupler may engage with at least one of the cartridge and the dispensing device via at least one of a press-fit, snap-fit, threaded engagement, a bionet, a helical connection, or an elevated ramp. The coupler may be configured to remain joined with the cartridge when the cartridge is disengaged from the dispensing device. The coupler may be configured to remain joined with the dispensing device when the cartridge is disengaged from the dispensing device. The administration device may be a needle and the coupler provides a needle shield.

A further aspect relates to a medical syringe that includes an administration needle at a distal end of the syringe, and a coupler received at the distal end. The coupler is configured to receive a cartridge and guide the cartridge to an engagement position with the needle. The coupler may be configured to shield the needle from physical damage. The coupler may be configured to aseptically seal the needle. The coupler may further include a glider movable within the coupler, wherein the glider holds the tip of the needle in a predetermined first position, and moves toward a second position wherein the glider provides clearance for the cartridge to engage with the needle. The glider may be configured to seal with at least one of the needle, the coupler, and the cartridge. The glider may be biased to the first position by a spring. At least a portion of the coupler may be removable from the syringe when the cartridge is disengaged.

Another example method of the present disclosure relates to a method for engaging a pre-filled cartridge with a dispensing device for transferring fluidic content therebetween. The dispensing device includes a reservoir, an administration device, and a coupler, wherein the reservoir holds a content, and the administration device receives and dispenses the content. The content may be a dispensable product or one or more constituents thereof. The coupler comprises a first end and a second end, wherein the second end movably receives a fitment to guide the fitment into engagement with the administration device to provide fluid communication between the cartridge and the dispensing device. The fitment communicates the content with the reservoir. The method includes receiving the cartridge in the coupler such that the cartridge and the dispensing device engage in fluid communication.

The method may include allowing fluid transfer between the cartridge and the reservoir. The method may include disengaging the cartridge from the dispensing device. The method may include at least partially removing at least a portion of the coupler from at least a portion of the administration device. The method may include disengaging the cartridge from the dispensing device, wherein at least a portion of the coupler is removed using the cartridge. The dispensing device and the coupler may be sterile, the cartridge may be sterile, and the dispensing device and the cartridge are aseptically engaged to form a sterile pre-filled dispensing system. The first end of the coupler may be configured to receive the administration device, and the method includes mounting the coupler on the dispensing device such that the administration device is received in the coupler. The method may include dispensing the content from the dispensing device after at least a portion of the coupler has been removed.

Another example method relates to a method for producing a prefillable container. The method includes forming a sealed cavity comprising at least a first compartment and at least a first filling compartment interconnected in fluid communication via a sealable first filling channel, piercing a wall of the filling compartment with a filling device and filling a constituent into the first compartment via the first filling channel, and sealing the channel when the filling step is completed.

The method may include removing a portion of the container that comprises the filling compartment. The cavity may include at least a second filling compartment interconnected in fluid communication with the first compartment, and the method further includes piercing the wall of the second filling compartment to allow gas to evacuate from the first compartment while the first compartment is filled with the constituent, and sealing the second channel when the filling is completed. The container may include a first pre-formed web wall joined with a second wall to define the sealed cavity. At least one wall of the container may be molded from plastic material. The container may be blow molded.

A further aspect of the present disclosure relates to a cartridge for use with a beneficial agent delivery device having a fillable reservoir. The cartridge includes a package including at least a first compartment, wherein the first compartment includes a first wall having a pre-formed peelable layer.

The peelable layer may include a planar area along a peripheral edge of the compartment for joining the peelable layer to the first wall. The first wall may be pre-formed to define a cavity, and the pre-formed peelable layer is configured to contain the cavity. The peelable layer may be a portion of the first wall construction.

Another aspect relates to a dispensing package that includes first and second web walls, first and second compartments, a frangible seal, and a dispensing port. The first web wall and a second web wall are joined along peripheral edges to define at least a portion of a compartment boundary. The first compartment contains at least a first constituent of a dispensable product. The second compartment contains at least a second constituent of a dispensable product. The frangible seal is positioned between the first and second compartments, which when opened allows the first and second constituents to merge. The dispensing port is opened in at least the first web wall. The frangible seal segregates the first and second compartments from the dispensing port. When the frangible seal is ruptured, fluid communication is established between the first and second constituents and the dispensing port. The first and second compartments may be formed in the second web wall.

Another aspect relates to a cap for an administration device of a delivery device. The cap includes a first compartment configured to receive the administration device, a second compartment, and a barrier forming a fluid tight seal between the first and the second compartment.

The first compartment may include a proximal end configured to communicate with at least one of the delivery device and the administration device. The second compartment may interface in communication with a fluid passageway. The second compartment may be configured to receive the distal portion of the administration device. The barrier may be configured to tightly seal around an area of the administration device between the proximal end and a distal end of the administration device. The cap may include an adapter in communication with the second compartment for communicating with a pre-filled package. The adapter may be configured to communicate with a fitment of the pre-filled package. The cap may include a fluid passageway and a closure disposed in the fluid passageway and configured to separate a distal end and a proximal end of the fluid passageway until opened. The proximal end may be configured to communicate with the administration device via a coupler. The cap may be configured to seal to the administration portion. The cap may be configured to provide protection to the administration device. The cap may include a backing to support a pre-filled package.

Another aspect of the present disclosure relates to a package that includes first and second web walls and a fitment. The first web wall and second web wall are joined at a joint along peripheral edges to at least partially define a compartment. At least one of the first and the second web walls is pre-formed to define a cavity in the compartment. At least a first portion of the joint provides a rupturable seal, which when ruptured provides fluid communication with the fitment, and at least a second portion of the joint provides a permanent seal.

The applications of the present invention are not limited to drug delivery, which is provided herein by way of example. The teachings described herein can be applied to dispensing devices in other areas such as, for example, glue dispensing, chemicals dispensing, etc. The present disclosure provides various configurations for accomplishing this.

BRIEF DESCRIPTION OF THE DRAWINGS

FIGS. 1a to 1f illustrate an injector cartridge assembly with a blister package associated with its cap, which can be employed to various configurations.

FIGS. 25a to 25c illustrate a cartridge comprising a coupler containing an injection needle.

DETAILED DESCRIPTION

Figures 2A, 2B:
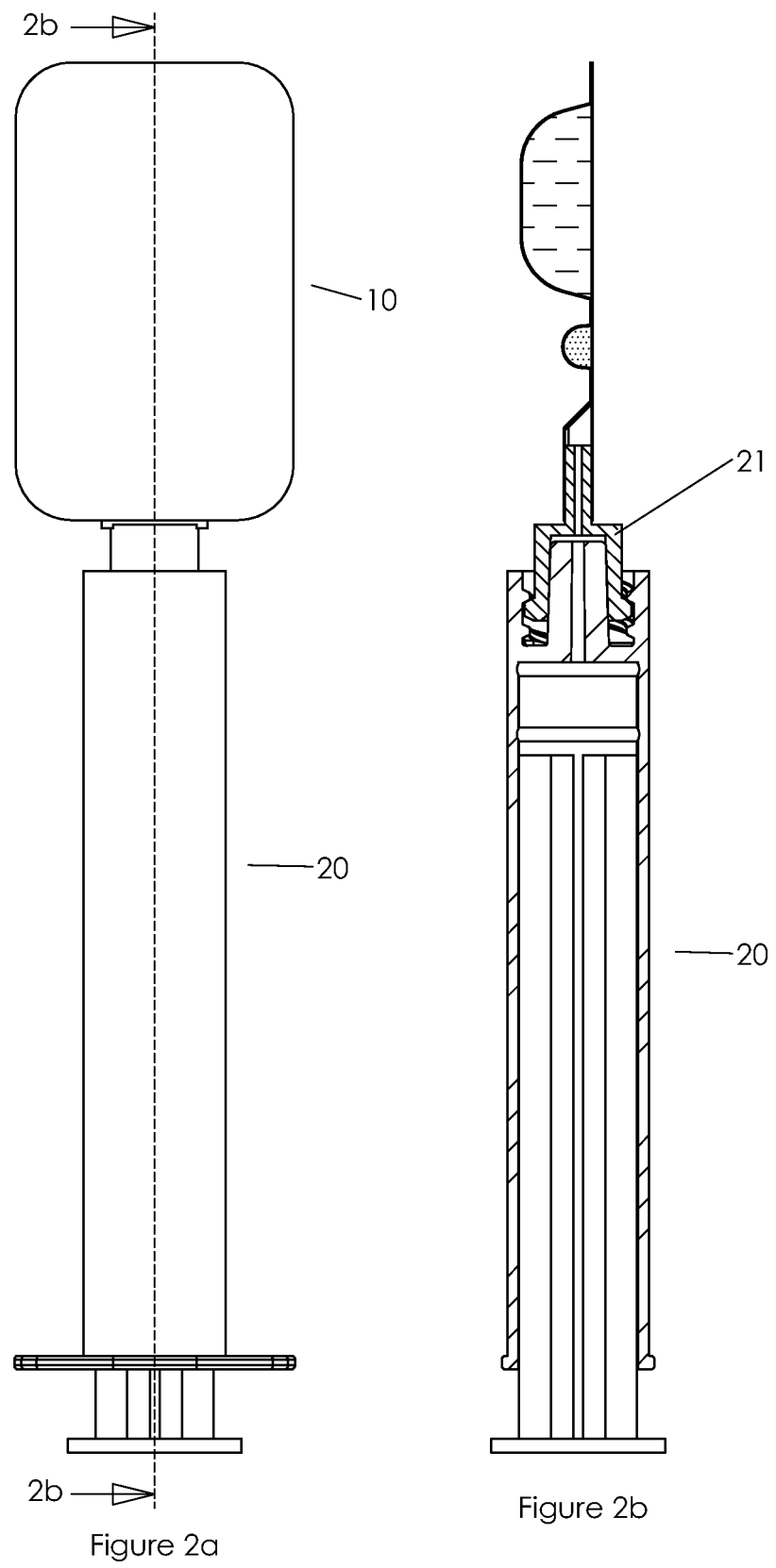
FIGS. 2a and 2b illustrate a syringe assembly with a blister package associated with its cap, which can be employed to various configurations.

FIG. 1a shows an arrangement of an injector 11 and a cartridge 10. FIG. 1b illustrates a section view of the injector assembly 11 and the cartridge 10. The injector 11 comprises a body 13 in the form of a tubular shaped barrel and a piston 14 disposed in the body. The piston 14 is movable along the axis of the body between a forward, empty state, and a retracted, filled state. The piston 14 further comprises an O-ring seal 14', providing a fluid-tight seal between the body 13 and the piston 14, and defining a dispenser reservoir or a reservoir in front of the piston for receiving an injectable dose. The reservoir is shown at the emptied state, wherein the piston 14 is advanced to the forward most position in the body 13. A jet nozzle 17, at the front of the body 13, is configured to hypodermically deliver a dose to a subject in a needle-free jet injection fashion when the piston 14 is advanced in the body 13 to deplete the reservoir volume. Prior to injection, the jet nozzle 17 serves as a port for filling a fluid dose from the cartridge 10 to the reservoir of the injector 11.

The cartridge 10 comprises a package comprising a first thin wall 18', pre-formed to establish two cavities; and a second thin wall 18'' which seals against the first thin wall 18' to define a first sealed compartment 15 and a second sealed compartment 16. A fitment 12 is disposed on the package 10', joined to the package 10' between the first wall 18' and the second wall 18". The fitment 12 is structured to engage with the front of the injector body 13. A first frangible seal section 19', separates between the first compartment 15 and the second compartment 16, and is peelable by a defined threshold force to allow fluid the content of the first compartment 15 and the second compartment 16 to merge. A second frangible seal 19" separates between the second compartment 16 and the fitment 12, and is peelable (rupturable) at a defined threshold peeling force. The second frangible seal defines a closure segregating the first compartment 15 from the fitment 12 until opened. The first and second walls 18', 18" may be made from a type of film or foil (together referred to as "web", webbing, or "web material") including extruded web, blown web, cast web, multilayer web, laminated web, coated web, webs including metalicized layers such as aluminum layer, webs including metal oxide layers such as alumina or silica, and webs including high barrier layer including Cyclic Olefin Polymer (COP), Cyclic Olefin Copolymer (COC), polychlorotrifluoroethylene (PCTFE), or Ethylene Vinyl Alcohol (EVOH). The inner adhesive layer of the web material may be made from Olefin ionomers, Ethylene-vinyl acetate (EVA), or other materials.

In some arrangements, the web comprises an inner adhesive layer that has a controllable peeling force such that designated areas of the circumferential seal around the compartment would have lower peeling force than others, thus limiting the areas that will be ruptured when a threshold peeling force is applied to the seal area between the first wall 18' and the second wall 18". One such adhesive layer is the ionomer brand EZ Peel® (Bemis, Neenah, Wis.) which produces a peelable seal at a sealing temperature of 130° C., and a permanent non-peelable seal at a sealing temperature of 170° C., thus allowing improved control of the sealing properties by performing a two-stage welding process at different temperatures. The peelable and non-peelable seals may be thermal seals having thermally sealed or thermally welded portions.

In some arrangements, the peeling force of the seal between the first wall 18' and the second wall 18" is controlled in different areas of the seal by applying a registered adhesive pattern of one or more adhesive types. In one arrangement, at least two adhesive types with different peeling strength are registered to define permanent sealing areas and peelable sealing areas. The fitment 12 may be made from an olefin polymer that will have good adhesion to the inner layer of the web, such as Polyethylene (PE). In some arrangements the fitment is attached to the outer side of one of the first wall 18' or the second wall 18", and a through hole in the web communicates the content of the cartridge 10 and the fitment 12. In this arrangement, the fitment material should be compatible for attachment to the web's outer layer material. The first and second compartments 15, 16 may contain various substances. In one embodiment, the first compartment 15 contains a first beneficial agent, or a constituent of such, in a diluent format, and the second compartment 16 contains a second beneficial agent, or a constituent of such, in dry format, and the content of the two compartments needs to be mixed to form a dispensable product dose. In one embodiment, the first compartment 15 contains a dilutant such as saline or water for injection, and the second compartment contains a vaccine in dry powder format.

The content or the constituents in the first compartment 15 and the second compartment 16 may be in various forms including liquid, frozen liquid, gel, paste, slurry, solid, granules, pellets, micro-pellets, spheres, micro-spheres, flowable powder, compressed powder, a cake, a lyophilized cake, or other forms of solid matter known in the art. When the first compartment contains a fluidic material, the first frangible seal 19' may be separated by depressing the first compartment 15 and pressurizing the content, thereby applying force to the first frangible seal 19' and peeling apart the seal, creating a joined compartment between the first compartment 15 and the second compartment 16, and allowing the content of the two compartments to mix. The second frangible seal 19" may be ruptured by depressing the joined compartment and pressurizing its content thereby causing a peeling force to the second frangible seal 19". The wall of the package 10' may be extended to provide a printable, or otherwise markable, surface, including graphics, text, barcode or other optical machine-readable representation of data (including RFID circuit), which shows data about the content of the cartridge, operation instructions, warnings, etc.

FIG. 1c shows the cartridge 10 mounted onto the injector 11. The fitment 12 is engaged with the front end of injector body 13, preferably creating an aseptic zone within the fitment area. A passageway of fitment 12 and the nozzle 17 are in fluid communication. For parenteral hypodermic drug delivery applications, all of the areas of the device that come in contact with the deliverable substances and the areas that will come in contact with the body of the subject are preferably maintained sterile or uncontaminated until the time of use. In the arrangement of FIG. 1c, the aseptic engagement of the injector 11 and the cartridge 10 maintains the sterility to that area. The sterility of the inner side of the barrel 13 may be maintained through an aseptic barrier at the back end of the body 13, a local overwrap of portions of the back of the body 13 and the piston 14, or a sterile overwrap to the entire device. In some arrangements the injector 11 and the cartridge 10 are provided separately, similar to the configuration shown in FIG. 1b with the addition that aseptic covers would be sealing the front area of the injector body 13 and the fitment 12.

The sterility of the fitment 12 may be achieved with a lead or a cap protecting the port area. A foil lead may be heat-sealed to the circumference of the vertical walls around the port. In one embodiment, the cartridge 10 is stored in a sterile overwrap. In some arrangements, wherein at least one of the substances is in dry format, it may be advantageous to include a drying agent such as a desiccant capsule, pellets, or gel in the sterile overwrap to avoid moisture from migrating to the dry compartment across the wall of web (i.e. the first wall 18'). In one embodiment, the drying substance may be integrated in the web. This arrangement is sometime referred to as scavenger web. The sterility of the front end of the body 13 in the arrangement of FIG. 1b can be achieved in various ways, including a tight cap, a thermally sealed foil around the nozzle 17 area, and by packaging the entire injector in a sterile overwrap. The arrangement of FIG. 1c may therefore be advantageous to reduce the measures that need to be taken to maintain sterility of the product.

Referring now to FIG. 1d, the arrangement of FIG. 1c is shown after the first and second frangible seals 19', 19" (see FIG. 1c) have been ruptured, and a joined compartment 16' is formed in fluid communication with the passageway of fitment 12.

FIG. 1e shows the arrangement of the previous FIG. 1d when the piston 14 is retracted from the body 13, thereby causing the fluid from the joined compartment 16' to flow into the unitary reservoir 13' in the injector 11.

FIG. 1f shows the arrangement of the previous FIG. 1e wherein the piston 14 is in a fully retracted state. The joined compartment 16' is fully depleted and its content is fully transferred to the reservoir 13' of injector 11. The cartridge 10 is removed and the injector 11, which is now loaded with the deliverable product dose, is ready to use. Where the arrangement is such that the cartridge 10 is joined with the injector 11 at the factory, the front portion of the injector is being maintained sterile until this point when the fitment 12 is removed. This arrangement may be advantageous compared to commercially available products wherein the injector's application surface is exposed to a non-sterile field even before the injector filling step, thereby increasing contamination risk to the subject.

The arrangement of FIG. 1a-1f is showing an aseptic filling procedure of a jet injector cartridge. Without departing from the scope of the invention, similar arrangements are provided to fill other cartridges, dispensers, or drug delivery devices known in the art including, for example, intramuscular, subcutaneous, or intradermal injectors, and their cartridges, topical applicators and their cartridges and reservoirs, infusion pumps, micro-infusion pumps, metering pumps, non-metering pumps, infusers, micro-infusers, patch delivery devices, and their cartridges and reservoirs, infusion containers including infusion bags and infusion bottles, oral, ocular, or ear dispensers and their cartridges and reservoirs, glue dispensers, and other dispensers, delivery device and applicators for various form of use and purpose.

FIG. 2 illustrates an arrangement of a pre-filled mixing cartridge 10 and a regular syringe 20. The figure provides a section line of the section view of FIG. 2b. Referring to FIG. 2b, the cartridge 10 comprises a fitment terminating 21 with a Luer Lock female connector, coupled with a Luer Lock male connector of the syringe 20, and forming a fluid-tight connection between the cartridge 10 and the syringe 20. The fluid may be transferred from the cartridge 10 to the syringe 20 in the same fashion as with the injector of FIG. 1. The Syringe tip will remain in an aseptic environment until the time of use where the cartridge 10 will be removed. This arrangement may be advantageous compared to commercial products where the syringe tip or the tip of a needle of a syringe are exposed to a non-sterile field prior to the filling step, which increases the risk of contamination to the subject. In one arrangement, the cartridge is maintained separate from the syringe until the time of use, when they are integrated through the Luer coupling. The cartridge and syringe may be aseptically integrated. To maintain the sterility of the syringe 20 and the cartridge 10, similar arrangements and measures may be taken as described above for the arrangement of FIG. 1b.

Figure 3A:
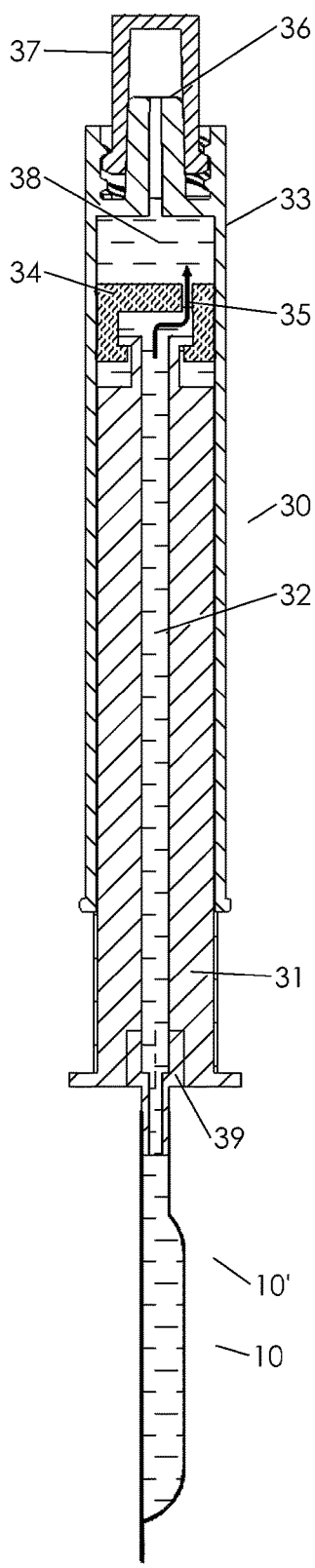
FIGS. 3a and 3b illustrate a pre-filled syringe assembly with a package associated with its piston's stem, and extending axially from it, which can be employed to various configurations.
Figure 3B:
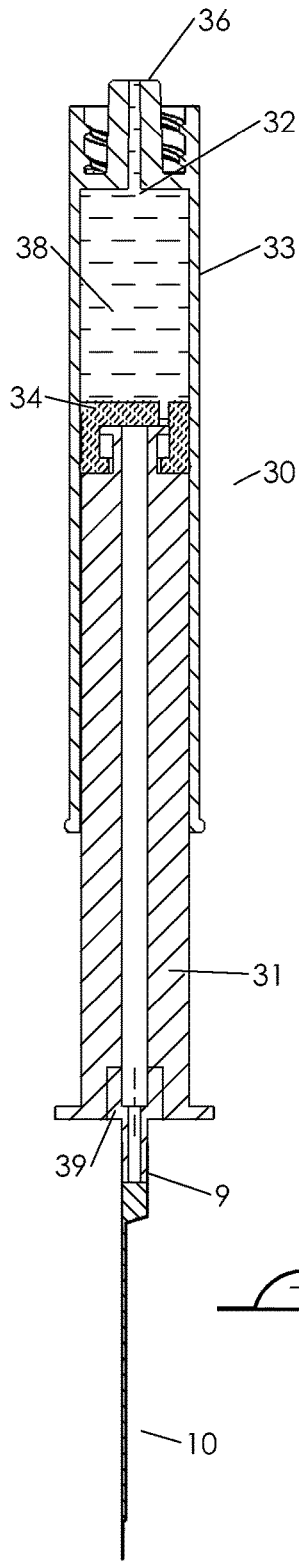

Referring to FIGS. 3a and 3b, another arrangement is provided wherein the cartridge 10 is connected to the back end of the piston 31 of a syringe 30 using a fitment 39. The piston 31 comprises a fluid passage 32 along its axis, communicating a cartridge port 9 and the reservoir 35 in the syringe body 33 (i.e. barrel). At the front end of the piston 31, a plunger 34 is arranged such that when the piston 31 is retracted, the friction of the plunger 34 with the barrel 33 causes the plunger 34 to slightly displace away from the piston 31, thereby opening a fluid path 35 (see arrow) allowing the content of the cartridge to transfer into the barrel 33. A cap 37 maintains an aseptic space around the syringe's dispensing tip 36. FIG. 3b illustrates the arrangement of FIG. 3a after the piston 31 has been retracted to the fully retracted position and is being advanced. The cartridge 10 is completely depleted of its content. The plunger 34 is replaced at the closer position to the piston 31 head thereby sealing the passageway 32, such that the content of the barrel 33 can only advance to the syringe tip 36 when the piston 31 is advanced.

Unlike commercial syringes where the dispensing tip or a needle associated with it are exposed to a non-sterile field prior to the filling process, in the current configuration the cap is removed from syringe tip 36 just prior to use and only after the filling process. The cartridge may be coupled with the syringe by various means known in the art including, for example, Luer connector, barb connector, press fit connector, a septum and spike arrangement, a coupling tube, or adhered to each other. In one arrangement, the cartridge is disposed inside a hollow space in the piston.

Figure 4:
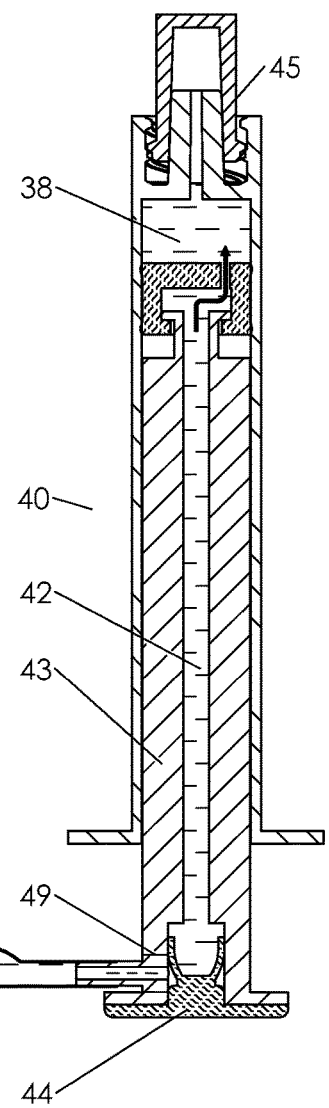
FIG. 4 illustrates a syringe assembly with a blister package associated with its stem, and extending laterally from it, which can be employed to various configurations.

Referring now to FIG. 4, an arrangement is illustrated where the cartridge 10 is connected to the back end of the piston 43 using a fitment 49 and extending in a lateral direction from piston 43. A valve 44 is disposed at the back end of a fluid passageway 42 allowing fluid to transfer from the cartridge 10 to the barrel 40 and fill reservoir 35, but prevents fluid from flowing in the opposite direction, thus causing the entire dose to flow only to the dispensing tip 45 when the piston is advanced. Valve 44 may be referred to as an isolation valve and may operate to separate or isolate the fill reservoir 35 and barrel 40 from the cartridge 10. In one arrangement the valve 44 also allows air into the flow passageway 42 after the cartridge 10 is emptied, thus advancing the fluid from the passageway to the barrel. In one embodiment, a dedicated aseptic compartment allows air or water into the fluid passageway 42 after the beneficial agent in the cartridge is emptied from the beneficial agent to wash the passageway from the residual beneficial agent. In one arrangement the water or air compartment is part of the cartridge 10 assembly. Other devices or structures may be used to seal the passageway 42 beside the valve 44. The passageway 42 may be hermetically sealed. The passageway may be sealed to prevent backflow of fluid into the water or air compartment.

In FIGS. 4a, 4b, and 5, the piston 43 serves as a coupler between the cartridge 10 and the reservoir. Generally these arrangements disclose a cartridge 10 for use with a beneficial agent delivery device having a fillable reservoir. The cartridge includes a package 10' that includes at least a first compartment 15 containing at least one constituent of a beneficial agent, a fitment disposed on the package, and a coupler. The coupler is joined to the fitment for interfacing the package in fluid communication with the fillable reservoir. The coupler comprises a closure interrupting the fluid communication until opened. The coupler may be aseptically sealed. The coupler is configured to communicate with a reservoir of an administration device. The coupler comprises a valve controlling the flow into and out of the package. The coupler comprises at least a portion of a syringe piston. The coupler and fitment are joined by at least one of a press-fit, a gluide-fit a thermal weld, and a bonding. The cartridge comprises a package that includes at least one flexible wall that is pre-formed to define at least a portion of the first compartment.

Figure 5A:
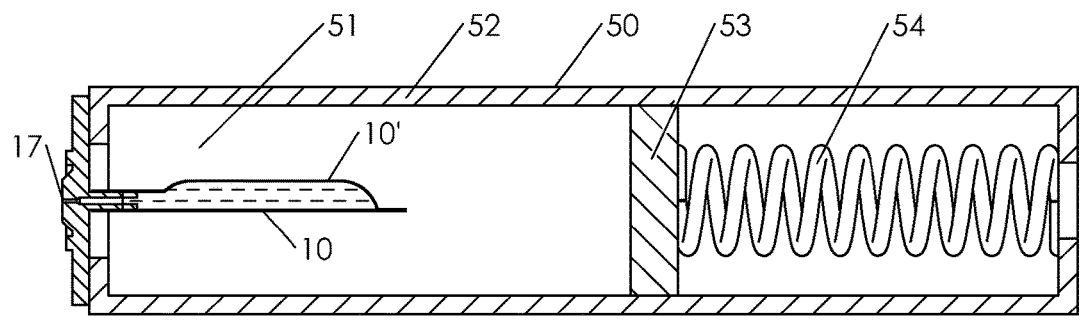
FIGS. 5a and 5b illustrate a pre-filled cartridge in a spring powered needle-free auto injector.

FIG. 5a illustrates a jet injector comprising a cartridge 10 comprising a package 10' disposed in a pressure chamber 51 in the injector body 52. The cartridge 10 comprises a needle-free jet nozzle 17 disposed on the package and associated with the front end of the injector body. A piston 53 is disposed in the body 52 and is detained in its pre-use position by a detaining mechanism (not shown), and is biased forward to pressurize the gas in the pressure chamber 51. In one arrangement, the cartridge 10 comprises more than one compartment prior to use containing more than one constituent, and those constituents are manually mixed by removing the cartridge 10 and following a similar procedure as described in FIG. 1; then replacing the cartridge 10 in the body 52.

Figure 5B:
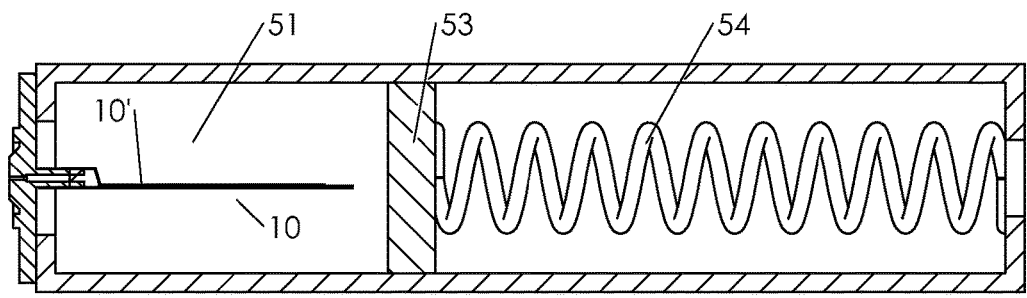

FIG. 5*b* shows the injector 50 after the piston 53 has been released from the detent mechanism and has been forced forward by spring 54 and pressurized the gas in the pressure chamber 51, thereby causing the cartridge walls to collapse and express the content of the cartridge 10 through nozzle 17. The nozzle 17 may be protected by an aseptic cap or adhered foil until the time of use.

Figure 6:
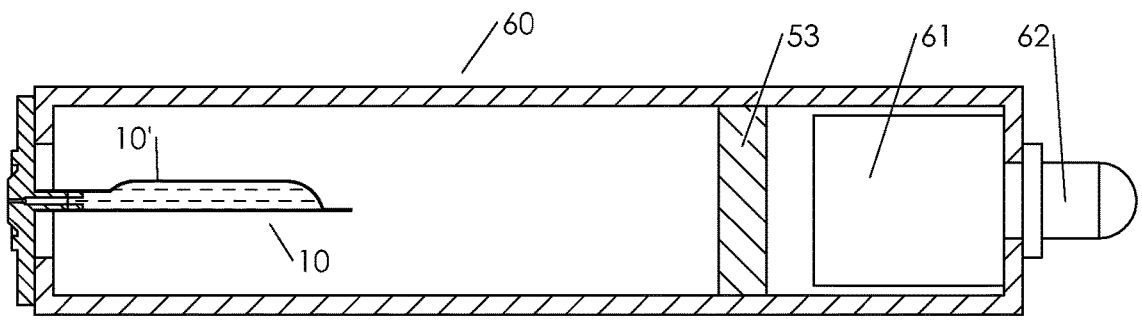
FIG. 6 illustrates a pre-filled cartridge in a pyrotechnically powered needle-free auto injector.

FIG. 6 shows a similar injector arrangement 60 to that of FIG. 5 with the exception that the piston is biased forward by pressurized gas that is generated by a pyrotechnic module 61 which is activated by manual switch 62.

Figure 7:
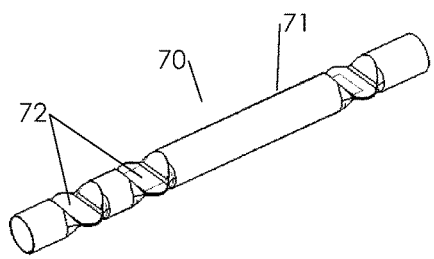
FIG. 7 illustrates a cartridge made from an extruded tube.

FIG. 7 shows a package 70 made from a tube section 71 that is pinched and heat sealed 72 across the tube section 71 in a number of locations 72 along the tube section 71 to form at least one compartment comprising a beneficial agent or a constituent of such. In one configuration of the package 70, the seals at the pinching locations 72 are frangible seals made such that they will peel apart under the presence of threshold pressure or force. The tube section 71 may be made by extrusion, injection molding, blow molding, rolling a flat foil and sealing the seam, or other manufacturing methods known in the art. In one arrangement, the tube section 71 comprises a number of layers, wherein the inner layer is a heat sealing material and at least a second layer provides improved barrier properties to reduce transfer of certain gases or moisture across the tube wall. In one arrangement, the tube is co-extruded. In one arrangement, at least one first layer of the tube wall is made from a rolled sheet of plastic, metal, or metal oxide, and at least one second layer is extruded over the rolled first layer. The wall of the package may be extended to provide a printable, or otherwise markable, surface, including graphics, text, barcode or other optical machine-readable representation of data (including RFID circuit), which shows data about the content of the cartridge, operation instructions, warnings, etc.

Figure 8:
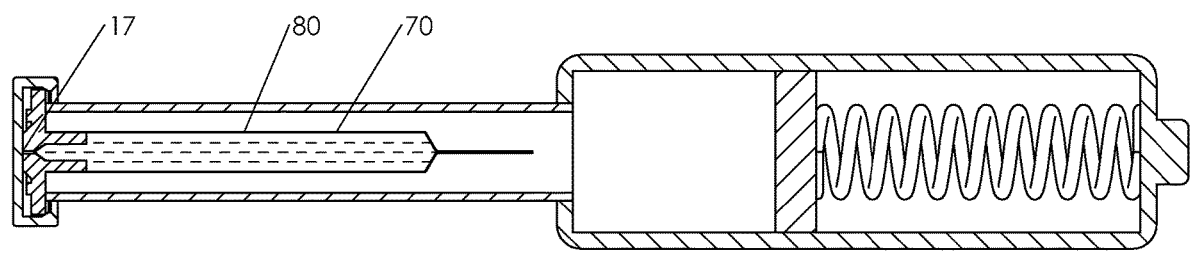
FIG. 8 illustrates a cartridge made from extruded tube and loaded in a needle-free auto-injector.

FIG. 8 shows a needle free jet injector arrangement similar to the arrangement presented in FIG. 5, with the exception that the cartridge 80 comprises a package made from a tube section similar to the package shown in FIG. 7, and a jet nozzle 17 is attached at its front end.

Figure 9A:
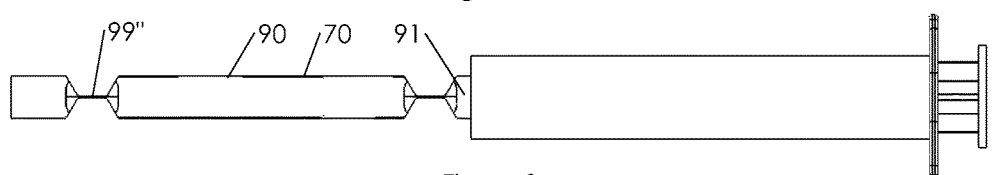
FIG. 9a illustrates a cartridge made from extruded tube and mounted onto a syringe.

FIG. 9*a* shows a syringe and cartridge assembly similar to the arrangement presented in FIG. 3, with the exception that the cartridge 90 comprises a package 70 made from a tube section 93 that is pinched and sealed across in first and second seals 99', 99" to form a compartment. First seal 99' is a frangible seal that would rupture when the cartridge is compressed and the content is pressurized to allow fluid communication between the syringe and the cartridge. A female Luer lock connector 91 is attached at an end of the cartridge. In some arrangements, the cartridge 90 may be maintained separate from the syringe until the time of use. Sterility of the product and the device may be accomplished in similar fashion and measures as described in FIGS. 1 to 3 above. The tube wall may incorporate a single layer or multi-layers and may incorporate, for example, a high barrier PCTFE layer, an aluminum layer, a COC layer, and a peelable adhesive layer.

Figure 9B:
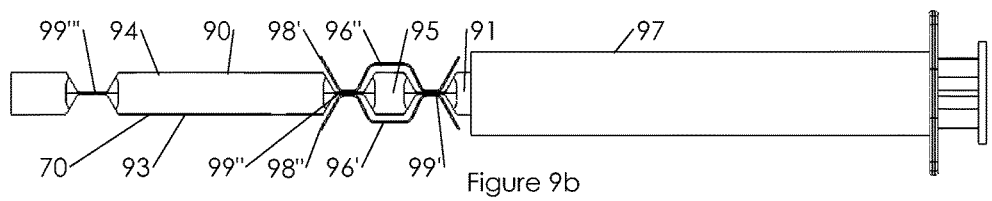
FIG. 9b illustrates a cartridge made from extruded tube comprising a peelable protective foil and mounted on a syringe.

FIG. 9*b* shows a further arrangement of a cartridge 90 comprising a package 70 made from tube wherein a first seal 99' and a second seal 99" define a first compartment 95 holding a first substance. A third seal 99''' defines a second compartment 94 holding a second substance. The second seal 99" is rupturable upon pressurizing either or both of the first compartment 95 and the second compartment 94 to allow the first substance and the second substance to merge. The first seal is rupturable to establish fluid communication between the cartridge and a syringe 97. The cartridge further comprises peelable high-barrier shells 96' and 96" sealed to each other and across the first and second seals 99', 99". The peelable barrier shells 96' and 96" enhance the barrier between the cartridge surrounding and the first compartment 95. This arrangement may be particularly advantageous where the barrier properties of the tube section 93 are insufficient to protect the first compartment 95 from moisture, oxygen or light transmission.

The tube material may preferably be transparent to allow visual inspection of the contents, which generally compromise some of the barrier properties. The peelable barrier shells 96', 96" may include a high barrier aluminum layer that prevent visual inspection of the cartridge contents, and hence the need to peel the shells for inspection. A first tab 98' and a second tab 98" are provided as extensions to the first and second peelable barrier shells 96' and 96", respectively, to facilitate the peeling of the shells with the fingers. The peelable barrier shells may be pre-formed to accommodate the shape of the first compartment 95. At least one of the peelable barrier shells 96' and 96" may be extended to form a barrier shell to the second compartment 94. At least one of the peelable barrier shells may be extended to provide a printable, or otherwise markable, surface, including graphics, text, barcode or other optical machine-readable representation of data (including RFID circuit), which shows data about the content of the cartridge, operation instructions, warnings, etc. The peelable barrier shells may be made from a single or multi-layer film or foil (together "web") and may include a pressure sensitive adhesive, electrostatic adhesive or temperature sensitive adhesive to form the peelable seal.

Figure 10A:
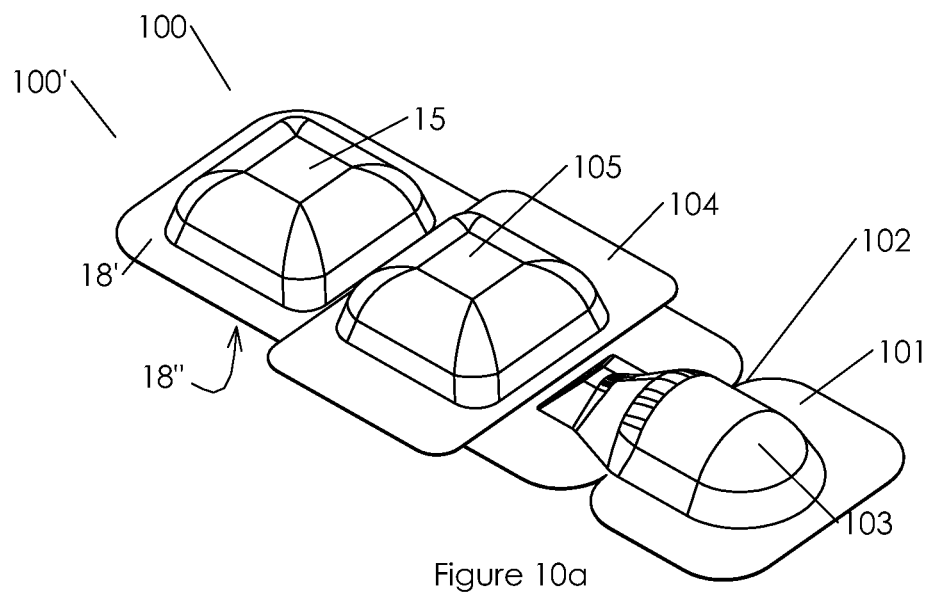
FIGS. 10a to 10e illustrate a cartridge with a peelable portion of the formed-wall and an extended wall portion forming an aseptic compartment around the dispensing port, and a number of operation steps.

FIG. 10*a* shows another preferred cartridge arrangement 100 comprising a package 100' in which the second compartment 16 comprises a peelable layer 104. For various applications it is desired to have at least a portion of the package made from a clear material, for instance, in an application where it is desired to visually (or by optical instrumentation) inspect the content of one or more compartments, or the merged compartment after combining the content of two or more compartments. However, clear materials typically have higher moisture vapor transmission rate (MVTR) than foils, which are opaque, thereby providing lower barrier between the compartment(s) and the surrounding of the package. Some products are extremely sensitive to moisture, such as some vaccines in dry format with which potency may be compromised with relative humidity levels higher than 2% or 3%. Visual inspection of the vaccine powder is important prior to use to ensure that the product has not been tampered with, and after mixing to inspect complete dissolution of the vaccine powder with the dilutant.

In one arrangement, the cartridge 100 is stored in a desiccant containing overwrap, thereby keeping a dry environment around the package 101'. In one arrangement, the overwrap material is of the type known in the industry as "scavenger film" in which a desiccant substance is embedded in the composition of the web material. In FIG. 10*a*, the powder compartment of the package 100' comprises a peelable high-barrier pre-formed layer 104 that is opaque, or has limited or no optical transparency. In some arrangements, the peelable layer may provide a barrier from light. High barrier clear materials are typically more costly than low barrier clear materials. In some arrangements, the localized, peelable layer 104 is made from high barrier clear material such as a film containing Aclar (Honeywell), while the larger, formed first wall 18' of the package 100 is made from a low barrier material to reduce manufacturing costs. The peelable layer 104 may provide other desired properties that the first wall 18' lacks. The peelable layer 104 may be part of the composition of the material of the first wall 18'. The peelable layer 104 may be made from a separate web of the first wall 18', and in one manufacturing arrangement, the two webs are formed together. In some arrangements, where the first wall 18' is a thermoformable film, and the peelable layer 104 is a cold-formed foil, the forming process may involve a step combining cold forming and thermoforming.

In some arrangements, a cavity 105 in the peelable layer 104 is formed separate from the first wall 18' and is subsequently attached to the package in a sealed fashion. Attaching the peelable layer 104 to the package may be achieved by one of the means known in the art including, for example, an adhesive, a glue, pressure sensitive adhesive, heat stake welding, ultrasonic welding, etc. In one arrangement, the peelable layer 104 is sealed to the first wall 18' via a die-cut adhesive sheet. The die-cut adhesive may be adhered to the first wall 18', and at a subsequent stage the peelable layer 104 is attached to the die-cut adhesive. Alternatively, the die-cut adhesive may be adhered to the peelable layer 104, and at a subsequent stage the first wall 18' is attached to the die-cut adhesive. The peelable layer 104 may comprise an aluminum lamination or aluminum coating.

Figure 10B:
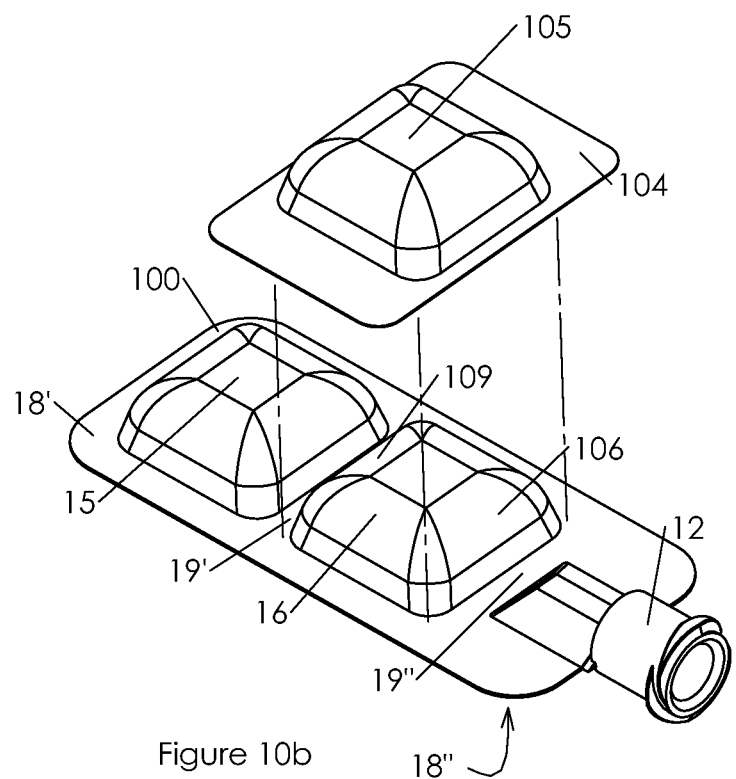

The package arrangement 100 further comprises a fitment compartment 103 maintaining the dispensing port in an aseptic enclosure until the time of use. The fitment compartment 103 is formed in an extension 101 of the web materials of the package 100. A tear-off notch 102 provides for an easy removal of extension portion 101 to expose the fitment 12. FIG. 10*b* shows the cartridge arrangement 100 after the peelable layer 104 has been removed, allowing for visual inspection of the content of the second compartment through the clear first wall 18'. In addition, extension 101 has been removed, exposing a fitment 12 (e.g., dispensing port) in the form of a female Luer Lock connector. In some procedures it will be desired to merge the first and second compartments 15 and 16 prior to removing extension 101 to minimize the exposure of the dispensing port and reduce the risk of contamination. The second wall 18" of the package 100 is preferably made from high barrier material such as a laminated aluminum foil, SiOx laminate, AlOx laminate or other materials known in the art.

In some arrangements, the second compartment 16 is depressed to rupture the first frangible seal 19' between the first compartment 15 and the second compartment 16, to cause the two compartments to merge, and to rupture the second frangible seal 19" between the second compartment 16 (or the merged compartment 15+16). The pre-formed structure of the second compartment 16 allows controlling the rupture of each of the first and second frangible seals 19', 19" at a desired sequence and timing. The deep form of the second compartment 16 provides that when the second compartment 16 is depressed at its distal end 106, the strain in the area of the distal end 106 of the first wall 18' 106 is relaxed, thus limiting the peeling force exerted on the second frangible seal 19" and preventing it from rupturing. Further, the proximal area 109 of the first wall 18' opposite to the depression zone at the distal end 106, is strained, and the first frangible seal 19' is ruptured while the second frangible seal 19" remains intact.

At a subsequent step, the merged compartment (not shown) is pressed at its proximal area to exert sufficient peeling force on second frangible seal 19" causing it to rupture and establish fluid communication between the merged compartment and the dispensing port. In addition to, or as an alternative to, the aseptic dispensing port compartment 103, the port may be aseptically sealed with, for example, a plug (such as a male Luer Lock cap), a welded foil portion, a stopper (such as a rubber stopper), or by any other means known in the art. The second frangible seal may be avoided if other closure features are aseptically protecting the content and preventing the contents from spilling.

Figure 10C:
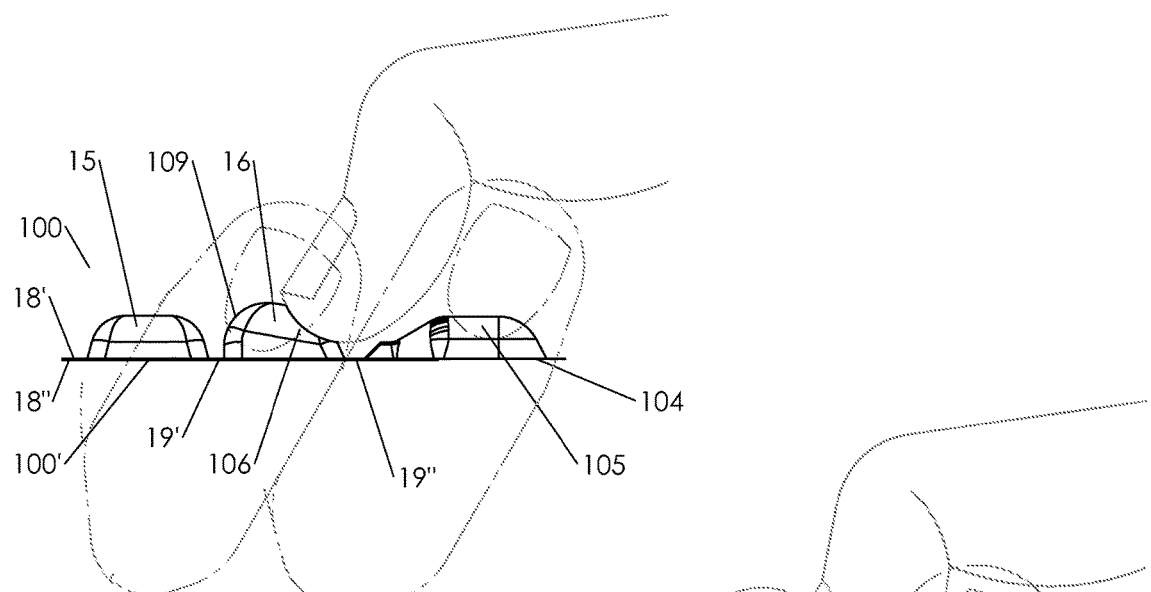
Figure 10D:
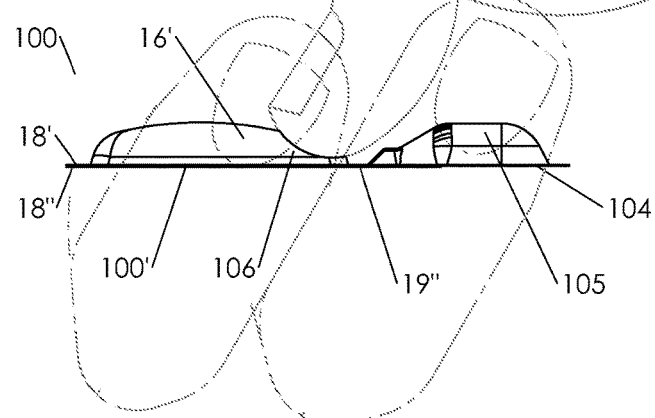
Figure 10E:
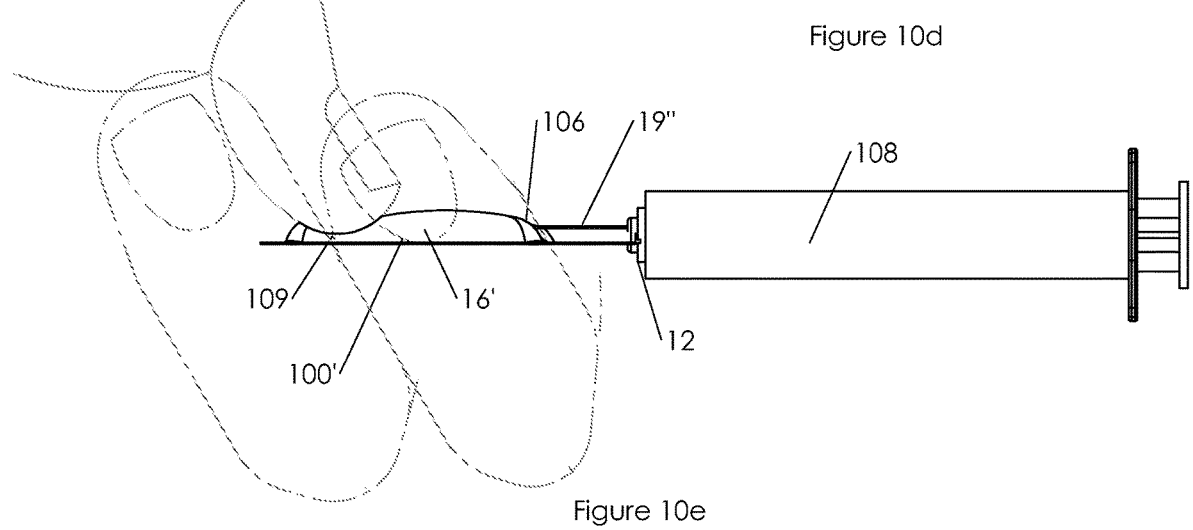

FIG. 10*c* to FIG. 10*e* show one method of operating the package 100' to achieve a controlled and sequenced rupture of the first and second frangible seals 19', 19" by direct operation of the thumb of the operator. The package 100' is resting in the palm of the operator on the index finger and the middle finger. In FIG. 10*c*, the second compartment 16 is depressed by placing a thumb on its distal end 106. As a result the first wall 18' at the proximal area 109 of the first compartment 15 is strained, thereby exerting peeling force to the first frangible seal 19'. At the same time, the depression of the thumb on the distal end 106 of the second compartment 16 prevent strains from that area of the first wall 18', resulting in the peeling force on the second frangible section 19" being eliminated or minimized. As a consequence (shown in FIG. 10*d*), the first compartment 15 and the second compartment 16 become joined compartment 16' while the second frangible seal 19" remains intact, thereby allowing the constituents of the two compartment to mix prior to communicating the dispensable product with the fitment (i.e. dispensing port). The configuration of FIG. 10*d* allows putting the cartridge aside, for example, in order to let the substances mix properly without exposure to contamination risks as the dispensing port is still sealed in the dispensing port compartment 103 and the joined compartment 16' is still not in communication with the dispensing port.

In FIG. 10*e* the dispensing port compartment has been tore off and the fitment or port 12 is engaged with a syringe 108. The joined compartment 16' is depressed with the thumb at its proximal area 109, causing the wall at the distal end 106 of the merged compartment 16' to strain and exert peeling force on the second frangible seal 19", and causing the second frangible seal 19" to rupture and establish fluid communication between the syringe 108 and the joined compartment 16' via the dispensing port 12. In other arrangements, the depression of the compartments 15, 16 is done by a compressing object such as a flat panel or a roller. This disclosure advantageously teaches a drug cartridge for filling an injector where the fluid communication between the cartridge and the injector is established only after the injector and the cartridge have been secured in a sealed tight fashion, limiting the exposure of the injectable product to a non-sterile field, and reducing the risk of product spillage. Typically with vials and ampoules the fluid communication is established during the integration of the injector and the cartridge by a spike penetrating a septum seal.

Figure 11:
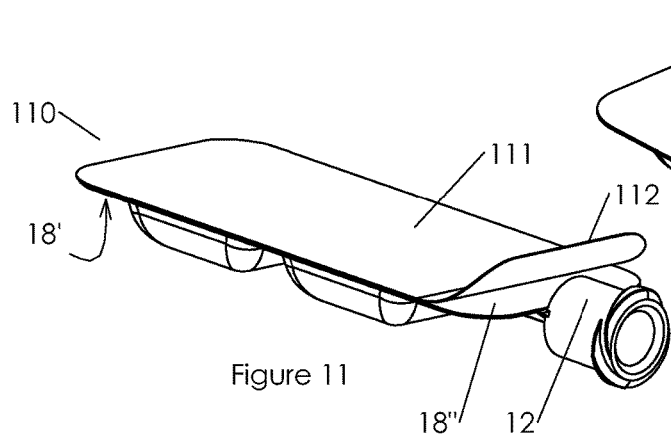
FIG. 11 illustrates a cartridge with a peelable portion of the flat wall.

FIG. 11 shows an arrangement where the second wall 18" of the package comprises a high-barrier peelable layer 111, providing enhanced moisture barrier to the substances in the compartments. The first wall 18' is preferably made from a cold formed aluminum laminate providing a high barrier to moisture and gases. A tab 112 provides an easier peel of the second wall 18". In some arrangements, the peelable layer 111 is attached to the second wall 18" by one of the means known in the art such as welding or adhesion. In one arrangement, the peelable layer 111 is a label with a pressure sensitive adhesive. In some arrangements, the pressure sensitive adhesive is selectively registered on desired areas of the label such that certain areas of the label are free from the pressure sensitive adhesive.

The peelable layer 111 preferably comprises an aluminum layer providing a high barrier to moisture and gases to the compartments of the package until it is being peeled off. In some arrangements, the peelable layer is part of the multilayer material composition of the web that makes the second wall 18". In some arrangements, the peelable layer 111 is removed from the entire second wall 18". In some arrangements, a scored or die-cut pattern defines the area of the peelable layer 111 that will be removed. In some arrangements, a section of the first wall 18' and the second wall 18" is scored or die-cut, providing a tab or a break-off tab that facilitates the removal of the peelable layer 111. The cartridge 110 may be readily attached to an injector, a drug delivery device, a reservoir of these or other systems, or it may comprise a closure that is removed prior to use. The peelable layer 111 may include printed (or otherwise marked) information and may be attached to a person, a device, the drug delivery device receiving the content of the cartridge 110 (such as a syringe), or a document after it has been peeled off from the cartridge 110, and used as a label presenting that information.

It is understood that other labels may be attached to the cartridge arrangements according to this disclosure. These other labels may include printed or otherwise marked information, machine readable information such as barcode or RFID circuit, and may be non-peelable or peelable, and further attached to other objects such as a person, a device, or a document. In some arrangements, an information-containing portion of the cartridge may be tearable or otherwise detachable from the rest of the cartridge in order to include or present this information elsewhere such as on a document, attached to a patient, or to a device.

Figure 12:
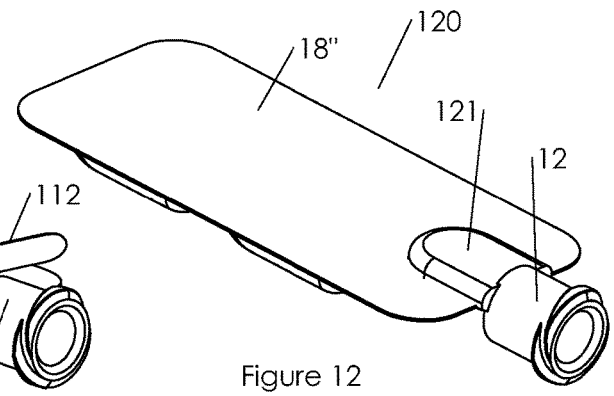
FIG. 12 illustrates a cartridge with a flanged dispensing port attached to the external side of the wall of the cartridge.

FIG. 12 shows an arrangement wherein the fitment (i.e. dispensing port) is attached to the external side of the second wall 18" via a flange 121. The flange comprises a conduit (not shown) aligned with an opening in the second wall 18" (not shown) which communicates the content of the package with the dispensing port. The fitment or port 12 is attached to the second wall 18" by one of the means known in the art such as heat welding or adhesion. The cartridge 120 may be readily attached to an injector, a drug delivery device, a reservoir of these or other systems, or may comprise a closure that is removed prior to use.

Figure 13:
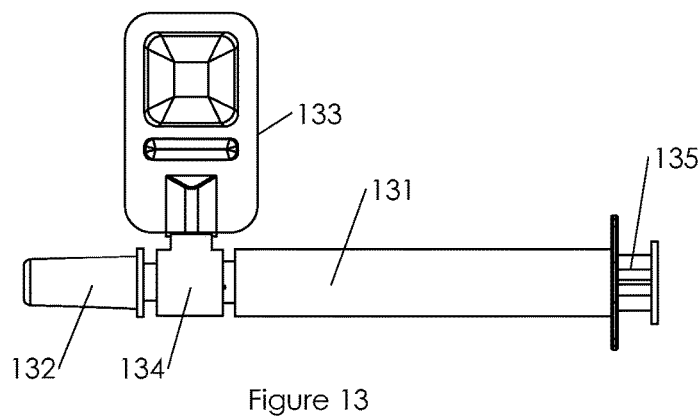
FIG. 13 illustrates a cartridge associated with a valved-coupler communicating to a syringe and a needle.

FIG. 13 shows an arrangement wherein the cartridge 133 is associated with a manifold 134 disposed between a syringe 131 and a needle (shown here covered by a needle shield 132). The manifold comprises a valve arrangement which, after the cartridge 133 has been activated, draws the content of the cartridge 133 into the syringe 131 when the syringe's piston is retracted and delivers the content of the syringe 131 to the needle when the piston is forwarded. In some arrangements, a manipulation of the manifold will cause disengagement of the cartridge from the manifold 134 when shifting from a dose drawing configuration to a dose injection configuration. U.S. Pat. No. 7,879,018 teaches a number of manifold arrangements for accomplishing the same and is incorporated herein in its entirety by this reference.

FIG. 13 illustrates the cartridge 133 joined to a 3-way coupler 134 disposed between a syringe 131 and administration device 132. In this arrangement, mixed constituents are transferred from the cartridge 133 to the syringe barrel 131 just prior to injection by retracting the syringe piston 135. The arrangement of FIG. 13 includes a pre-filled syringe wherein the piston is in an inward position prior to use, which allows for superior packaging density relative to regular prefilled syringes wherein the piston is in a retracted position during storage. The piston is advanced inwardly to dispense the dispensable product through the administration device 132.

A valve system may be disposed in the coupler 134 to restrict the flow from the cartridge 133 to the syringe's barrel (i.e. reservoir), and from the reservoir to the administration device. The valve system may include check valves that automatically control the flow with no need for operator intervention. In one arrangement, the cartridge is moved relative to the coupler to operate the valve system. This movement may be inward or outward linear motion, rotation, or a combination of those. In one arrangement, certain movement of the cartridge relative to the coupler disconnects at least a portion of the cartridge from the coupler. This disconnect may be advantageous after transferring the dose to the reservoir of the syringe to "clean" the syringe configuration for injection. The administration device 132 may include a needle, and a needle safety feature and a syringe disabling feature may be incorporated with this arrangement. The needle may be configured as an injection needle.

US Pat. Publication No. 2009/0221962 teaches a retractable syringe and plunger. The syringe has a barrel, a retractable needle mount to which is mounted or is mountable a needle, and a plunger. The plunger includes an initially compressed spring, a means for engaging the retractable needle mount, an integrally formed plunger seal, and a removable controlling means for facilitating control of the rate of retraction of the needle mount when engaged with the plunger. The needle mount is held in the barrel by a holding means that prevents inadvertent retraction of the needle mount when the plunger is withdrawn to fill the syringe. The holding means comprises a plurality of clips that may be integrally formed with the barrel or may be present on a cap mounted to the barrel. An ejector means is also provided, wherein plunger depression can urge the ejector means to release the needle from the holding means and thereby allow retraction of the needle mount following decompression of the spring. In one arrangement of the present disclosure, the cartridge is associated with a syringe with a retractable needle mount such as the one taught by US Pat. Publication No. 2009/0221962. The pre-filled syringe may be configured to operate by at least one of an auto injector, a syringe pump, a controlled actuator, a mechanical ram or pressure.

Figure 14:
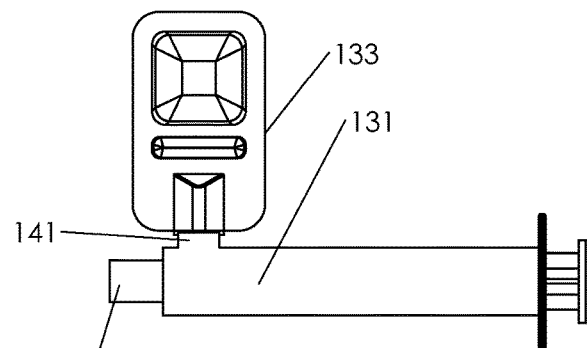
FIG. 14 illustrates a cartridge associated with the distal end of a syringe barrel.

FIG. 14 shows a cartridge 133 comprising a valved port 141 connected with a syringe 131. For the step of loading the syringe barrel with the dispensable product from the cartridge 133, the Luer cap 142 is maintained in place. After merging the compartments of the cartridge 133 and popping the closure between the merged compartment and the dispensing or valved port 141, the valved port 141 provides that when the syringe's piston 135 is retracted, the dispensable product will flow from the cartridge 133 to the syringe barrel (i.e. reservoir). When the piston is advanced, the dispensable product is urged from the reservoir to the syringe tip and will not return to the cartridge 133. In one arrangement, the valved port comprises a check valve allowing fluid to flow out of the cartridge 133 and prevent reversed flow into the cartridge 133. In one arrangement, the valved port is manually operated, for instance, by rotation, axial movement, or a combination of these, to switch between an open state and a closed state.

In one aspect of this arrangement, there is a cartridge for use with a beneficial agent delivery device having a fillable reservoir. The cartridge includes a package that includes at least a first compartment containing at least one constituent of a beneficial agent, a fitment disposed on the package, and a coupler joined to the delivery device for interfacing the fitment in fluid communication with the fillable reservoir. The fitment being disposed on the package may include a releasable connection, a permanent connection, a connection that provides flow communication, or various other mountings and connections.

The coupler includes at least one closure interrupting the fluid communication until opened. The coupler is aseptically sealed. The coupler is configured to communicate with an administration device. Various closures are possible. For example, the closure may comprise a membrane, a stopper, a valve, or other structure that provides a seal. The closure may be reusable and operate between open and closed positions. The closure may open when pierced or ruptured using a sharp object (e.g., needle) or using pressure. The coupler includes a valve controlling the flow into and out of the package, wherein the valve is operative by a relative motion between said coupler and at least one of said fitment and said delivery device. In some arrangements, at least a portion of the cartridge is detachable from the coupler. In some arrangements, at least a portion of the cartridge is detachable from the coupler after the reservoir has been at least partially filled with the beneficial agent.

The delivery device may be selected from a group consisting of a medical syringe, staked needle syringe, safety syringe, retractable needle syringe, auto-disabling syringe, auto-injector syringe, jet-injector syringe, intradermal syringe, subcutaneous syringe, intramuscular syringe, infusor, infusion pump, sustained release delivery system, and patch pump. The coupler may include at least a portion of a syringe barrel. The coupler and fitment may be joined by at least one of a press-fit, a gluide-fit, a thermal weld, and a bonding.

In some arrangements, the cartridge is removable either during manual operation or post manual operation. U.S. Pat. No. 7,879,018 teaches a number of manifold arrangements for accomplishing the same and is incorporated herein in its entirety by this reference. In some arrangements, the syringe 131 is valved such that no flow is allowed through the syringe's tip when the syringe's piston is retracted, and flow is allowed to flow out of the syringe's barrel when the piston is advanced. In some arrangements, the syringe's valve is a check valve. In some arrangements, the syringe's valve is manually operated. In some arrangements, the syringe's valve and the cartridge's valved port 141 are mechanically linked such that operating the cartridge valved port 141 to shut off operates the syringe's valve to open, or vice versa. The arrangement of FIG. 14 may be particularly advantageous wherein the dispensing tip has a construction that cannot accept a cartridge, for instance, where the dispensing tip incorporates a staked needle, a retractable needle, a needle stick prevention device, or other safety devices or mechanisms.

US Pat. Publication No. 2011/0015572 teaches a retractable syringe, plunger and releasable needle retaining assembly. The retractable syringe typically has a glass barrel and is pre-filled with fluid contents before use. The releasable needle retaining system comprises a retractable needle, a needle seal, a retaining member and an ejector member that is operable to release the retractable needle from the retaining member. The retaining member has a mating surface for mounting to a complementary mating surface of an interior wall of a syringe barrel. The plunger comprises a plunger outer, a plunger rod frangibly connected to a controlling member, a spring, and a unitary plunger seal capable of engaging the retractable needle. The plunger rod, plunger outer and the controlling member co-operate to releasably maintain the spring in an initially compressed state. After delivery of fluid contents of the syringe, the plunger forces the ejector member to release the retractable needle from the retaining member. Decompression of the spring at the end of depression of the plunger facilitates retraction of the retractable needle when engaged with the unitary plunger seal. Dual locking systems prevent re-use of the syringe after needle retraction. In one arrangement of the present disclosure, the cartridge 133 is associated with the barrel of a safety syringe such as the one disclosed in US Pat. Publication No. 2011/0015572, via a valved port 141 arrangement of FIG. 14.

Figure 15:
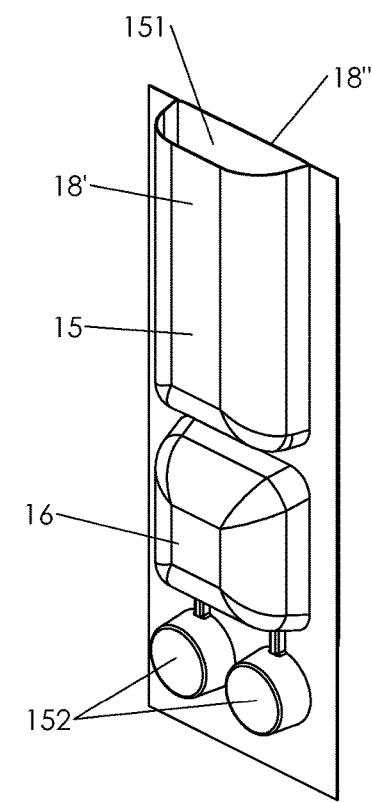
FIG. 15 illustrates a semi-finished cartridge ready for lyophilization of a beneficial agent.

Referring now to FIG. 15, in some arrangements it is desired to lyophilize (freeze dry) a substance directly in the first compartment 15. The first wall 18' is pre-formed and welded to the flat, second wall 18". The first compartment 15 has an open end 151 and is longer than the final, sealed dimensions of this compartment. The first compartment 15 is filled with a liquid substance. The cartridge is then placed in a freeze drier until the lyophilization process is completed, leaving a dry cake at the bottom of the first compartment 15. The compartment is then sealed to aseptically contain the lyophilized dose. The second compartment 16 may be filled and sealed prior to the lyophilization process or after it. The second compartment 16 may be hermetically sealed empty and then filled via fill wells 152 (see filling arrangement described with reference to FIGS. 20a-g).

The arrangement of FIG. 15 is also advantageous for filling a product or constituents thereof in a vertical position as shown in this figure. This arrangement may be particularly advantageous where there is a need for a filling device to reach into compartment 15 via opening 151. It is also advantageous where a product needs to flow or be dropped into compartment 15 with gravity. In some arrangements, the second compartment 16 is filled prior to filling the first compartment 15. In some arrangements, the second compartment 16 is filled after filling the first compartment 15. In other arrangements, the second compartment 16 is filled simultaneously with filling the first compartment 15.

Figure 16:
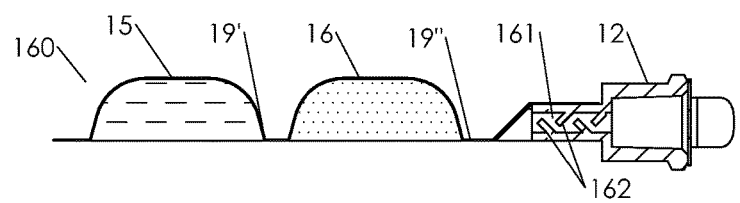
FIG. 16 illustrates a cartridge comprising a static mixer at its dispensing port facilitating the mixture of two constituents stored in the cartridge.

Referring to FIG. 16, a further arrangement of a cartridge 160 is shown comprising a first compartment 15 holding a first substance or constituent of a dispensable product, and a second compartment 16 holding a second substance or constituent of a dispensable product. The compartments are separated by a first frangible seal 19' that is rupturable to allow the first substance and the second substance to merge. The second compartment 16 is separated from a female Luer lock fitment 12 by a second frangible seal 19" that is rupturable to allow fluid communication between the cartridge and a dispensing device, such as a syringe or an injector. The fitment 12 comprises a fluid passageway 161, and a static mixer 162 disposed in the fluid passageway 161. The arrangement is such that when the merged first substance and second substance are transferred from cartridge 160 to a dispensing device the static mixer enhances the mixing of these substances to form a more homogeneous product. An example of a static mixer is taught in U.S. Pat. No. 4,538,920, which is incorporated herein in its entirety by this reference. The mixture may further be transferred back and forth between the delivery device and the cartridge to repeat the mixing action at the static mixer. In some arrangements, the static mixer is constructed as a pattern of passageways formed between the walls of the flexible package by welding and pre-forming designated areas of the walls. The static mixer may be merely a narrow nozzle, or a porous component accommodated in the flow passageway between the cartridge and the delivery device.

Figure 17:
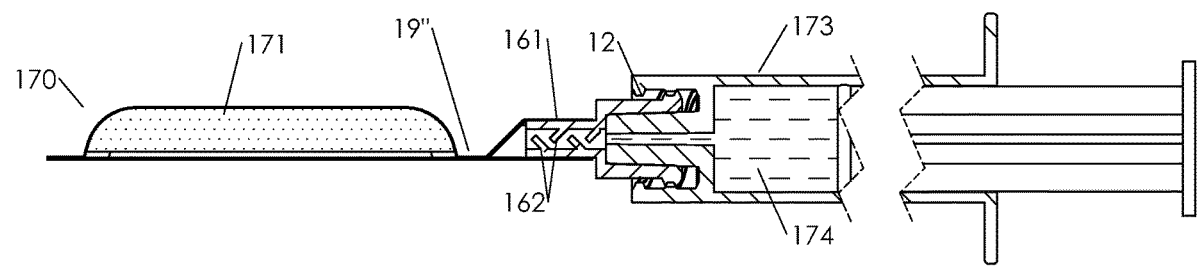
FIG. 17 illustrates a system for mixing a first constituent contained in a cartridge and a second constituent contained in a syringe.

FIG. 17 illustrates an arrangement in which the cartridge 170 comprises a compartment 171 containing a first substance or at least one constituent of a dispensable product, and separated from a female Luer lock fitment 12 by a second frangible seal 19". The fitment comprises a fluid passageway 161 and a static mixer 162 disposed in the fluid passageway 161. A syringe 173 containing in its reservoir a second substance or at least one constituent of a dispensable product 174 is attached to the cartridge 170. The second frangible seal 19" is rupturable to allow the first substance and the second substance to merge. By drawing the syringe piston, the first substance is drawn out of the compartment 171 and into the syringe where the first substance merges with the second substance. The syringe piston may be operated back and forth to transfer at least a portion of the mixture to and from the cartridge 170 and create a more homogenous mixture as the material flows through the static mixer 162. In one arrangement, the compartment 171 is sufficiently expandable to receive substantially all of the merged substance of the cartridge and the syringe reservoir. In some arrangements, the cartridge 170 may comprise more than one compartment that may be merged with the first compartment 171 before or after merging the first compartment with the syringe. It will be obvious to one skilled in the art that a static mixer may be implemented in any of the previous arrangements of this disclosure in similar arrangements to that of FIG. 16 or FIG. 17. In particular, referring back to FIGS. 3 and 4, the static mixer may be disposed in the syringe's stem or plunger.

Figure 18:
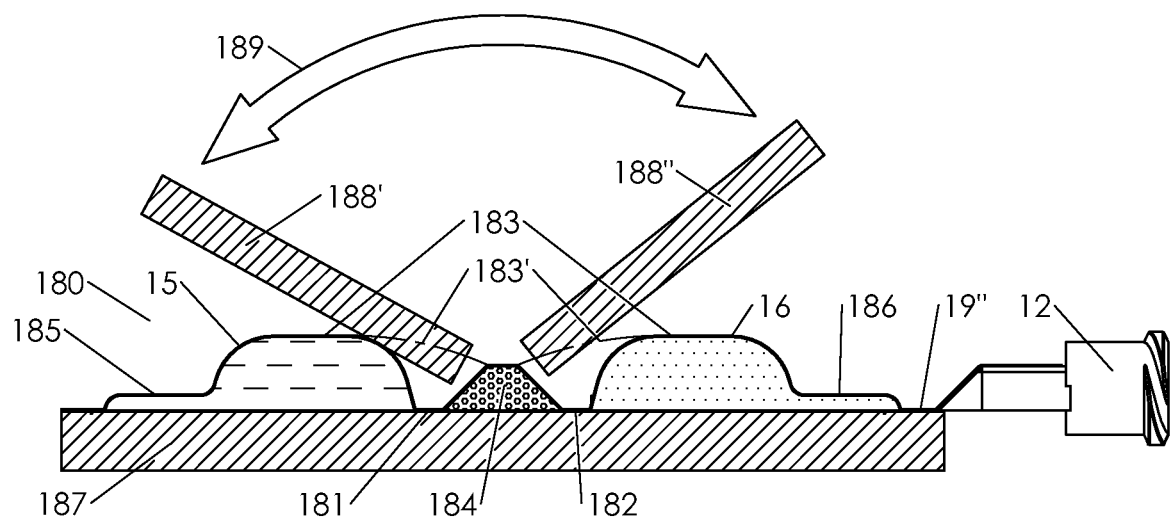
FIG. 18 illustrates a system for mixing a first constituent and a second constituent contained in a cartridge.

FIG. 18 shows another arrangement of a cartridge 180, comprising a first compartment 15 containing a first substance or at least one constituent of a dispensable product, a second compartment 16 containing a second substance or at least one constituent of a dispensable product, and a static mixer 184 disposed there between, separated from the first compartment 15 by a frangible seal 181, and separated from the second compartment 16 by a frangible seal 182. At the point that the first substance and the second substance are to be mixed, the first frangible seal 181 and the second frangible seal 182 are ruptured such that the upper wall 183 is rearranged as indicated by dashed line 183' to allow the first substance and the second substance to communicate via the static mixer 184. The first compartment 15 and the second compartment 16 are not fully inflated as the first recessed area 185 of the first compartment 15, and the recessed area 186 of the second compartment can expand to receive substance from the other compartment. Consequently, a good mixture of the first substance and the second substance may be achieved by alternately compressing the first compartment 15 and the second compartment 16, and transferring the mixture of the first and second substances through the static mixer 184. The static mixer 184 is shown here as a porous body, and alternatively be another static mixer known in the art.

A third frangible seal 19" is rupturable to establish communication between the mixture and the fitment 12. The arrangement further comprise a backing 187 supporting the cartridge 180, and a rocker comprising a first compression panel 188' and a second compression panel 188". The rocker may be movable to rotate relative to the backing 187 to alternately depress the first compartment 15 with the first compression panel 188' and the second compartment 16 with compression panel 188" in the direction 189. The rocker and backing arrangement facilitate an efficient operation of the mixture process by more efficiently and systematically compressing the first and second compartments 15 and 16 and transferring the content across the static mixer 184. At the point that the mixture is ready to transfer to a dispensing device through the fitment 12, the first compression panel 188' may be resting where the first compartment 15 is depleted so that substantially all of the mixture is expressed from the second compartment 16 to the fitment 12. The rocker may be associated with the backing 187 via a hinge or a living hinge, and it may be operated manually or by a device.

Figure 19:
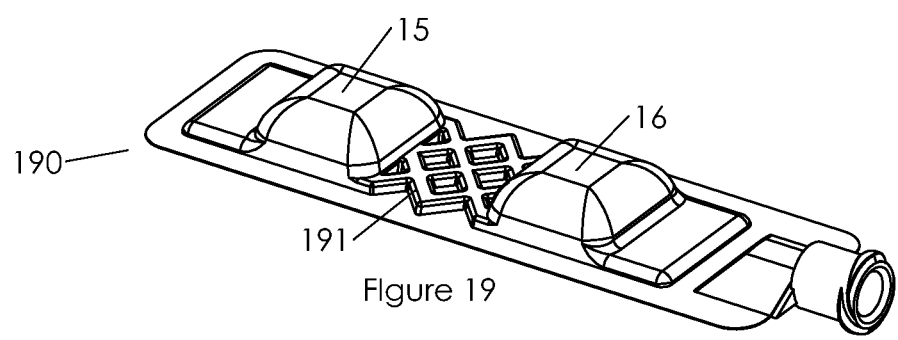
FIG. 19 illustrates a static mixer integrally formed in a blister-type cartridge.

FIG. 19 shows another arrangement of a cartridge 190 comprising a first compartment 15, containing a first substance, a second compartment 16 containing a second substance, and an array of pre-formed intercrossing channels 191 positioned therebetween to provide a static mixer that enhances the mixing of the first and second substances as they are transported back and forth between the first compartment 15 and the second compartment 16.

Referring now to FIG. 20a to 20g, one possible manufacturing method of the cartridge is described. In one arrangement, this manufacturing process is accomplished on a form-fill-seal system.

Figure 20A:
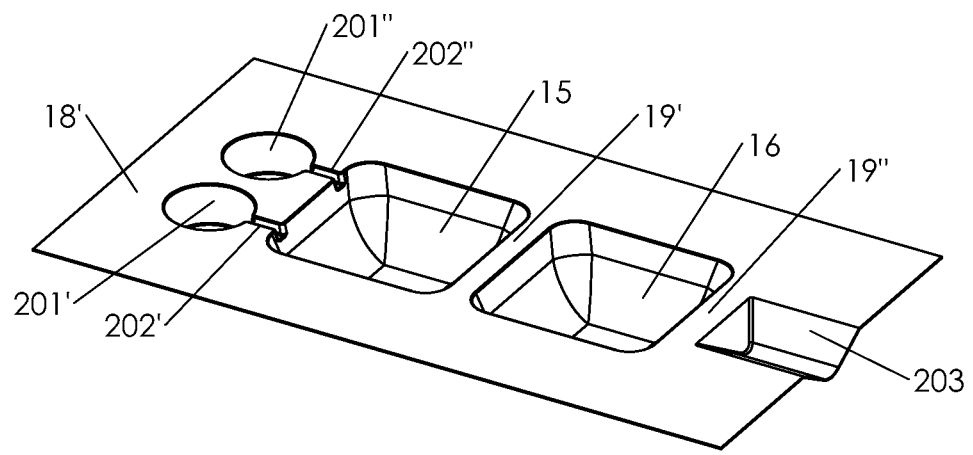
FIGS. 20a to 20e illustrate a method for fabrication of the cartridge.

FIG. 20a shows a pre-formed flexible first wall 18' of a package for storing constituents of a beneficial agent. The package includes a first cavity 15 (subsequently the first compartment) for receiving a first constituent, a second cavity 16 (subsequently the second compartment) for receiving a second constituent, a first uninterrupted area with the surface at the peripheral edge of cavity (subsequently the first frangible seal area) positioned there between, a fitment cavity for receiving a fitment, and a second uninterrupted area with the surface at the peripheral edge of compartment (subsequently the second frangible seal area) between the second compartment 16 and the fitment cavity 203. The second cavity 16 may receive a non-fluidic material or a poorly flowing material such as, for example, powder, compressed or agglomerated powder, granules, pellets, solid, tablet, capsule, slurry, paste, high viscous fluid, emulsion, and a combination of the above. The second substance is filled into the second cavity 16 by an appropriate filling system that provides the type of material that needs to be filled. The second compartment 16 may also be filled with water or other low viscosity fluids. It may be challenging to completely fill the second compartment 16 with water or aqueous solution due to surface tension and other properties of the fluid, which may make it challenging to keep the fluid in the cavity as it is being sealed.

Another challenge is that liquid filling is a relatively slow manufacturing process for a number of factors, one of which is avoiding foaming or bubble formation as the liquid is filling the second compartment 16. In one arrangement, this challenge is addressed by freezing aliquots of fluid in a mold preferably having the second compartment 16 shape, then transporting the solid aliquots into the cavity by one of the means known in the art. The production line, and in particular the filling station, may be designed such that heat transfer to the frozen liquid aliquots is limited so that the frozen liquid aliquots stay substantially solid until the second compartment 16 is sealed. Thereafter, the frozen liquid aliquots may be thawed. Heat transfer to the frozen liquid aliquots during the filling process may be limited by controlling the temperature throughout this process substantially low, and by using machine construction and selecting contact material to the package that provide appropriate heat transfer properties. The frozen liquid aliquot may be inspected for weight and other controlled properties and parameters prior to introduction to the second cavity 16.

In one arrangement, more than one frozen liquid aliquot is filled to the second compartment 16, which may have the same, similar or different compositions. These aliquots may have complementary shape that may jointly form substantially the shape of the second compartment 16. In one arrangement, the aliquot is frozen directly in the second compartment 16 or on the reciprocal flat second wall 18" (not shown) of the package. In another arrangement, the second substance is a loose powder or another form of dispersible dry substance which may be challenging for filling to the second compartment 16. Loose powder filling may also be a limiting factor of the manufacturing speed and a challenge for proper inspection of the aliquot fill dose. In one arrangement, in order to facilitate the powder filling (or similar dry substance), the powder is slightly compressed to form a loosely aggregated tablet, or a unitary body, and is filled in that form into the compartment of the package by one of the tablet filling means known in the art. The unitary body may be molded to substantially the same shape as the shape of the second compartment 16. A dedicated formulation may be required to achieve the level of aggregation at a given compression rate. The tablet may be inspected prior or during the fill process of the second compartment 16.

In one arrangement, after the tablet has been sealed in the second compartment 16, the compartment is externally manipulated to de-agglomerate the tablet, thus improving the substance solubility (or dispersability) at the time of mixing with a dilutant. The external manipulation may include directing energy to the unitary body through the wall of the package via at least one of, but not limited to, compression of the compartment, vibration including ultrasonic vibration, radio frequency vibration, acoustic vibration, applying mechanical impact to the compartment, and exposure to high or low temperatures. In one arrangement, the unitary body is formed directly in the second compartment 16 or on the reciprocal flat second wall 18" (not shown) of the package. The first compartment 15 provides another arrangement for efficiently filling a low viscosity fluid to substantially fill the first compartment 15. A first filling compartment or chamber 201' and a second filling compartment or chamber 201" are pre-formed in the first wall 18'. The first filling compartment or chamber 201' may also be referred to as an inlet filling compartment in this embodiment. The second filling compartment or chamber 201" may be referred to as an outlet filling compartment in this embodiment, and may be referred to as an evacuation compartment in some embodiments.

The first passageway 202' and second passageway 202" are arranged and configured to connect the first and second filling compartments 201', 201" in communication with the first compartment 15. The first passageway 202' may be referred to as an inlet passageway, a first filling channel, or a first pre-formed filling channel. The second passageway 202" may be referred to as an outlet passageway, a second filling channel, or a second pre-formed filling channel. The first and second passageways 202', 202" may be referred to as fillable channels or passageways used to fill the first and second sealed compartments 15, 16. FIG. 20a shows a portion of a web formed to include the details of one cartridge. It would be understood to those skilled in the art that in a normal manufacturing practice an array of details for multiple cartridges may be formed on a larger spread of the first wall 18', and may be handled simultaneously at subsequent forming and filling steps. The cartridge 200 or any portion thereof (e.g., the first wall 18') may comprise a blister package that defines pre-formed cavities such as the first and second sealed compartments 15, 16. The first wall 18' may be pre-formed from a flat web by one or more of the processes including, for example, thermoforming, cold forming, vacuum forming, pressure forming, plug-assist forming, or pre-forming from non-web raw material such as by injection molding, blow molding, injection-blow molding, blow-fill-seal, blow-fill-insert-seal, or other methods known in the art.

Figure 20B:
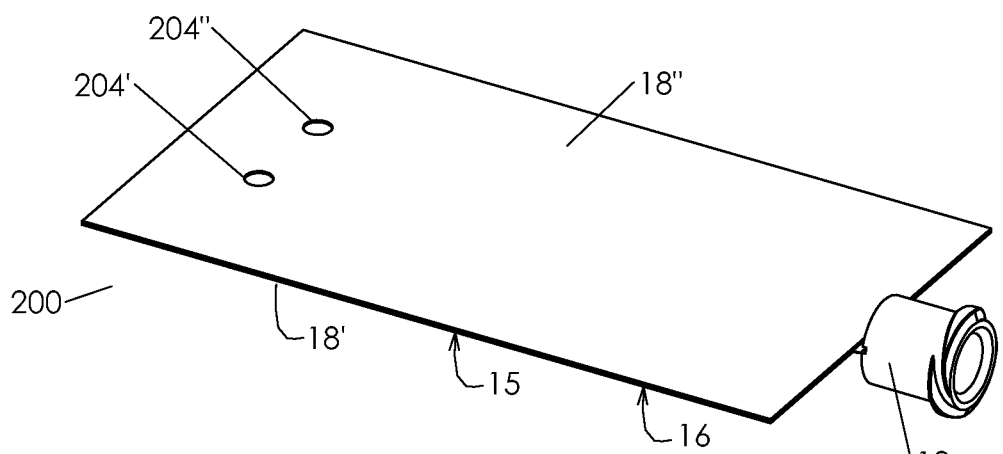

FIG. 20b shows a subsequent step of the manufacturing process of the cartridge 200. After the second compartment 16 (in this Figure at the opposite side of the cartridge 200) has been filled, the second compartment 16 is hermetically sealed with a lid web or second wall 18". The second wall 18" is sealed to the entire uninterrupted surface of the first wall 18'. In one arrangement, the inner layer of the first wall 18' and/or the second wall 18" comprises an adhesive with controllable peeling (adhesion) force, where a lower sealing temperature (for instance about 300° F.) results in a peelable adhesion ("frangible seal"), and a higher sealing temperature (for instance about 420° F.) results in a permanent non-peelable adhesion. In one arrangement, the frangible seal peeling force is about 1,000 g/in$^2$, and the permanent seal is greater than about 1,600 g·in$^2$). In one arrangement, at the first sealing step shown in FIG. 20b, substantially all of the uninterrupted surface of first wall 18' is adhered to the second wall 18" to form a frangible seal that extends completely around a circumference of the second compartment 16, and extends around substantially an entire circumference of the first compartment 15 with the exception of the first and second passageways 202', 202", which remains unsealed to allow fluid communication between the filling compartments and the first compartment 15. With the second wall 18" now attached to the first wall 18', a filling compartment and exhausting compartments are now formed that communicate with the first compartment 15 via channels or passageways formed between the two webs. A pattern 401 of the frangible seal is shown in FIG. 20f.

The first filling hole (i.e. first filling port) 204' and the second filling hole (i.e. second filling port) may be made in the second wall 18" in advance of this manufacturing step by one of the means known in the art such as, for example, punching, die-cutting, and laser cutting. In some arrangements, the second wall 18" is joined with the first wall 18' prior to piercing the filling ports, and first and second walls 18', 18" are pierced by the filling device at the filling step. In one arrangement, the first compartment is filled with a first substance through the first filling hole 204' while the second filling hole 204" allows for evacuation of gases from the first compartment 15 during filling. A filling source may be associated with at least one of the filling holes 204' and 204" during the filling process to facilitate the introduction of a substance to the first compartment, and drawing the gases through the exhaust compartment. At least one of the second filling hole 204" and second passageway 202" may be sized to prevent the substance from reaching the exhaust port. In one arrangement, the filling device comprises a needle or a tube that is bent to reach into the first filling channel 202'. The gases drawn through the first or second compartment 15, 16 and one of the filling holes 204', 204" may be connected to an exhaust line (not shown) that draws the gases away from the cartridge. The compartment through which gas is evacuated may be referred to as a gas evacuation compartment.

In one arrangement, the filling device comprises a cylindrical filling tube with a diameter greater than that of the filling hole 204' such that it tightly fits and fluid-tight seals when introduced to the filling hole 204'. In one arrangement, the filling holes 204' and 204" are formed during the filling step by a sharp filling object (such as a hollow needle or other piercing element) that pierces through the second wall 18", into filling compartments 201' and 201" in a fluid-tight fashion. The sharp filling object may be a tube (e.g., a capillary tube) that is connected in fluid communication with a first constituent. The second wall 18" (also referred to as a web) may form a fluid-tight seal with the tube.

This last arrangement is particularly beneficial as the package is hermetically sealed prior to the introduction of the constituent, which can be performed on a different portion of the filling line or on a different line of a filling machine (e.g., a form-fill-seal line). The packages may be stacked between the sealing step and the filling step. In one arrangement, a rubber or semi-rigid sealing member is disposed in at least one of the filling compartments 201' and 201" forming an interface to the filling source to facilitate the sealing of the filling couplers to the cartridge. In one arrangement, the channels' cross section is sufficiently small to prevent the filled substance from spilling out of the first compartment 15, due to surface tension or particles size of the substance.

In one arrangement, a check-valve is disposed in at least one of the first and second filling compartments 201' and 201" to control the flow of a substance into the first compartment 15. A semi-permeable object may be disposed in one of the filling compartments 201', 201" and the first and second passageways 202', 202" to allow gases to escape during filling and prevent the substance from leaving the first compartment 15 by backflow. In one arrangement, the flow evacuating the first compartment 15 during filling is monitored and filling is discontinued when the evacuating fluid switches from gas to the filled substance. A sensor may be positioned in one of the first and second passageways 202', 202" for detecting presence of a substance. The sensor may indicate that the filling compartment is filled. The sensor may comprise electrodes disposed on the second wall or in between layers of the second wall 18" material. The electrodes and the associated sensing circuit may be configured to sense conductivity of the fluid in the second passageway 202".

The first filling channel 204' is configured to direct the substance entering the first compartment to glide on the second wall 18" and thus preventing jetting that may result in undesired bubbles or foaming of the filled dose. A dedicated flow deflector may be disposed in the first and second passageways 202', 202" or one of the filling compartments 201', 201" to facilitate the gliding of the filled substance on the wall of the first compartment 15. In one arrangement the package 200 is molded to the configuration of FIG. 20*b* for example by blow-molding or gas assist molding.

Figure 20C:
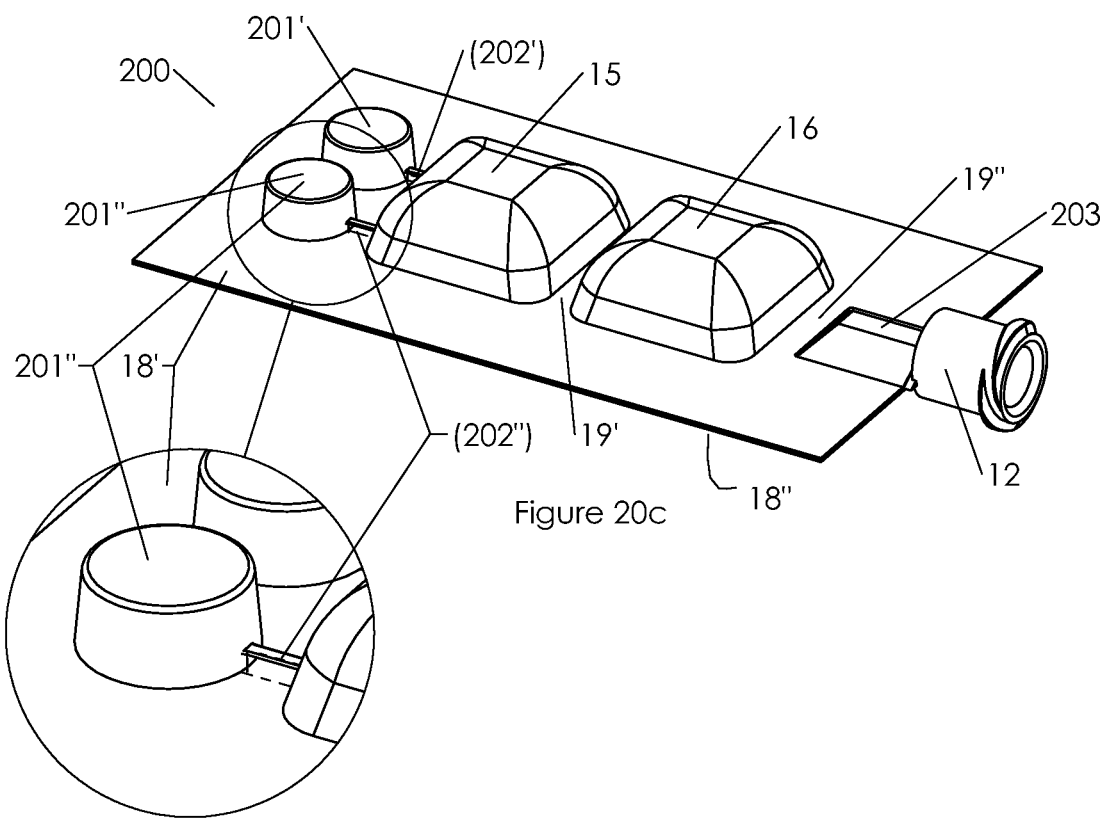

FIG. 20*c* shows a subsequent manufacturing step of the cartridge 200. In a second welding step, the first and second passageways 202', 202" are depressed and welded to completely seal the first substance in the first compartment 15. The sealing temperature may be higher than the frangible seal welding temperature to avoid rupture of the first and second passageways 202', 202". In one arrangement, this sealing step is further applied to the circumference of the cartridge 200 to apply permanent seal properties to at least some of the areas that were earlier sealed as a frangible seal. A sealable insert may be disposed in the channels to facilitate welding and sealing of the channels. This insert may be made of a material with substantially low melting temperature that is adherable to the inner surface of the first and the second walls 18' and 18" to enhance the seal of the first and second passageways 202', 202" at the second sealing step. An insert may be disposed in at least one of the first and the second filling channels and the first and the second filling compartments to provide at least a portion of a flow control device. The flow control device may be one of, for example, a valve (e.g., an isolation valve or a check valve), a flow or pressure regulator, a flow or pressure restrictor, or a flow deflector, etc. A pattern 402 of the permanent seal is shown in FIG. 20*g*. The permanent seal pattern 402 is shown in FIG. 20*g* partially overlapping the frangible seal pattern 401.

Figure 20D:
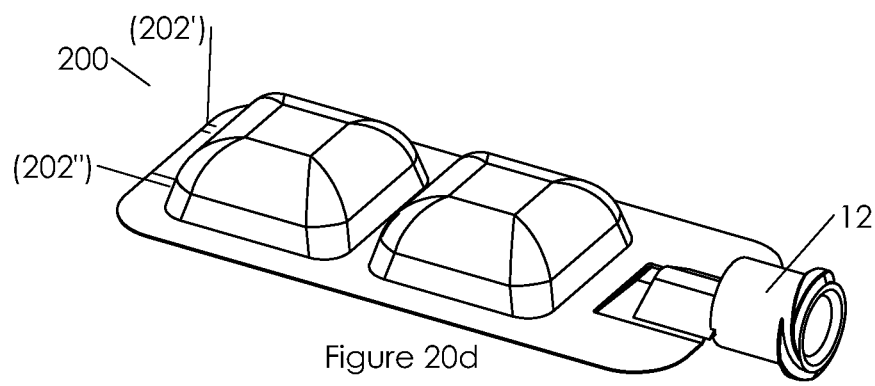
Figure 20E:
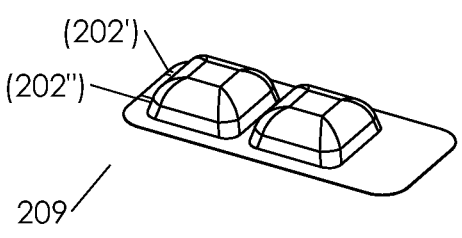
Figure 20F:
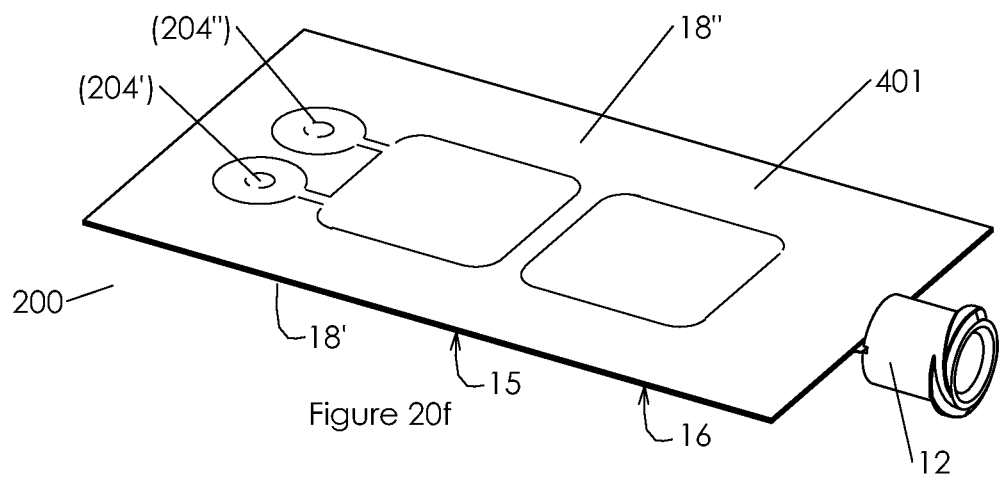
FIGS. 20f and 20g illustrate the frangible and permanent seal patterns of the cartridge of FIGS. 20a to 20e.
Figure 20G:
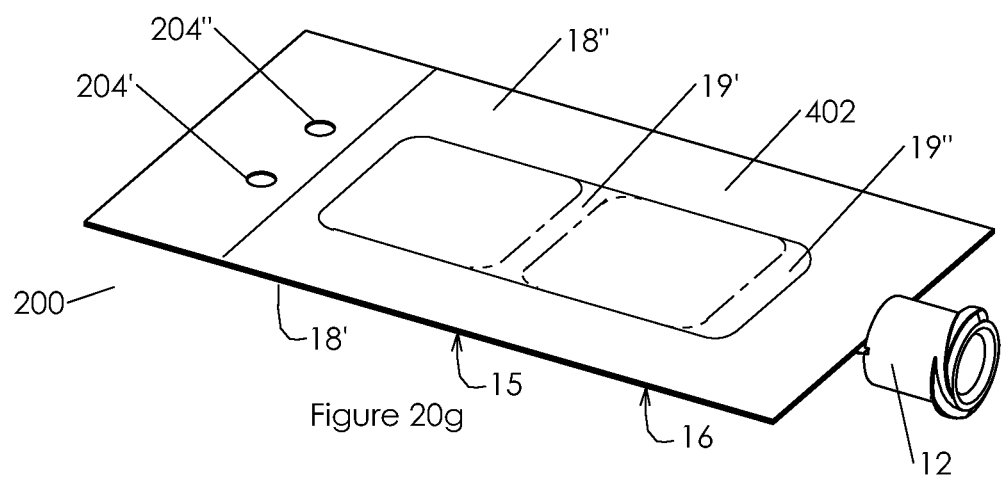

Referring now to FIG. 20*d*, the cartridge is trimmed from the web margins by one of the means known in the art such as, for example, punching, ruler steel cutting, laser cutting, etc. FIG. 20*e* shows cartridge 209 without the fitment cavity 203 and fitment 12.

It would be understood to those skilled in the art that the order of manufacturing steps disclosed above may be rearranged in whole or in part to best suit a particular design, application, and applicable manufacturing equipment. It would also be understood to those skilled in the art that additional manufacturing steps may be performed prior to, in between, and after the steps described in FIGS. 20*a* to 20*d*.

The fitment 12 is welded to and positioned between the first pre-formed wall 18' and the second wall 18" prior to or during the frangible seal welding step, prior to or during the permanent seal welding step, or in a subsequent step by one of the fitment welding means known in the art including, for example, heat stake welding, impulse welding, vibration, ultrasonic, RF welding, and light beam welding.

FIG. 20*f* illustrates a first welding step of the first pre-formed wall 18' to the second flat wall 18" of the package of the cartridge 200. The sealing pattern 401 completely circumscribes the second compartment, hermetically sealing the content of the second compartment. The first compartment 15, the filling compartments and the filling passageways are sealed around leaving the passageways between the filling compartments and the first compartment open. The subsequent location of the filling ports is marked (204') and (204") and they will be opened at a later manufacturing step, hence the frangible seal 401 hermetically seals the cavity comprising the first compartment 15 and the filling compartments.

FIG. 20*g* illustrates the cartridge 200 after the permanent seal step. The permanent seal pattern 402 surrounds the first and the second compartments overlapping most of the frangible seal pattern except for the first frangible seal section 19' and the second frangible seal section 19". In an earlier step, the filling ports 204' and 204" were pierced by the filling device and the first compartment was filled as described earlier. The filling channels are sealed by the permanent seal pattern 402 hermetically resealing the first compartment.

Figure 21A:
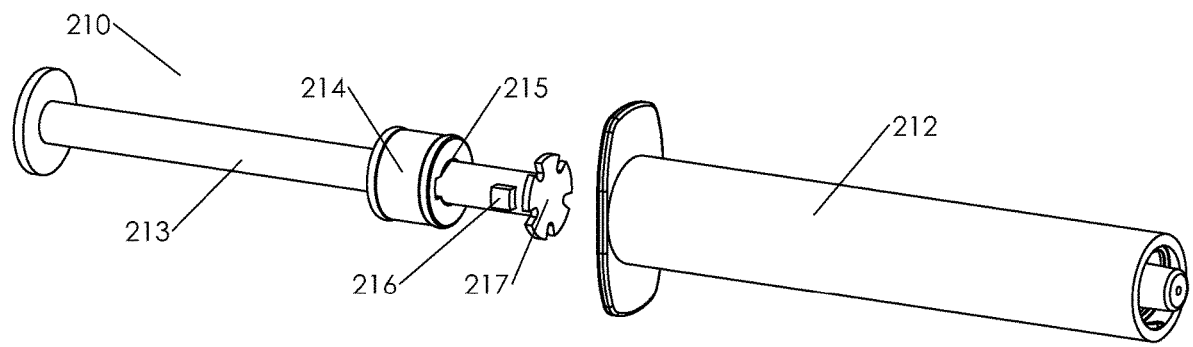
FIGS. 21a to 21e illustrate a syringe comprising a static mixer for mixing a substance contained in a syringe with a substance contained in a cartridge.

FIG. 21*a* shows an exploded view of a syringe 210 comprising a static mixer for mixing substances. In one arrangement, a first substance is contained in the syringe 210 and a second substance is transferred from a cartridge (not shown) to the syringe, where it is mixed with the first substance. In another arrangement, at least a first substance and a second substance are transferred to the syringe from one or more cartridges (or from a different source of the substance), separately or pre-mixed, where a mixture process is applied to the substances or mixtures. In some arrangements, a cartridge is associated with the syringe 210 in a similar fashion to that of the arrangements of FIG. 2, 3, 4, 13 or 14. A plunger 214 is movably disposed in the syringe barrel 212 in a fluid-tight fashion. A piston 213 is concentrically disposed in a movable fashion in the annular bore of the plunger 214 in a fluid-tight fashion, and the piston further comprises a static mixing plate 217 (or static mixer) that extends laterally from the distal end of the piston 213. A local axial groove 215 in the annular bore of the plunger 214 is made to receive laterally protruding detent tooth 216 of the piston 213.

Figure 21B:
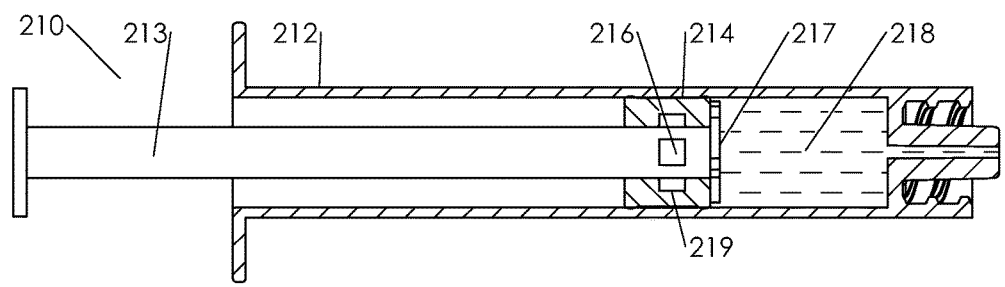
Figure 21C:
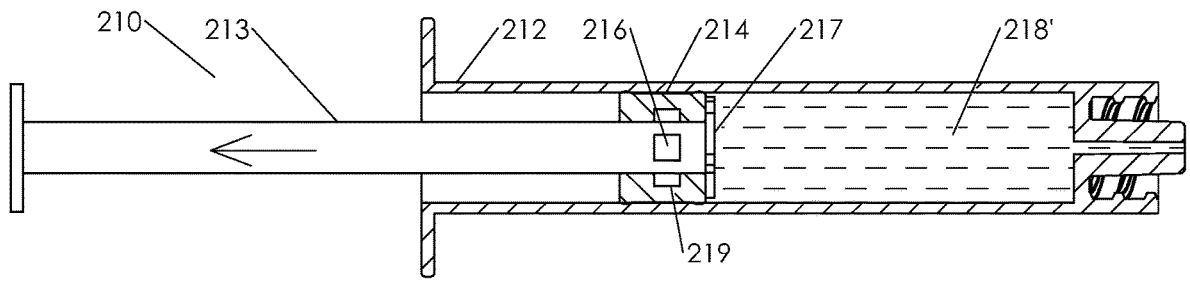

FIG. 21b shows a section view of the mixing syringe 210 containing a first substance 218. FIG. 21c shows a section view of the mixing syringe 210 where the piston is retracted toward the proximal end of the barrel 212. The static mixer pushes the plunger along with the piston, thereby allowing a second substance to enter the barrel 212 to form mixture 218'. The source of the second substance is not shown. However, as described above, the source may be a cartridge associated with the syringe 210 in one of the arrangements provided in this disclosure. It is understood that if the second substance is not entering the syringe 210 from the Luer tip, the Luer tip is sealed with a cap, a closure, a valve or another means such that no flow from the tip occurs during the piston retraction.

Figure 21D:
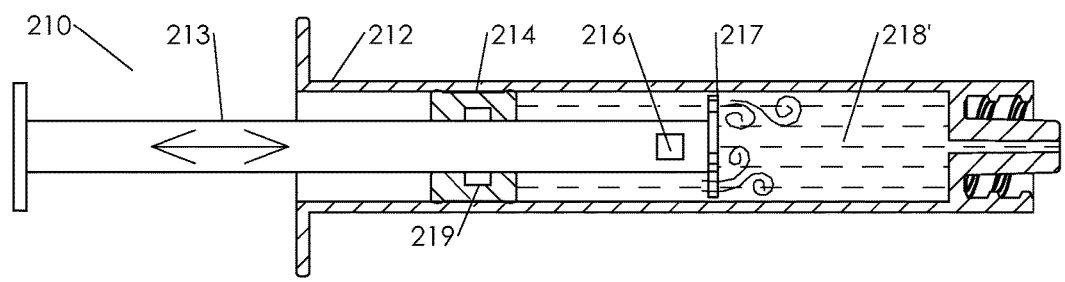

FIG. 21d shows a mixing step where the piston 213 is moved back and forth, diverting the mixture 218' to flow through the openings in the static mixer 217 and enhance the mixing of the mixture 218' to form a homogeneous product. The detent tooth 216 is aligned with the axial groove 215 (not shown) such that the piston is freely movable relative to the plunger 214. The plunger is free to glide along the barrel as it moves into and out of the sealed volume between the barrel 212 and the plunger 214. In one arrangement, the piston is rotatable to further enhance the mixing. In one arrangement, the static mixing plate is replaced with another static mixer known in the art such as a porous material. In one arrangement, the piston is operated by a device such as a controlled electric actuator. The syringe tip and other ports to the syringe are preferably tapped during the mixing process to avoid spillage of mixture 218' or introduction of materials into the barrel 212.

Figure 21E:
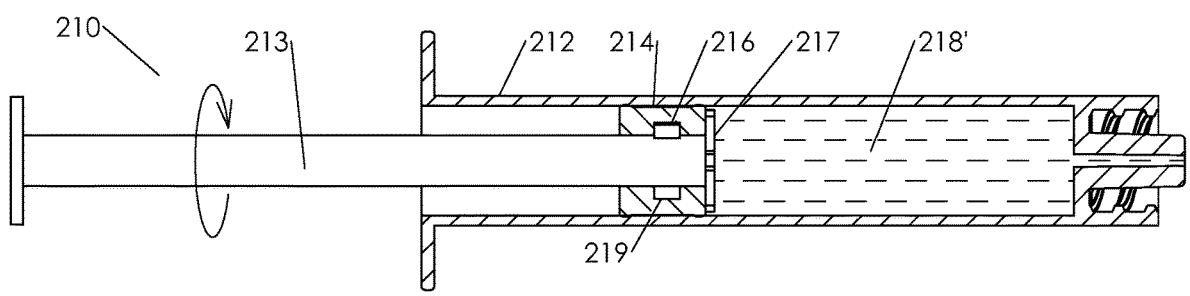

FIG. 21e shows the syringe 210 as the piston is retracted, such that the detent tooth 216 enters axial groove 215 (not shown). The piston is rotated such that the detent tooth 216 engages with the radial groove 219 of the plunger 214, at which position the plunger 214 and the piston 213 are firmly engaged and are movable as one. In one arrangement, the barrel and plunger comprise a non axi-symmetric cylindrical profile to prevent the rotation of the plunger due to the piston 213 rotation. In one arrangement, the plunger 214 comprises a rigid core to facilitate engagement with the piston 213. As the syringe's 210 tip is untapped, the mixture 218' is dispensed by advancing the piston 213 and plunger 214 toward the distal end of the syringe 210.

Figure 22A:
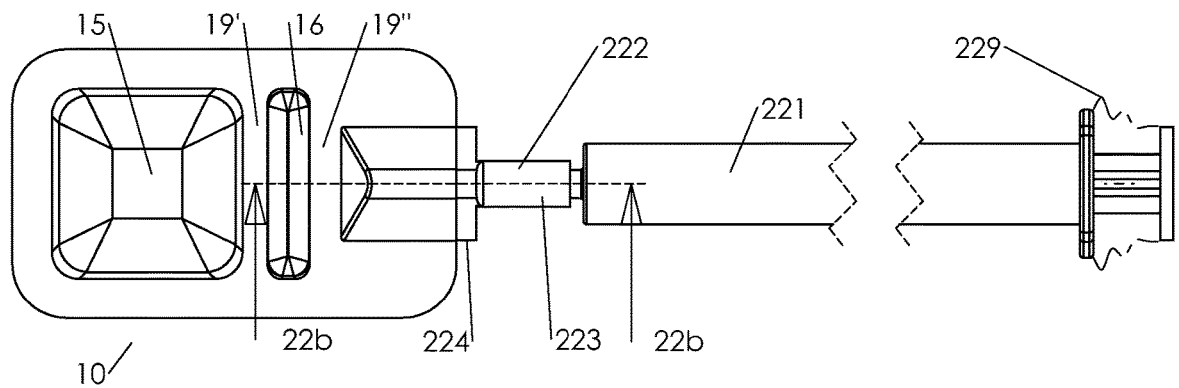
FIGS. 22a and 22b illustrate a cartridge communicating with a staked needle syringe via a fitment.
Figure 22B:
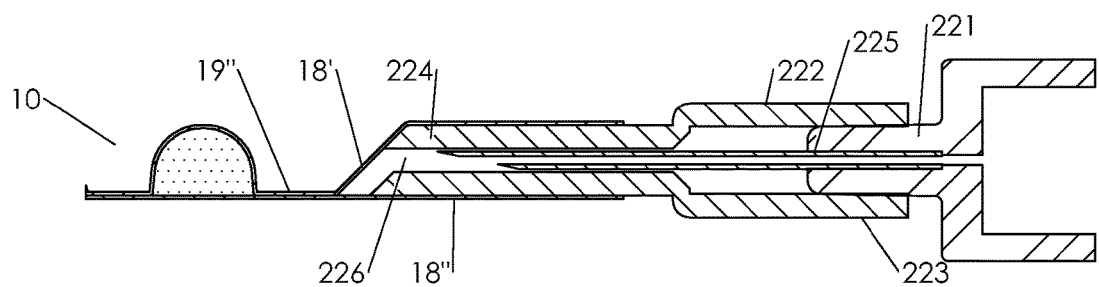

FIG. 22a and the partial cross-section in FIG. 22b illustrate a cartridge associated with a staked needle syringe. The cartridge 10 comprises a first substance compartment 15 and a second compartment 16 separated by a rupturable barrier or first frangible seal 19'. The cartridge 10 further comprises a fitment 222, for communicating the content of the cartridge 10 with a staked needle syringe 221. The proximal end 224 of the fitment 222 is sealed between the first wall 18' and the second wall 18" of the cartridge 10, and is separated from the second compartment 16 by a rupturable barrier or second frangible seal 19" that is formed by directly sealing the first wall 18' and the second wall 18". The distal end 223 of the fitment 222 is made to removably receive the tip of the syringe 221 in a fluid-tight fashion, and the proximal end 224 of the fitment 222 is made to receive the tip of a needle 225 and protect the tip. A passageway 226 in the fitment 222 communicates between the needle and the content of the cartridge 10. The cartridge 10 provides an aseptic needle protector to the needle 225. The needle 225 may be an injection needle.

In one arrangement, the original needle protector (not shown) is removed from the syringe and is replaced by cartridge 10. The content of the cartridge 10 is transferred to the syringe 221 after the second frangible seal 19" has been ruptured. In some arrangements, the cartridge 10 is mounted on the syringe during the manufacturing process. In one arrangement, the cartridge 10 has only a single compartment. In one arrangement, the cartridge has at least two compartments that are merged prior to transferring the content of the cartridge 10 to the syringe 221. In one arrangement, the syringe 221 comprises a safety mechanism which, at the end of the injection, retracts at least a portion of the needle 225 to a position that protects from needle sticks. In one arrangement, the syringe 221 comprises a needle stick prevention device that at least partially protects the needle tip after the injection of the content has been completed.

Typically, with pre-fillable syringes, the syringes are supplied to the filling process disassembled, and the syringe is fully assembled after the content has been filled. The arrangement of FIGS. 22a and 22b provides for an advantageous manufacturing method wherein (a) the syringe 221 is supplied assembled and finished, (b) the cartridge 10 is filled and sealed with the desired content, and (c) the cartridge 10 is assembled. This process may be completed in an aseptic environment or the product may be terminally sterilized. Thus, the approach allows for producing a pre-filled syringe assembly that does not require the actual syringe components assembly. In addition, the cartridge may be marked and labeled with the content information without needing a special syringe label or package to provide this information. A label, or a portion of a label, of the cartridge 10 may be transferable to the syringe to maintain the product identification after the cartridge 10 has been removed.

FIGS. 22a and 22b illustrate a cartridge adopted to communicate with a staked needle syringe. The cartridge 10 comprises two mergeable substance compartments. However, the cartridge 10 may include merely one compartment or more than two compartments. The connection between the syringe 221 and the fitment 222 is shown as a fluid-tight slip-fit. However, other fitting features may be incorporated to facilitate a tight connection between the syringe 221 and the cartridge 10, their assembly, or their dismantle, including, for example, a thread, a helical ramp, a Luer fit, a Luer-lock fit, an O-ring, a rubber seal component, an interlocking feature, a snap feature, other features known in the art to facilitate a fluid-tight, removable connection, or a combination of the above. The distal end 223 of the fitment 222 may tightly fit around the needle 225, providing a fluid-tight seal around the distal end of the needle that prevents the content of the cartridge 10 from reaching to the space between the proximal end of the fitment 222 and the proximal end of the needle 225, and prevents air from reaching into the needle from that area. The fitment may be at least partially made from elastic material. The fitment 222 may be designed to accommodate the cartridge 10 in different orientations relative to the syringe. In one arrangement, the cartridge 10 and the syringe 221 may at least partially overlap or rest side-by-side. The syringe's piston and barrel may be sealed at their proximal end by an aseptic membrane 229 such that the content contact surfaces will remain sterile without needing a sterile overwrap until the time of use. In one arrangement, the staked needle syringe is replaced with a retractable needle syringe such as the syringe taught by U.S. Pat. No. 8,052,654, which is incorporated herein in its entirety by this reference.

Figure 23A:
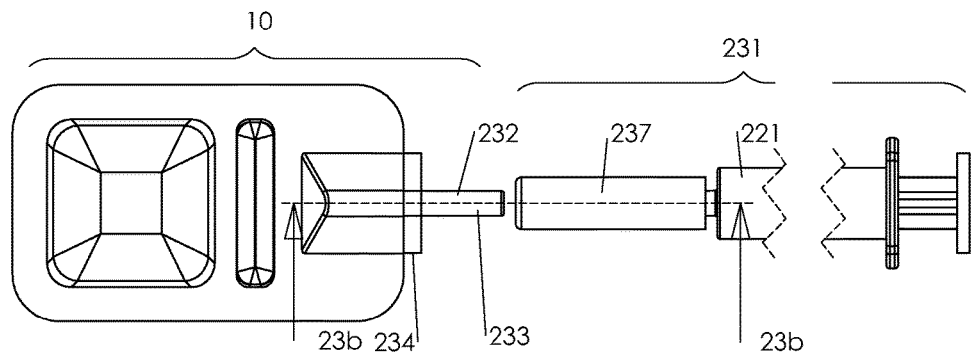
FIGS. 23a to 23g illustrate a cartridge and a staked needle syringe attachable via a coupler.
Figure 23B:
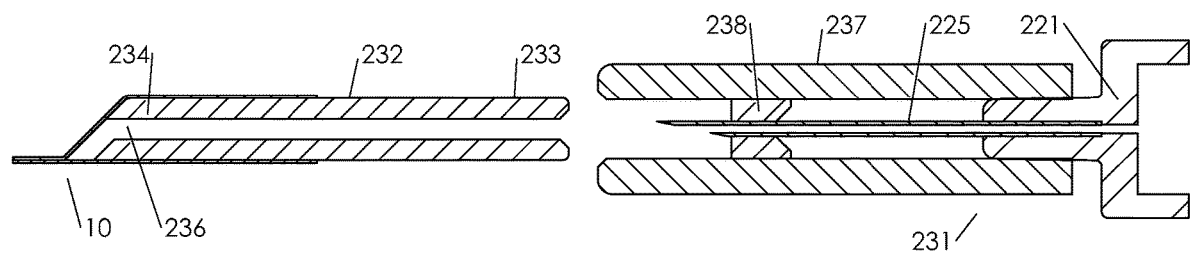

Referring to FIG. 23a and its scaled-up partial section view in FIG. 23b, another preferred arrangement of a cartridge and a staked needle syringe is illustrated. A coupler 237 is axially disposed around the needle 225 and is removably joined to the tip of the syringe 221 in a fluid-tight fashion. The coupler 237 protects the needle from physical damage and the operator and subject from accidental needle sticks. The coupler 237 may be configured as a needle stick preventing device or a reuse preventing device. The coupler 237 may be referred to as an alignment glider. The coupler 237 may provide a seal with at least one of the syringe 221 and a fitment 232 of the cartridge 10.

Figure 23G:
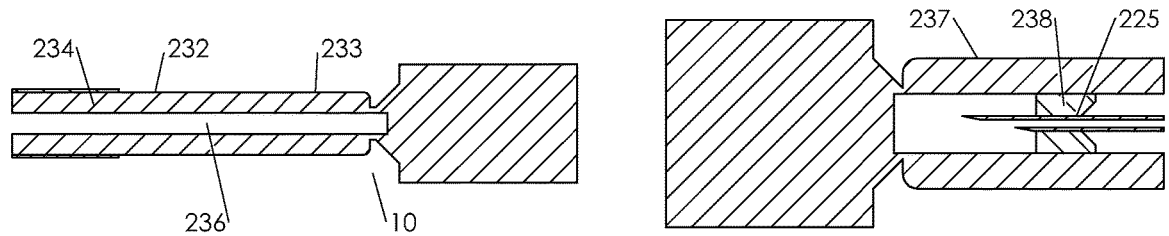

The distal end of the needle 225 is further supported by a centering piece 238 (e.g., centering glider), coaxially, movably disposed in the adapter 237 and around the needle 225. The fitment 232 of the cartridge 10 comprises a proximal section 234 attached to the cartridge walls, and a distal end 233 having an elongated cylindrical construction that can be axially inserted into the coupler 237. With this arrangement, the needle 225 remains protected until the assembly with the cartridge 10. In one arrangement, at least one end of the coupler 237 positioned distal from the syringe 221, or the distal end of the fitment 233, is aseptically sealed with a closure such as a thermally sealed foil, a cap, or knock-off or twist-off members as illustrated in FIG. 23g. This closure maintains the needle sterile until integration with the cartridge, wherein the coupler 237 is removed or ruptured. In one arrangement, the manufacturing method is such that the syringe assemblies 231 are supplied assembled and sterile to the integration line with the cartridge 10.

Figure 23C:
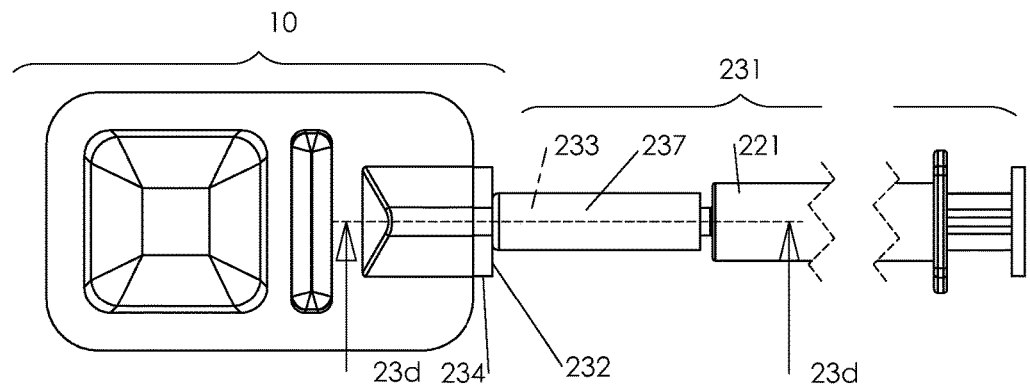
Figure 23D:
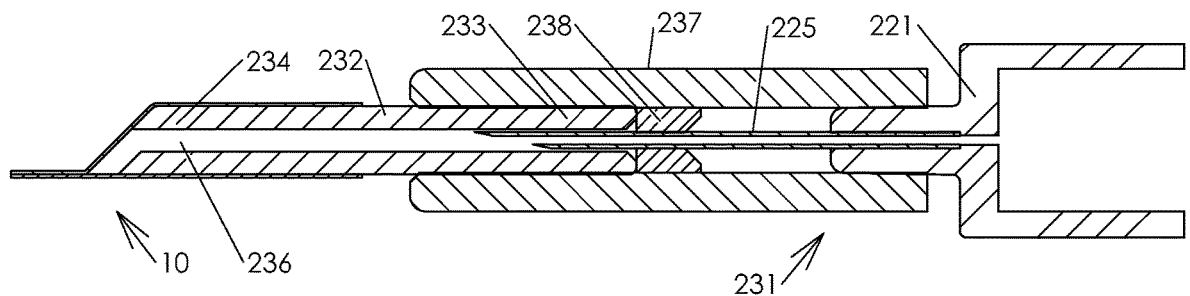

FIG. 23c and its scaled-up partial section view in FIG. 23d illustrate the arrangement of FIGS. 23a and 23b when the syringe assembly 231 and the cartridge assembly 10 are engaged. The distal end 233 of the fitment 232 is inserted into the adapter 237, thereby pushing the centering piece 238 to expose a substantial portion of the distal end of the needle that penetrates the fitment passageway 236 to establish fluid communication between the syringe 221 and the cartridge 10. A fluid-tight seal may be provided by a tight fit between the needle 225 and the fitment 232. The fitment 232 may be at least partially made from elastic material to enhance the seal with the needle 225. The fitment 232 may further include a membrane sealing the distal end 233 or elsewhere along the passageway 236, thereby further enhancing the seal between the fitment 232 and the needle 225, as well as further maintaining the cleanliness of the passageway 236 until it is assembled with a cartridge 10. In one arrangement, the distal end of the fitment 233 forms a fluid-tight seal with the centering piece 238 and the centering piece forms a fluid-tight seal with the coupler. Hence, fluid is prevented from reaching the area between the needle and the coupler.

The content of the cartridge 10 is drawn into the syringe 221. Alternatively to the seal between the needle 225 and the fitment 232, a seal can be established between (a) the centering piece 238 and the adapter 237, (b) the centering piece 238 and the needle 225, (c) the syringe's 221 tip and the adapter 237, and (d) the fitment 232 and the adapter. In some arrangements, two or more substance compartments in the cartridge 10 are merged and allowed to mix before the content is transferred to the syringe 221. In some arrangements, substance in the syringe 221 reservoir is transferred and merged with a substance in the cartridge 10 before drawing the merged product. For example, the cartridge 10 may contain a dry substance, and the syringe 221 may contain a dilutant, the dilutant is transferred to the cartridge 10 and allows the powder to dissolve, and the merged product is either transferred back to the syringe, dispensed to a subject, or transferred to another device. In one arrangement, the syringe is pre-filled with a substance, and the content of the cartridge 10 is transferred to the syringe 221, allowing the content to merge with the substance in the syringe 221. The integration of the syringe assembly and the cartridge may be performed on a manufacturing line or manually by a person at a later stage before injection.

Figure 23E:
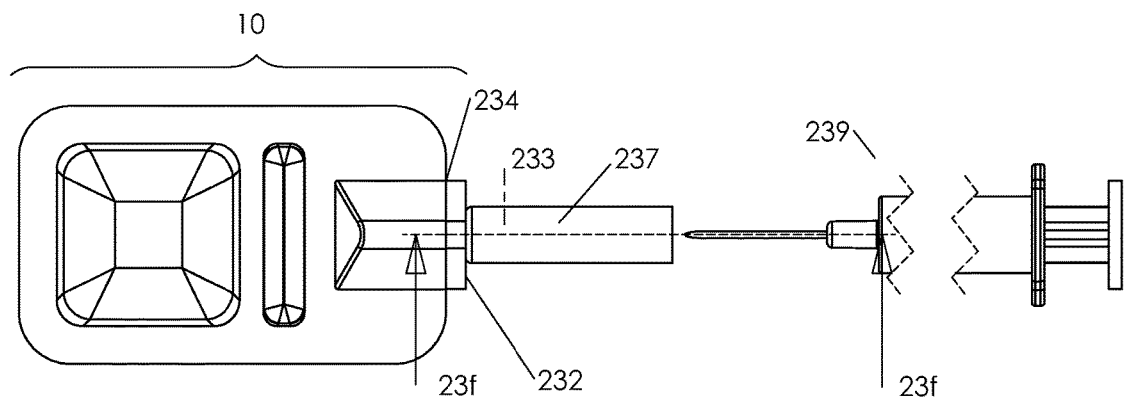
Figure 23F:
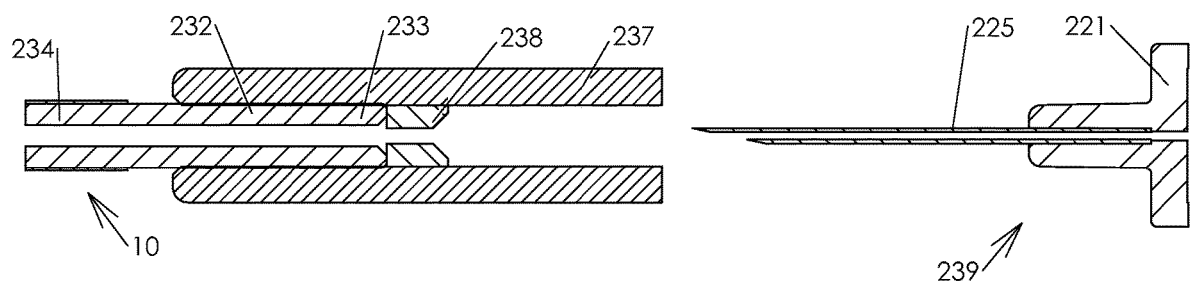

FIG. 23e, and its scaled-up partial section view in FIG. 23f, illustrate the arrangement of FIGS. 23c and 23d when the cartridge 10 is removed. The adapter 237 remains on the cartridge 10, and the needle is exposed as the syringe 221 is now ready for injection. In one arrangement, a mechanical interlock ensures that the adapter 237 remains with the cartridge 10. Such mechanical engagement may include a thread, a helical ramp, a snap, a tight fit, or other engaging and disengaging features known in the art. In one arrangement, the adapter 237 remains on the syringe 221 when the cartridge 10 is removed, to continue providing protection to the needle 225, and the adapter 237 is removed prior to injection by the operator.

Figure 24A:
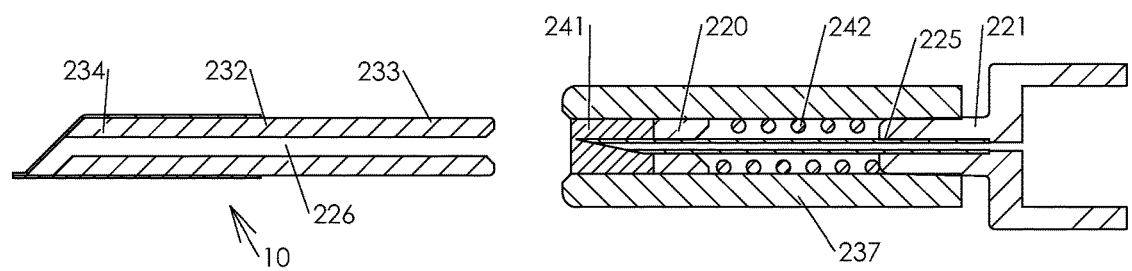
FIGS. 24a and 24b illustrate another arrangement of a staked needle coupler.
Figure 24B:
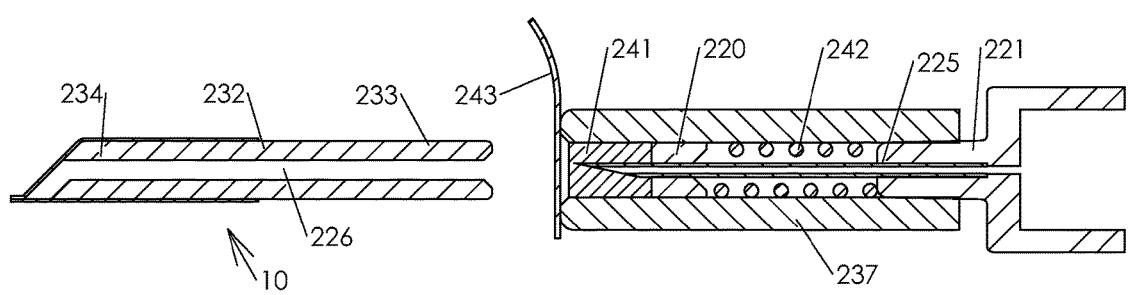

FIG. 24 illustrates another arrangement similar to the arrangement of FIG. 23 with the exception that a rubber septum 241 is disposed on the tip of the needle, and a spring 242 biases the centering piece 220 and the septum 241 toward the distal end of the adapter 237. The needle is aseptically sealed by the septum 241. For transferring material between the cartridge 10 and the syringe 221, the distal end 233 of the fitment 232 is introduced into the adapter 237, thereby displacing the septum and centering piece backward, and exposing the tip of the needle 225 to the passageway 226 in the fitment 232. When the cartridge 10 is removed, the spring 242 causes the septum to return to cover the tip of the needle 225, thereby providing protection from mechanical damage and contamination to the needle 225 until the time of use. The adapter 237 is removed with the spring 242, the centering piece 220, and the septum 241 prior to use of the syringe 221. FIG. 24b illustrates the arrangement of FIG. 24a with the addition of an aseptic foil preventing contamination to the needle and septum until integration with the cartridge.

FIG. 25a illustrates a pre-filled cartridge 10 comprising a coupler 251 and a package 10' associated via the fitment 257. The coupler assembly 250 comprises the coupler 251 and a needle assembly 253 comprising a Luer lock hub 255 and a stainless steel canula 254 joined to the hub 255. The needle assembly 253 (or needle) is accommodated in a needle cap formed in the coupler 251. The coupler 251 includes a first end and a second end, wherein the first end is coupled with the package 10' and the second end receives the needle assembly 253. The coupler 251 further comprises a fluid passageway 258 for communicating the needle assembly 253 with the cartridge 10. A rubber sheath 252 disposed in the coupler 251 forms an aseptic seal between the needle hub 255 and the coupler 251. The tip of the rubber sheath 252 forms a fluid-tight closure of the fluid passageway 258, which is pierced by the canula 254 to establish fluid communication between the needle assembly 253 and the package 10'. The Luer end 256 of the needle hub 255 is sealed with a removable aseptic closure either in the form of a sealed foil, a closure or other means known in the art. The cartridge 10 comprises a first rupturable barrier or frangible seal 19' segregating between a first compartment 15 containing a first constituent and a second compartment 16 containing a second constituent. The first and second constituents are allowed to merge when the rupturable barrier is ruptured. In another configuration, the cartridge 10 comprises a single constituent of the beneficial agent. In yet another embodiment, the cartridge 10 comprises at least a third compartment comprising a third constituent segregated from the second or the first compartments by a rupturable barrier. A second rupturable barrier or frangible seal 19" provides a closure between the second compartment 16 and the fitment 257 leading to the fluid passageway 258 in the coupler 251.

FIG. 25*b* illustrates the arrangement of FIG. 25*a* after the first and the second rupturable barriers have been opened, allowing the first and second constituents to merge, and establishing fluid communication of the mixture in joined compartment 16' with the needle 253 via the coupler 251. This arrangement provides a simple pre-filled cartridge that can be mounted on a standard Luer syringe 259 via engagement of the female Luer connector of the needle 253 with the male Luer of the Luer syringe 259, to transfer a dispensable product or constituents of such from the cartridge 10 to the reservoir of the syringe 259. The product in joined compartment 16' can then be taken into the syringe by retracting the syringe's piston, after which the coupler may be removed to expose the needle 253 for injection as shown in FIG. 25*c*. In one configuration, the syringe may contain a third constituent that may be merged with the product held in joined compartment 16' either by drawing the product in joined compartment 16' into the already partly filled syringe, or by first dispensing the third constituent from the syringe to the cartridge 10 and secondly draw the mixture back to the syringe or to a different delivery device. The coupler 251 further provides a backing for part of the cartridge 10.

Figure 25E:
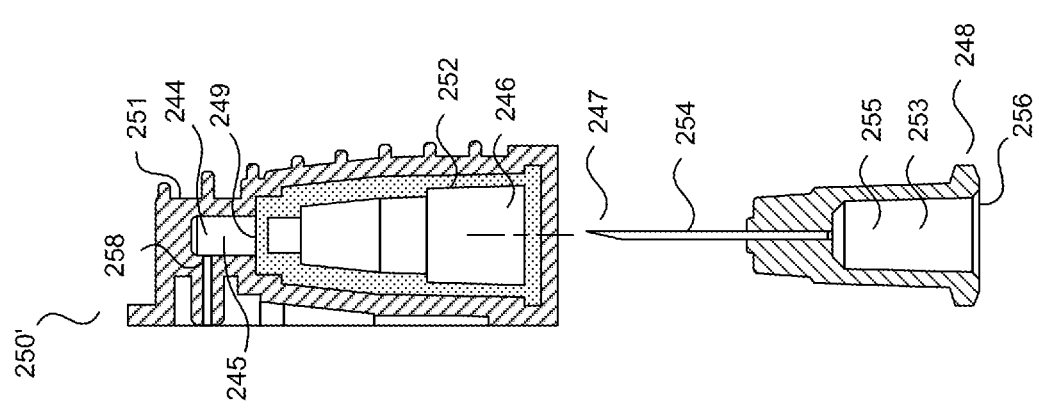
FIG. 25e illustrates an exploded view of a cap portion of the cartridge of FIGS. 25a to 25c.
Figure 25D:
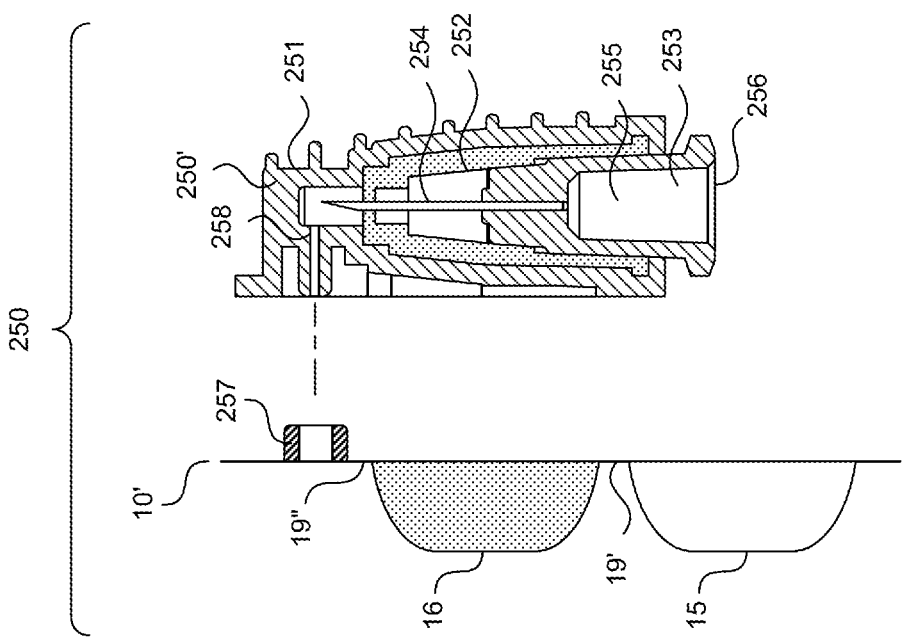
FIG. 25d illustrates two sub-assemblies of the pre-filled cartridge of FIGS. 25a to 25c.

FIG. 25*d* shows the two subassemblies of the cartridge assembly 250 including the package 10' and coupler assembly 250'. FIG. 25*e* shows an exploded view of the coupler assembly 250' (also referred to as a cap).

The coupler 251 is a cap of the administration portion of a delivery device in a form of a needle assembly 253. The cap includes a first compartment 245 configured to receive a proximal end 247 of the administration device, a second compartment 246 configured to receive the distal portion 248 of the administration device, and a barrier 249 forming a fluid-tight seal between the first and second compartments 245, 246. The proximal end 244 of the first compartment 245 is configured to communicate with the administration portion 253. The barrier 249 is configured to tightly seal around a portion of the administration device 253 between the proximal end and the distal end of the barrier 249 (i.e. around the canula 254).

Figure 26:
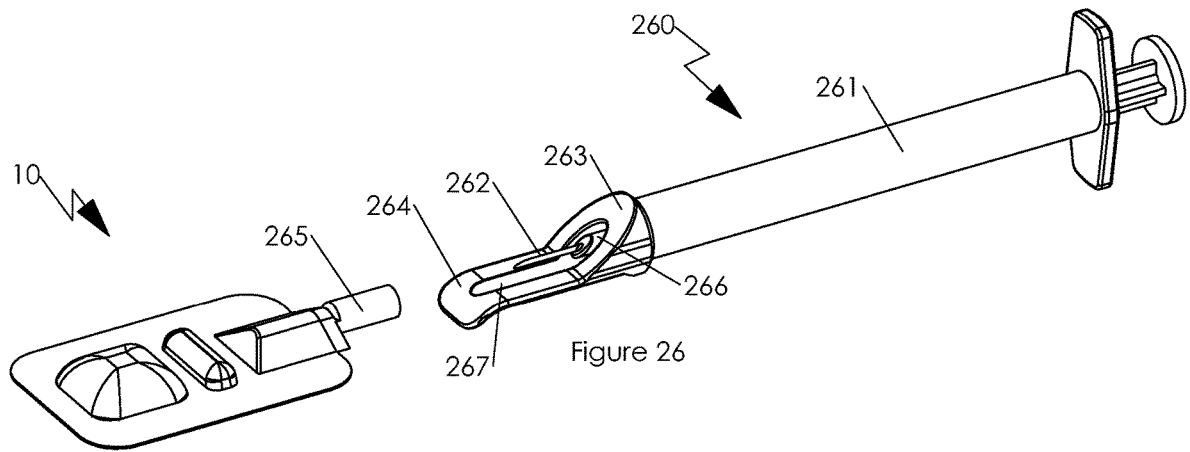
FIG. 26 illustrates a cartridge adopted for a syringe with an intradermal (ID) injection adapter.

FIG. 26 illustrates a pre-filled unit-dose aseptic reconstitution cartridge comprising a cartridge or package 10 adapted to communicate with a syringe 260. The syringe 260 comprises an intradermal (ID) injection adapter (ID Adapter), comprising a forwardly protruding skid 264 facilitating a shallow insertion of the needle 262 into the skin. US Pat. Publication Nos. 2010/0137831 and 2011/0224609 teach similar arrangements for an adapter to facilitate intradermal injection and are incorporated herein in their entireties by this reference. The ID adapter may be an integral portion of the syringe 261 or be a clip-on to the syringe 261, thereby forming an ID syringe. A recess 267 is formed in the skid 264 to facilitate the introduction of the fitment 265 of the cartridge 10 onto the needle hub 266 of the syringe 260.

Figure 27A:
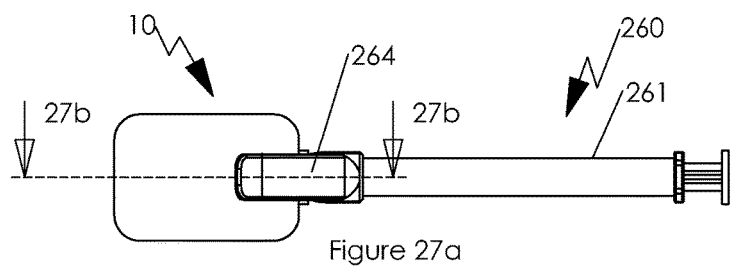
FIGS. 27a and 27b illustrate a cartridge associated with an ID syringe.
Figure 27B:
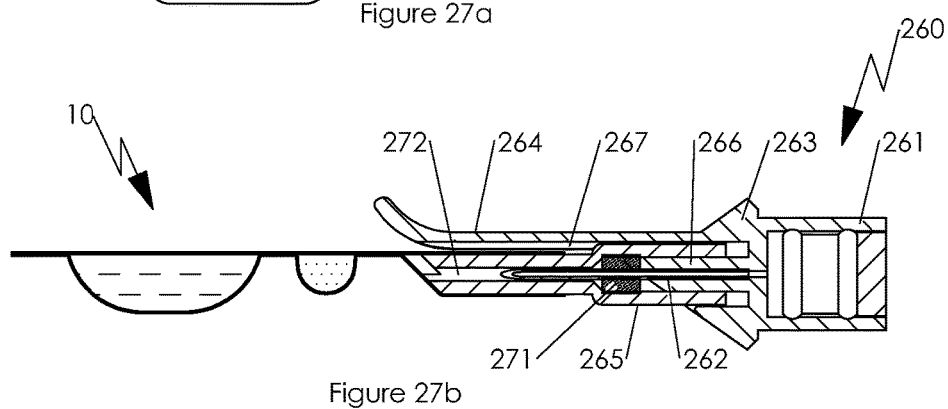

FIG. 27*a* illustrates the cartridge 10 mounted on an ID syringe where the cartridge 10 and syringe 260 are positioned in a linear arrangement. The view provides an orientation of the section view of FIG. 27*b*. FIG. 27*b* illustrates the fitment 265 press-fitted on the needle hub 266 forming an aseptic connection. A rubber stopper provides a closure to passageway 271 (also referred to as an inner bore) of cartridge 10 and is pierced by needle 262 to establish fluid communication between the syringe and the cartridge 10.

Figure 28:
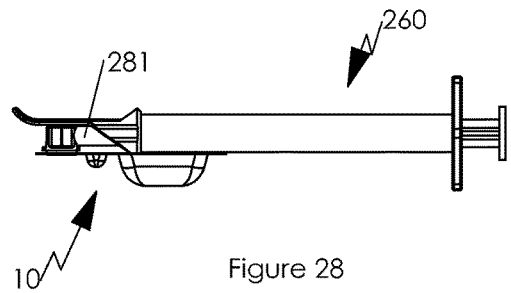
FIG. 28 illustrates another arrangement of a cartridge associated with an ID syringe.

FIG. 28 illustrates a similar arrangement to that of FIG. 10 with the exception that the fitment 281 is made such that the cartridge 10 is positioned parallel to the syringe barrel instead of in line with the syringe axis.

Figure 29A:
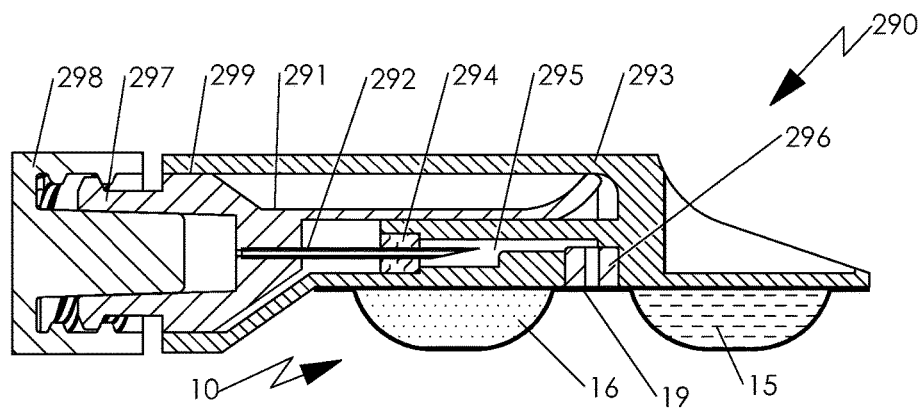
FIGS. 29a and 29b illustrate another arrangement of a cartridge comprising an ID needle arrangement.
Figure 29B:
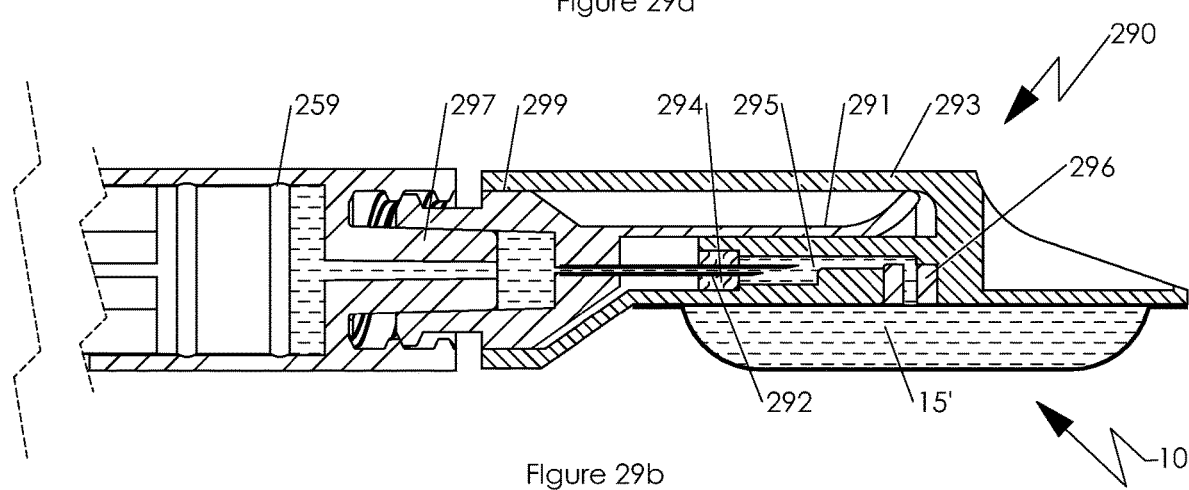

FIGS. 29*a* and 29*b* illustrates a cartridge configuration 290 comprising a coupler 293 communicating an intradermal needle assembly 291 and the cartridge 10. The coupler accommodates a needle assembly comprising a canula 292 and a needle hub 291 comprising the forward protruding skid at its distal end and a Luer connector at its proximal end 297. The coupler 293 is used as an aseptic cap engaged with the needle hub 291 in sealing area 299 maintaining the needle 292 and the skid area sterile. Hence, the coupler 293 may operate as a cap that covers, protects, or at least partially encloses an administration portion such as the needle 292. A Luer cap 298 is aseptically sealing the Luer connector at the proximal end 297 of the needle hub 291 to form an integrally sealed cartridge that remains sterile without the need of a sterile overwrap. The cartridge 10 and the coupler are connected via the fitment 296. The fitment is preferably heat welded to the wall of the cartridge 10, and is connected to the coupler by one of the means known in the art including heat welding, bonding, or a tight mechanical fit. The rupturable seal 19 between the first compartment 15 and the second compartment 16 provides a closure segregating the compartments from the coupler 293.

FIG. 29*b* illustrates the arrangement of FIG. 29*a* wherein the Luer cap 298 is replaced with a Luer syringe 259, and the rupturable seal is opened to allow the constituents in the first and second compartments 15, 16 to merge and establish fluid communication with the needle via passageway 295, thereby allowing filling the reservoir of the syringe. A rubber closure or stopper 294 limits the dead space of the constituents in the coupler to the minute volume of passageway 295, thus limiting waste of the product 15'. FIG. 29*b* shows the piston of the syringe retracting to receive the product 15' in the syringe's barrel (i.e. the syringe's reservoir). The coupler 293 is removed to expose the needle and the ID adapter for injection. The coupler 293 provides a backing to the cartridge 10 thereby facilitating depression of the compartments of the cartridge 10.

Figure 30:
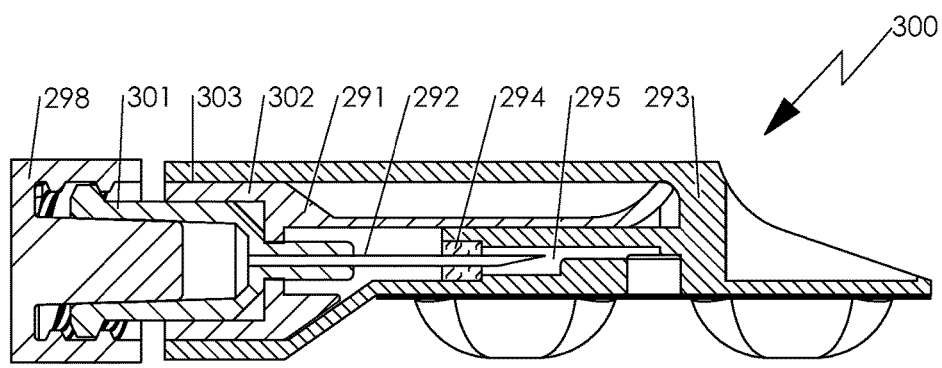
FIG. 30 illustrates another arrangement of a cartridge comprising an ID needle arrangement.

FIG. 30 illustrates a cartridge arrangement 300 similar to the cartridge arrangement 290 of FIGS. 29*a* and 29*b* with the exception that the ID adapter 291 is a separate part from the needle hub 301, and is mounted on a needle hub. A sealing portion 302 of the needle hub 291 seals with the coupler 293 at a sealing area 303.

Figure 31A:
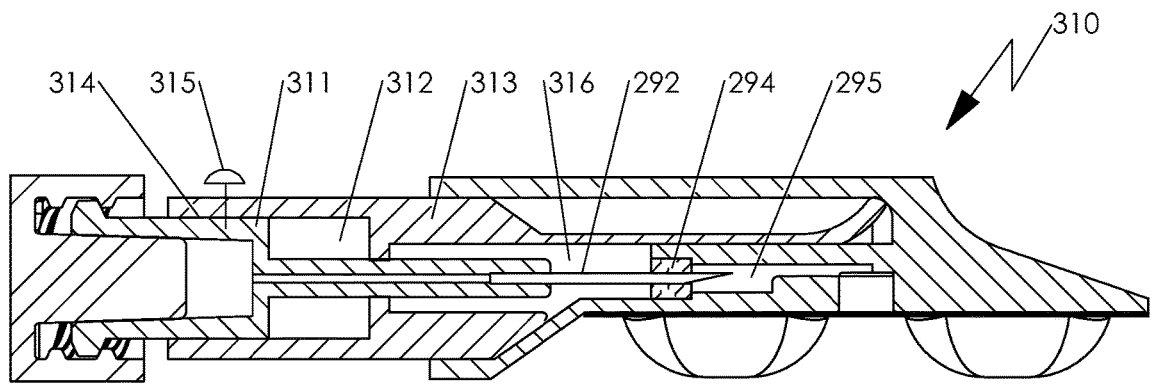
FIGS. 31a and 31b illustrate a cartridge comprising a needle safety and disabling feature.
Figure 31B:
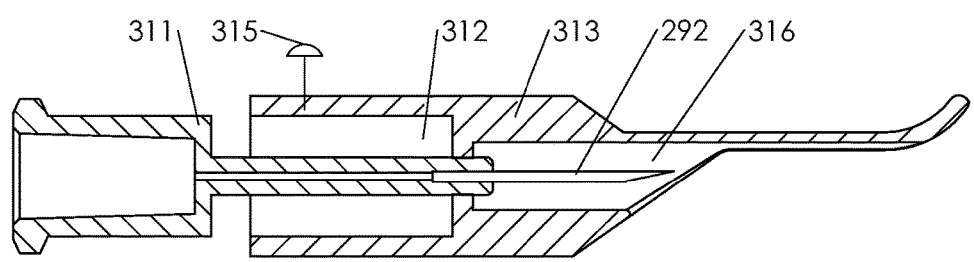

FIG. 31*a* shows a cartridge arrangement 310, mostly similar to the cartridge arrangement 300 of FIG. 30 with the exception that the needle hub 311 is movably disposed in the ID adapter 313, movable between an injection position and safe-discard position. A latch mechanism 315 retains the injection position at a sealing interface 314 with the needle hub 311. A spring may be disposed in area 312 to bias the ID adapter or needle hub 313 to the safe-discard position. FIG. 31*b* illustrates cartridge arrangement 310 when the latch has been operated to release the needle hub. The needle assembly is retracted to bring the needle tip to a confined section 316 to reduce the risk of needle sticks. In one arrangement, the needle hub is permanently locked in this position to prevent repeated use of the needle.

Figure 32:
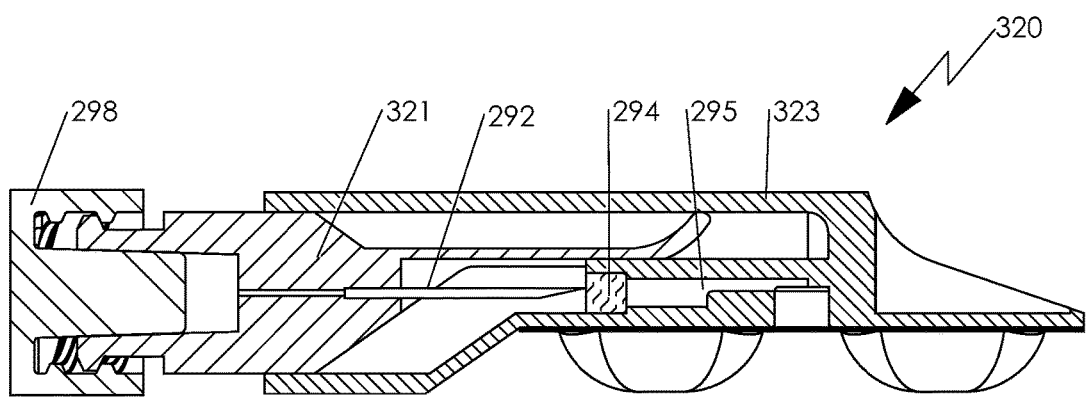
FIG. 32 illustrates a cartridge with a movable needle.

FIG. 32 shows a cartridge arrangement 320 similar to arrangement 290 of FIGS. 29a and 29b with the exception that the needle assembly with needle hub 321 is movably disposed in the coupler 323. The needle hub 321 is movable between a first position where the needle canula 292 does not pierce the rubber closure 294 (also referred to as a stopper 294), or is only partly piercing the rubber closure 294, and a second position where the needle tip pierces the stopper 294 to establish fluid communication with the fluid passageway 295.

Figure 33A:
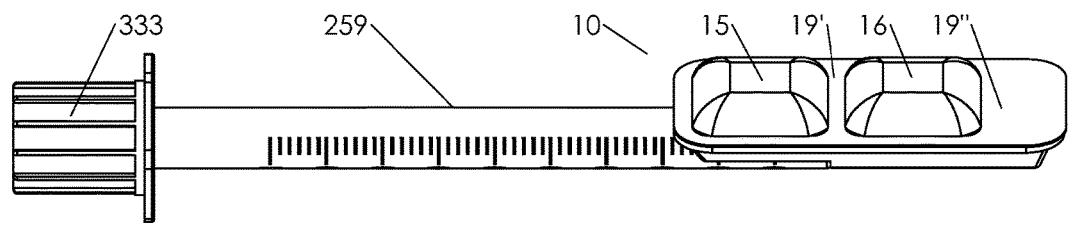
FIGS. 33a to 33e illustrate a pre-filled syringe arrangement.
Figure 33B:
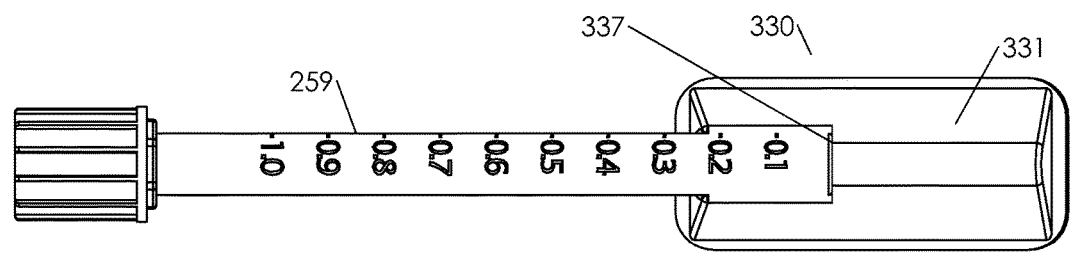
Figure 33C:
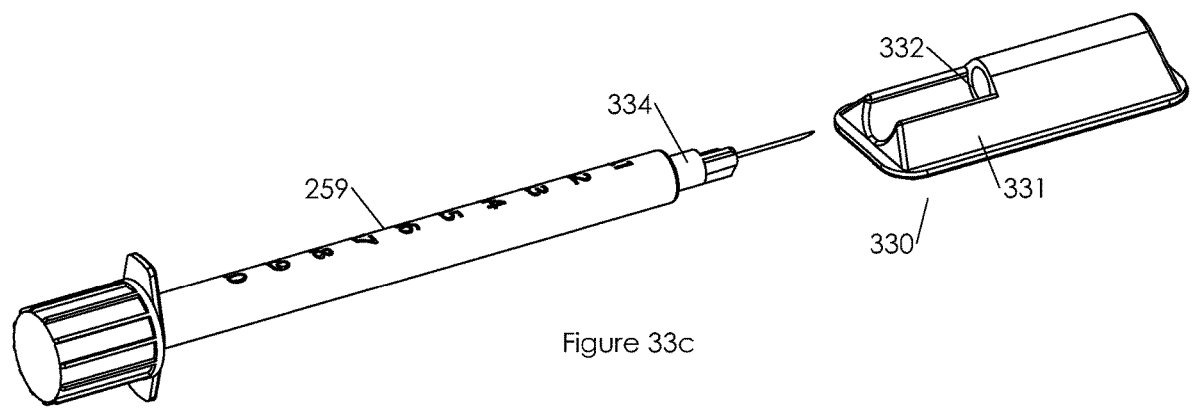
Figure 33D:
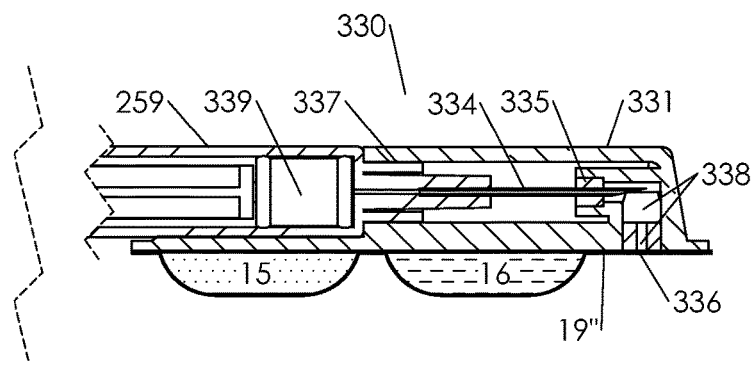
Figure 33E:
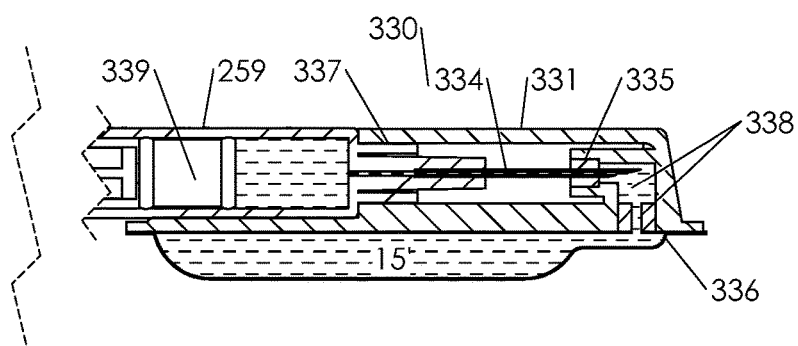

FIG. 33a to FIG. 33c illustrates a pre-filled Luer syringe 259 comprising a regular piston-and-barrel syringe arrangement with a staked needle 334 for delivering medication. A syringe cap 331 communicates with the syringe in an aseptic engagement 337. The cap 331 is engaged with a cartridge 10 to form a removable cartridge 330. The body of the cap 331 operates as a coupler between a fitment 336 of the cartridge and the needle. FIGS. 33d and 33e show a scaled-up section view of the cap during storage and after activation as the dose 338 is being filled to the syringe's barrel with a plunger 339. The cap comprises a rubber stopper 335 that is pierced through by the needle 334.

Similar configurations may be operative with other needle arrangements known in the art including, for example, syringe with catheter, needle with protective soft sheath, intramuscular (IM) needle, Subcutaneous (SQ) needle, Intradermal (ID) needle, micro-needle, safety needles, retractable needle, irrigation needle, applicator, etc.

The syringe further comprises an aseptic closure 333 to the barrel such that this syringe assembly is maintained sterile without the need of a sterile overwrap.

Figure 34:
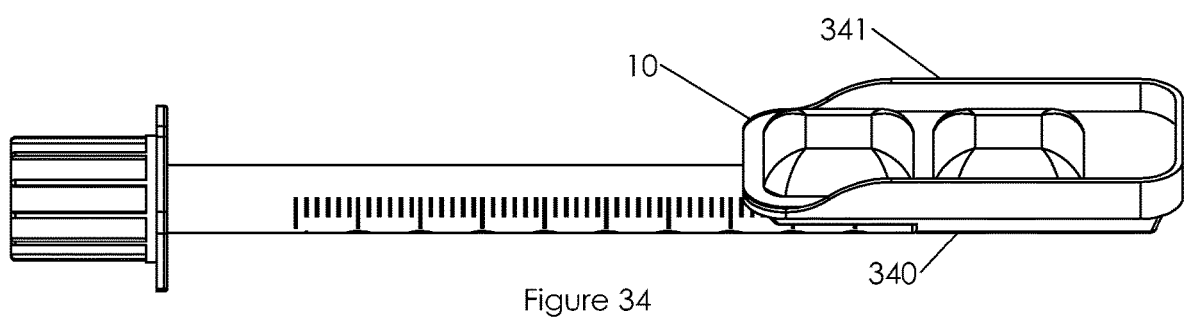
FIG. 34 illustrates a cartridge with a backing and walls protecting the pre-filled package of the cartridge.

FIG. 34 illustrates an arrangement similar to the arrangement of FIG. 33 with the addition of protective walls 341 vertically protruding to protect the cartridge 10 of a removable cartridge 340. The protection of the cartridge can be enhanced by further surrounding the cartridge with additional wall, a flip-over cover associated with the wall 341, a slideable cover, etc.

Figure 35A:
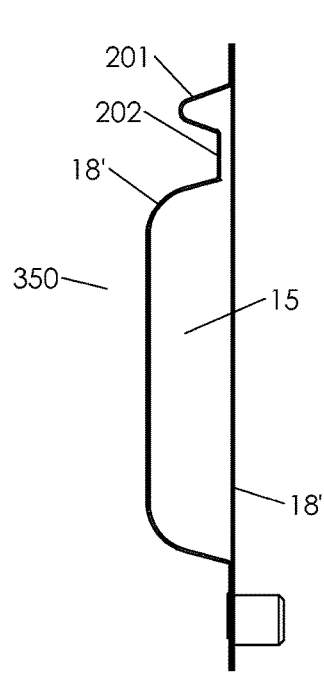
FIGS. 35a to 35f illustrate filling steps of one method of filling a package.

FIGS. 35a to 35f illustrate filling steps of one method of filling a package 350. The package 350 comprises a first pre-formed wall 18' and a second flat wall 18" joined to form a compartment 15. A filling compartment 201 is interfacing the storage compartment 15 via a sealable filling channel 202. FIG. 35a illustrates the package 350 prior to filling, wherein a cavity defined by the storage compartment 15, the filling compartment 201, and the filling channel 202 is integrally sealed. The package may be sterilized by heat or radiation.

Figure 35B:
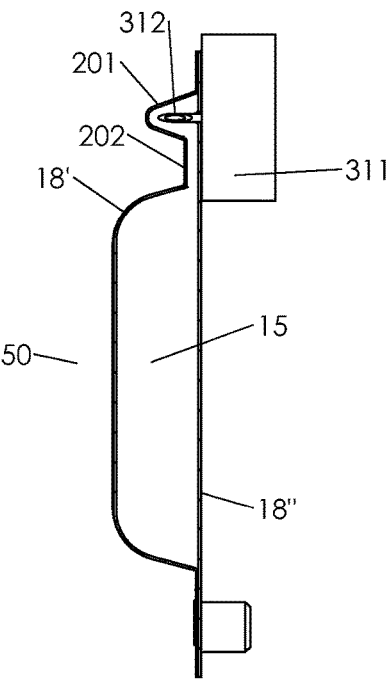

FIG. 35b illustrates the package 350 having a filling device 311 that is engaged with the package 350. The filling device comprises a filling tube 312 having a piercing member at its distal end for piercing the second wall 18" of the package 350. The filling device 311 is engaged with the second wall 18" in a fluid tight fashion, and defines a filling port where the filling tube 312 pierces the second wall 18" in the filling compartment 201. The filling tube 312 and the filling port may be disinfected prior to engagement to further reduce contamination risks of the package. In one arrangement the package and the filling device are disinfected using hydrogen peroxide.

Figure 35C:
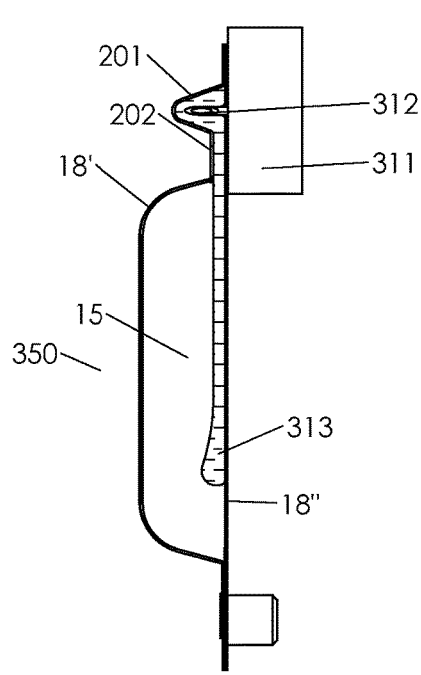
Figure 35D:
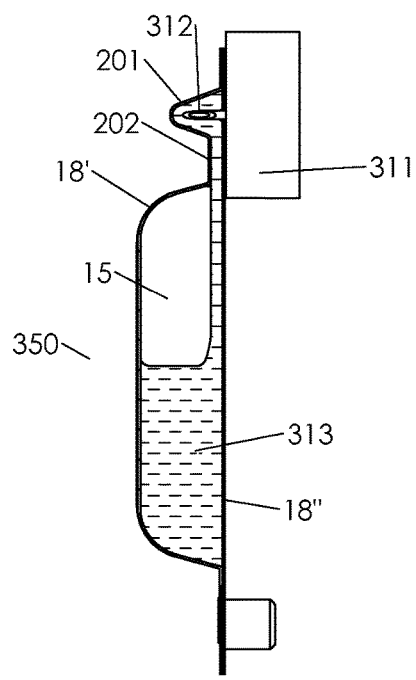

FIG. 35c illustrates the filling device 311 starting to fill the package 350. The filling channel directs the fluid 313 to glide along the second wall 18", hence reducing jetting, bubbles and foaming of the beneficial agent 313. FIG. 35d illustrates a subsequent step in the filling process where the package is about half full. The fluidic constituent 313 continues to flows along the second wall 18" avoiding jetting and reducing bubbles, foaming and mixing of the filled product. A gas content within the package 350 may be evacuated through the filling passageway 202 or another sealable filling outlet.

Figure 35E:
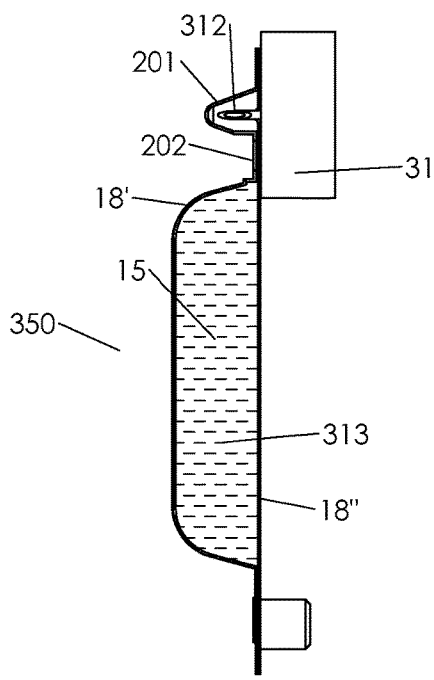
Figure 35F:
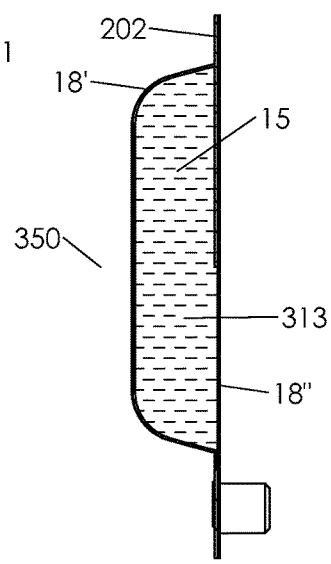

FIG. 35e illustrates the storage compartment 15 completely filled and sealed. A sealing device collapses and thermally seals the channel 202. In one arrangement, the filling compartment 201 is squeezed prior to sealing the channel 202 to transfer the fluidic content of the filling compartment 201 to the storage compartment 15. In another arrangement, the fluidic content of the filling compartment 201 is sucked back into the filling tube 312 after sealing the channel 202. FIG. 35f shows the package after the filling device is retracted and the filling compartment 201 section is trimmed and sacrificed.

Figure 36:
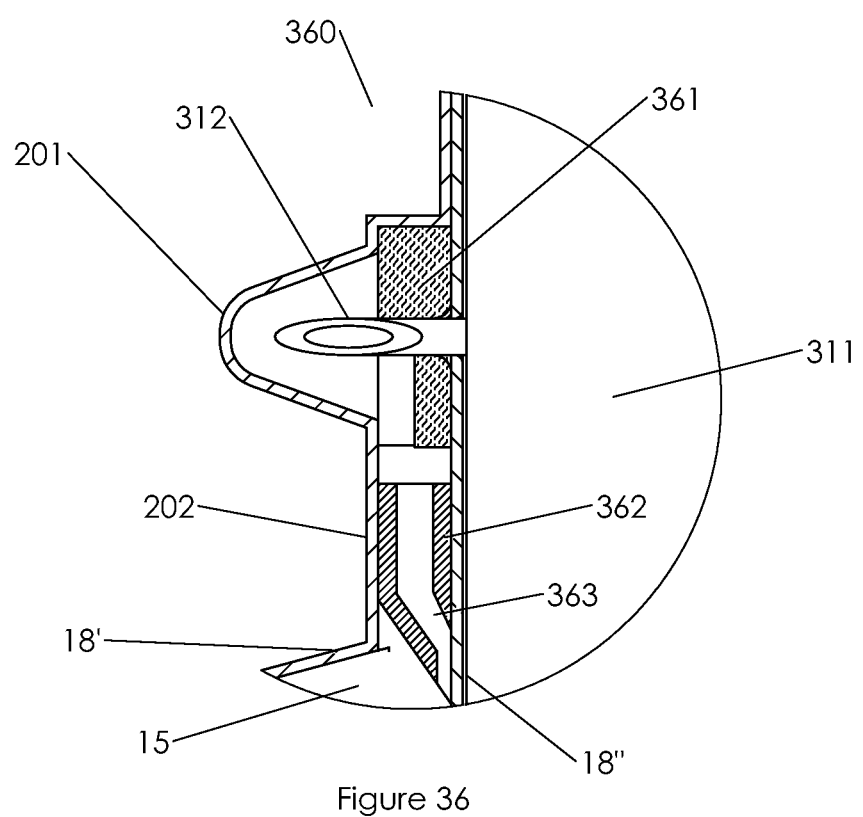
FIG. 36 illustrates an arrangement of a portion of a package having a first insert disposed in the filling compartment, and a second insert disposed in the filling channel.

FIG. 36 illustrates an arrangement of a portion of a package 360 having a first insert 361 disposed in the filling compartment 201, and a second insert 362 disposed in the filling channel 202. The first insert 361 serves as a seal to enhance a fluid-tight seal between the filling device 311 and the package 360. The second insert 362 comprises an internal channel 363 configured to direct the incoming fluid to compartment 15 to glide along the second wall 18". In one arrangement, the second insert comprises a low-melting temperature material that is adherebly compatible with the first wall 18' and the second wall 18". Hence, the second insert 362 will melt, collapse, and seal the channel 202 at the sealing step.

The cartridges of the arrangements of this disclosure may carry any marking including printing, barcoding, RFID tags, embossment, and engraving to communicate desired information with a person or a device. The cartridge may be extended to provide sufficient marking surface as needed.

A compression panel may be associated with the cartridge to facilitate depression of at least one compartment of the cartridge either to urge the rupture of a rupturable barrier, or to urge expression of the dispensable product from the cartridge.

The arrangement and method described above is applicable for other injectors or dispenser types such as the jet injector cartridge taught in FIG. 1 or other arrangements discussed in this document. In one arrangement, a retractable needle mechanism, retractable needle connector mechanism, or other needle safety mechanisms, and reuse disabling mechanism or prevention device is incorporated with the mixing syringe mechanism described herein.

The cartridge arrangement of the present disclosure may be combined with several forms of delivery devices or applicators to facilitate a desired form of use. A compression panel or roller may be incorporated to facilitate an efficient expression of the cartridge's content. The delivery devices or applicators may include, for example, any one of a medical syringe, staked needle syringe, safety syringe, retractable needle syringe, auto-disabling syringe, auto-injector, jet-injector, intradermal syringe, subcutaneous syringe, intramuscular syringe, infusor, infusion pump, sustained release delivery system, and patch pump.

The applications of the present invention are not limited to the syringe and jet-injector applications which are provided here by way of example, and the teachings described herein can be applied to other applications such as aseptic filling of micro-pump reservoir, intramuscular auto injectors, intradermal auto injectors, etc.

What is claimed is:

1. A pre-filled cartridge assembly comprising:
a package comprising:
a flexible wall establishing at least a portion of at least a first compartment containing at least one constituent of a beneficial agent;
an administration device comprising:
a proximal end configured to administer the beneficial agent to a subject from a proximal terminal end; and
a distal end configured to engage with a delivery device; and
a coupler comprising:
a first portion coupled with the package; and
a second portion comprising an aseptically sealed compartment in fluid communication with a fluid passage, the aseptically sealed compartment configured to receive the proximal terminal end of the administration device therein in a fluid-tight fashion to establish fluid communication between the administration device and the aseptically sealed compartment, wherein the aseptically sealed compartment, the first compartment, and the fluid passage are aseptically sealed relative to the ambient environment, and
wherein the administration device is at least partially disposed within the coupler.

2. The pre-filled cartridge assembly of claim 1, wherein the administration device comprises at least one of a connector, a Luer connector, a needle, a micro-needle, a subcutaneous needle, an intradermal needle, a nozzle, a jet-injector nozzle, a catheter, a tube, or a coupler to the same.

3. The pre-filled cartridge assembly of claim 1, wherein a closure is disposed within the coupler to define the aseptically sealed compartment and preventing fluid communication between the package and the administration device until opened.

4. The pre-filled cartridge assembly of claim 3, wherein the closure is configured to open upon a movement of the administration device relative to a cap to dispose the proximal terminal end in the aseptically sealed compartment.

5. The pre-filled cartridge assembly of claim 1, wherein the flexible wall is pre-formed such that the first compartment has a deformable structure.

6. The pre-filled cartridge assembly of claim 1, wherein the proximal end of the administration device comprises a needle.

7. The pre-filled cartridge assembly of claim 1, wherein the delivery device with which the distal end of the administration device is configured to engage comprises a syringe.

8. The pre-filled cartridge assembly of claim 1, wherein the coupler is configured to provide physical protection to at least the proximal end of the administration device.

9. The pre-filled cartridge assembly of claim 1, wherein the coupler is configured to provide an aseptic enclosure to at least the proximal end of the administration device by forming an aseptic seal between the administration device and the coupler.

10. The pre-filled cartridge assembly of claim 9, wherein the aseptic seal includes an elastic seal compressed between the coupler and the administration device.

11. The pre-filled cartridge assembly of claim 1, wherein when the administration device is configured such that when the administration device is engaged with the delivery device:
the administration device establishes fluid communication between the package and the delivery device, thereby allowing withdrawal of beneficial agent from the package to the delivery device; and
thereafter, when removed from the coupler, allows administration of the beneficial agent from the delivery device to a subject through the administration device.

12. The pre-filled cartridge assembly of claim 1, wherein the package further comprises:
a fitment separated from the first compartment by a rupturable barrier, the first portion coupled to the package by the fitment,
wherein the coupler further comprises:
a flat backing surface located on an exterior of the coupler and extending relative to the fitment of the package, wherein at least a portion of the package rests against the flat backing surface of the coupler when the fitment of the package is engaged with the coupler.

13. The pre-filled cartridge assembly of claim 1, wherein the aseptically sealed compartment contains the proximal terminal end.

14. The pre-filled cartridge assembly of claim 1, wherein the administration device includes a hypodermic needle, a canula, a catheter, a connector, a Luer connector, a nozzle, a spray nozzle, a jet nozzle, a dispenser, an oral dispenser, an auricular dispenser, an ocular dispenser, or a topical dispenser.

15. The pre-filled cartridge assembly of claim 1, wherein the distal end of the administration device is aseptically sealed by a removable aseptic closure, the removable aseptic closure aseptically sealing the aseptically sealed compartment relative to the ambient environment.

16. The pre-filled cartridge assembly of claim 1, wherein the aseptically sealed compartment is aseptically sealed relative to the ambient environment by an element of the administration device or by an element coupled to the administration device.

17. The pre-filled cartridge assembly of claim 1, wherein the package further comprises:
a fitment separated from the first compartment by a rupturable barrier, the first portion coupled to the package by the fitment, wherein the rupturable barrier is configured to rupture to establish fluid communication between the first compartment and the aseptically sealed compartment via the fluid passage.

18. The pre-filled cartridge assembly of claim 1, wherein the package further comprises:
a fitment separated from the first compartment by a rupturable barrier, the first portion coupled to the package by the fitment.

* * * * *